(12) United States Patent
Iwami

(10) Patent No.: US 10,338,008 B2
(45) Date of Patent: Jul. 2, 2019

(54) CONDUCTIVE FILM, DISPLAY DEVICE HAVING THE SAME, AND METHOD OF EVALUATING CONDUCTIVE FILM

(71) Applicant: FUJIFILM Corporation, Tokyo (JP)

(72) Inventor: Kazuchika Iwami, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 283 days.

(21) Appl. No.: 15/389,647

(22) Filed: Dec. 23, 2016

(65) Prior Publication Data

US 2017/0102342 A1    Apr. 13, 2017

Related U.S. Application Data

(63) Continuation of application No. PCT/JP2015/068583, filed on Jun. 26, 2015.

(30) Foreign Application Priority Data

Jun. 30, 2014  (JP) .................................. 2014-135273

(51) Int. Cl.
*B32B 7/02* (2019.01)
*H01B 5/14* (2006.01)
(Continued)

(52) U.S. Cl.
CPC ......... *G01N 21/95692* (2013.01); *B32B 7/02* (2013.01); *B32B 15/02* (2013.01);
(Continued)

(58) Field of Classification Search
CPC .. G01N 21/95692; G01N 21/27; G06F 3/044; G06F 2203/04103; G06F 2203/04112
See application file for complete search history.

(56) References Cited

U.S. PATENT DOCUMENTS

2006/0158467 A1   7/2006 Larson et al.
2013/0028503 A1*  1/2013 Wakui .................. H05K 9/0086
                                        382/141
(Continued)

FOREIGN PATENT DOCUMENTS

CN     101133357 A    2/2008
JP     2008-525859 A  7/2008
(Continued)

OTHER PUBLICATIONS

Communication dated May 9, 2017, issued from the Japan Patent Office in the corresponding Japanese Patent Application No. 2014-135273.

(Continued)

*Primary Examiner* — Alexander Eisen
*Assistant Examiner* — Kebede T Teshome
(74) *Attorney, Agent, or Firm* — Sughrue Mion, PLLC

(57) ABSTRACT

In a conductive film, a method of evaluating a pattern in the conductive film, and a display device, thin metal lines of at least one wiring portion of two wiring portions is formed in a wiring pattern where the opening portions, of which angles are maintained and pitches are made to be irregular with respect to rhomboid shapes of a regular rhomboid wiring pattern, have parallelogram shapes. In frequencies of the moirés that are equal to or less than a frequency threshold value and are calculated for each color from two peak frequencies and two peak intensities of 2DFFT spectra of image data of the wiring patterns of the two wiring portions and luminance image data of pixel array patterns of the respective colors at the time of lighting up for each single color, the wiring patterns of the two wiring portions are formed such that an indicator of evaluation of moirés is equal to or less than an evaluation threshold value. The indicator of evaluation is calculated from evaluation values (Continued)

of the moirés of the respective colors obtained by applying human visual response characteristics in accordance with an observation distance to intensities of the moirés equal to or greater than an intensity threshold value.

19 Claims, 18 Drawing Sheets

(51) Int. Cl.
    *H05K 9/00*     (2006.01)
    *B32B 15/02*     (2006.01)
    *G01N 21/27*     (2006.01)
    *G01N 21/95*     (2006.01)
    *G06F 3/041*     (2006.01)
    *G06F 3/044*     (2006.01)
    *G01N 21/956*     (2006.01)

(52) U.S. Cl.
    CPC ............. *G01N 21/27* (2013.01); *G06F 3/041* (2013.01); *G06F 3/044* (2013.01); *G06F 3/0412* (2013.01); *H01B 5/14* (2013.01); *H05K 9/00* (2013.01); *B32B 2307/202* (2013.01); *B32B 2307/412* (2013.01); *B32B 2457/20* (2013.01); *G01N 2021/9511* (2013.01); *G06F 2203/04103* (2013.01); *G06F 2203/04112* (2013.01)

(56) References Cited

U.S. PATENT DOCUMENTS

2015/0061942 A1* 3/2015 Koyama ................... G09F 9/00
                                                          343/700 MS 2015/0152279 A1* 6/2015 Kai ....................... C09D 201/00
                                                            428/216

2015/0342034 A1     11/2015 Iwami

FOREIGN PATENT DOCUMENTS

| JP | 2009117683 A | * | 5/2009 |
|---|---|---|---|
| JP | 2010-089488 A | | 4/2010 |
| JP | 2013-163307 A | | 8/2013 |
| JP | 2013-214545 A | | 10/2013 |
| KR | 10-2007-0105975 A | | 10/2007 |
| WO | 2014/123009 A1 | | 8/2014 |

OTHER PUBLICATIONS

Communication dated May 17, 2017, issued from the Europe Patent Office in corresponding European Patent Application No. 15814906.2.

Communication dated Sep. 11, 2017 issued by Korean Intellectual Property Office in counterpart application No. 10-2016-7036439.

International Preliminary Report on Patentability and translation of Written Opinion, dated Jan. 12, 2017, from the International Bureau in counterpart International application No. PCT/JP2015/068583.

International Search Report PCT/JP2015/068583, dated Sep. 15, 2015.

Communication dated Nov. 7, 2017, issued from the Japan Patent Office in corresponding Japanese Patent Application No. 2014-135273.

Communication dated Oct. 22, 2018 issued by the State Intellectual Property Office of People's Republic of China in counterpart application No. 201580035353.8.

* cited by examiner

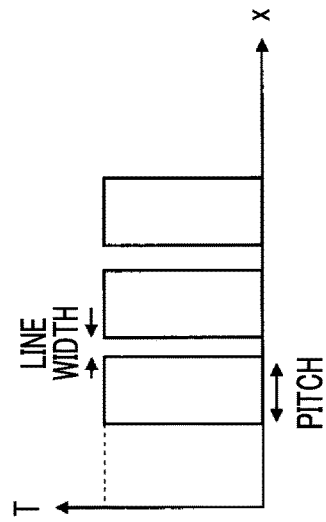
FIG. 11A
MESH PATTERN
FIG. 11C
PRESENT INVENTION
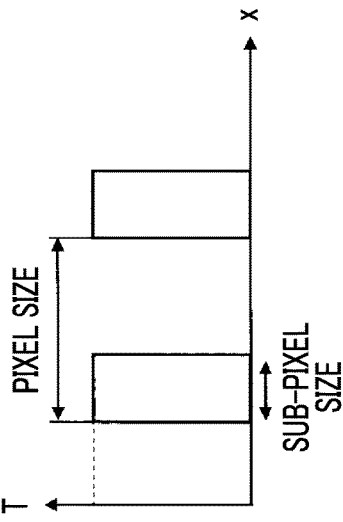
FIG. 11E
RELATED ART
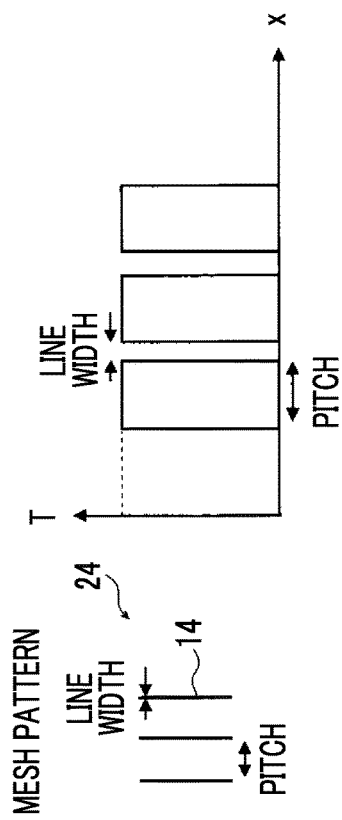
FIG. 11B
FIG. 11D
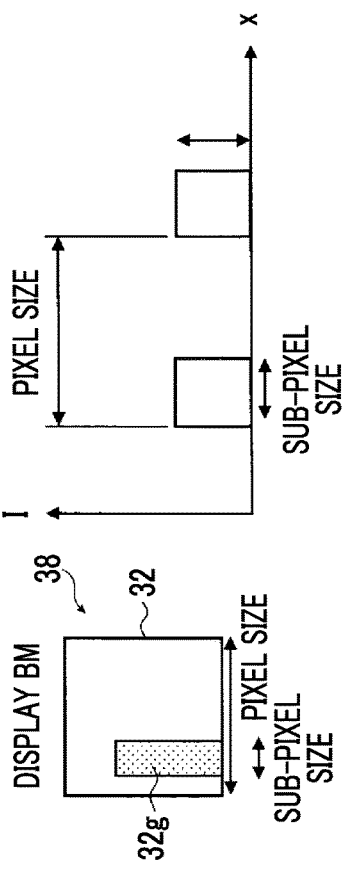
FIG. 11F

CAPTURED IMAGE

INPUT DATA (A)  (B)

CONDUCTIVE FILM, DISPLAY DEVICE HAVING THE SAME, AND METHOD OF EVALUATING CONDUCTIVE FILM

CROSS-REFERENCE TO RELATED APPLICATIONS

This application is a Continuation of PCT International Application No. PCT/JP2015/068583 filed on Jun. 26, 2015, which claims priority under 35 U.S.C. § 119(a) to Japanese Patent Application No. 2014-135273 filed on Jun. 30, 2014. The above application is hereby expressly incorporated by reference, in its entirety, into the present application.

BACKGROUND OF THE INVENTION

1. Field of the Invention

The present invention relates to a conductive film, a display device having the same, and a method of evaluating the conductive film. Specifically, the present invention relates to a conductive film that has a random mesh-shaped wiring pattern capable of providing image quality which is improved in terms of visibility of moiré in accordance with an emission intensity of a display device even if the pattern overlaps with pixel array patterns of the display device having different emission intensities, a display device having the same, and a method of evaluating the conductive film. It should be noted that, in the present invention, the visibility of moiré indicates a degree to which moiré is not visually perceived or a degree to which it is difficult for moiré to be visually perceived. In addition, improvement or advancement in terms of the visibility of moiré means that it becomes difficult for moiré to be visually perceived or that moiré does not become visually perceived.

2. Description of the Related Art

Examples of conductive films, each of which is provided on a display unit of a display device (hereinafter referred to as a display), include a conductive film for a touch panel having a conductive layer formed of thin metal lines which have a mesh-shaped wiring pattern (hereinafter referred to as a mesh pattern), a conductive film for an electromagnetic shield, and the like.

Regarding such conductive films, since there is a problem that a moiré caused by interference between a mesh pattern and a pixel array pattern (for example referred to as an array pattern of RGB color filters or a black matrix (hereinafter also referred to as a BM pattern as a reverse pattern thereof) of a display may be visually perceived, various conductive films having a mesh pattern due to which a moiré is not visually perceived or unlikely to be visually perceived have been proposed (for example, refer to JP2013-214545A).

In a technology disclosed in JP2013-214545A according to the present application of the applicants, a rhomboid shape of a mesh pattern, which allows the sum of intensities of moirés within a predetermined frequency range in which the frequency of moiré is determined depending on visual response characteristics to be equal to or less than a predetermined value, is made to be irregular in accordance with widths of thin metal lines constituting the mesh pattern, with respect to frequencies and intensities of moirés obtained by applying human visual response characteristics to frequency information and intensity information of moirés respectively calculated from peak frequencies and peak intensities of respective spectrum peaks of a two-dimensional Fourier (2DFFT) spectrum of transmittance image data of a rhomboid (diamond) mesh pattern of the conductive film and a two-dimensional Fourier (2DFFT) spectrum of transmittance image data of a pixel array (BM) pattern of the display. As a result, it is possible to suppress occurrence of moiré, and it is possible to improve visibility.

SUMMARY OF THE INVENTION

Meanwhile, in JP2013-214545A, moiré is quantified by performing convolution of the FFT spectrum of the rhomboid (diamond) mesh pattern and the FFT spectrum of the BM pattern of the display, and the pattern is made to be irregular. As a result, image quality is improved in terms of moiré visibility.

However, in JP2013-214545A, the pixel array pattern of the display, which is used when moiré is predicted, is typified only by sub-pixels for just a single color, for example, a BM pattern of a G channel, and a luminance of the display is not considered. As a result, the Fourier spectrum of the BM pattern of the display depends on only spatial frequency characteristics of the sub-pixels for the single color, for example, the G channel. In a case where a different display is used, particularly the emission intensity is not considered, and thus there is no consistency in quantitative values. Accordingly, a problem arises in that, in accordance with a display, moiré is not sufficiently prevented from occurring and image quality cannot be improved in terms of visibility. As a result, there is a problem that the visibility of moiré of a different display cannot be sufficiently evaluated.

For example, it is not possible to simply compare a quantitative value of moiré, which is visually perceived in a case where a certain specific pattern is applied to a high resolution smartphone, with a quantitative value of moiré which is visually perceived in a case where a certain specific pattern is applied to a medium resolution laptop. The reason for this is that the respective displays have different emission intensities, moiré, which is visually perceived, is strong if the emission intensity is strong, and moiré, which is visually perceived, is weak if the emission intensity is weak.

Meanwhile, recently, for example, as typical pixels of an organic EL display (OELD: Organic ElectroLuminescence Display), pixels having the characteristics in which it is not necessary for opening shapes of RGB color filters, that is, shapes of sub-pixels to be substantially the same; and phases thereof, that is, phases of repeated patterns and cycles thereof are arbitrary (random) have been used. In the pixels arbitrarily configured in such a manner, the visibility of moiré, which is visually perceived due to lamination of a conductive film having the mesh-shaped wiring pattern on the pixels of the display, is different in accordance with an array pattern and a shape (including a size) of each sub-pixel of RGB. Therefore, the visibility depends on the emission intensity of the display, but luminances of the array patterns of the respective sub-pixels are different. However, in the technology disclosed in JP2013-214545A, only spatial frequency characteristics of the pixel array pattern of G are considered, and thus there is a problem in that the moiré visibilities of the displays having different emission intensities and array patterns of the sub-pixels are not accurately evaluated, and moiré problems cannot be corrected.

That is, in each of the displays using pixels having various configurations and having various light intensities, in order to improve the moiré visibility of the conductive film laminated on a display screen of the display, light intensities of RGB depending on the display are necessary, and it is necessary to consider all numerical values obtained by digitizing moiré visibility for each of RGB. However, there is a problem in that the numerical values are not considered at all in JP2013-214545A.

In order to solve the problems of the related art, the present invention has an object to provide a conductive film, a display device having the same, and a method of evaluating the conductive film. The conductive film has a random mesh-shaped wiring pattern (mesh pattern) capable of preventing moirés from occurring in accordance with the intensity of the display regardless of an observation distance and greatly improving visibility, even in a case where the pattern overlaps with the pixel array pattern of a display unit (display) having a different emission intensity (luminance).

In particular, the present invention also has an object to provide a conductive film, a display device having the same, and a method of evaluating patterns of the conductive film. The conductive film has a random mesh pattern in which the emission intensity of the display unit is considered, when the conductive film overlaps with a black matrix of a display unit of a display device having a different emission intensity and is visually perceived, in a case where the transparent conductive film having the mesh pattern is used as a touch panel electrode. The conductive film is able to suppress occurrence of moiré which greatly disturbs image quality, and is able to greatly improve visibility of the display on the touch panel.

Further, in addition to the above-mentioned object, another object of the present invention is to provide a conductive film, a display device having the same, and a method of evaluating the conductive film. Also in a design of a mesh pattern of the conductive film in a case where the opening shapes of the RGB sub-pixels of the display have frequencies and intensities (shapes and sizes) different from each other, the conductive film has a mesh pattern capable of providing best image quality in combination with the pixel array pattern of a display having a different emission intensity.

In order to achieve the object, according to a first aspect of the present invention, there is provided a conductive film that is provided on a display unit of a display device, the conductive film comprising: a transparent substrate; and two wiring portions that are respectively provided on both sides of the transparent substrate and that each have a plurality of thin metal lines. The plurality of thin metal lines has a mesh-shaped wiring pattern, and a plurality of opening portions is arrayed in each wiring portion. The plurality of thin metal lines of at least one wiring portion of the two wiring portions is formed in a wiring pattern where the opening portions, of which angles are maintained and pitches are made to be irregular with respect to rhomboid shapes of a regular rhomboid wiring pattern, have parallelogram shapes. In the display unit, pixels, which include a plurality of sub-pixels emitting light with a plurality of colors that are at least three colors different from each other, are arrayed in pixel array patterns. The conductive film is provided on the display unit such that the wiring patterns of the two wiring portions overlap with the pixel array patterns of the display unit. From at least one point of view, the wiring patterns of the two wiring portions are formed such that an indicator of evaluation of moirés is equal to or less than an evaluation threshold value, where in frequencies and intensities of the moirés of respective colors of a plurality of colors calculated from a first peak frequency and a first peak intensity of a plurality of first spectrum peaks of two-dimensional Fourier spectra of image data of the wiring patterns of the two wiring portions overlapping with each other and a second peak frequency and a second peak intensity of a plurality of second spectrum peaks of two-dimensional Fourier spectra of luminance image data of the pixel array patterns of the respective colors when light beams with the plurality of colors are respectively emitted, the indicator of evaluation is calculated from evaluation values of the moirés of the respective colors obtained by applying human visual response characteristics in accordance with an observation distance to intensities of the moirés equal to or greater than a first intensity threshold value among intensities of the moirés at frequencies of the moirés equal to or less than a frequency threshold value defined on the basis of a display resolution of the display unit.

Further, in order to achieve the object, according to a second aspect of the present invention, there is provided a conductive film that is provided on a display unit of a display device, the conductive film comprising: a first transparent substrate; a first wiring portion that is formed on one side of the first transparent substrate and has a plurality of thin metal lines; a second transparent substrate that is disposed on the first wiring portion; and a second wiring portion that is formed on one side of the second transparent substrate and has a plurality of thin metal lines. The plurality of thin metal lines has a mesh-shaped wiring pattern, and a plurality of opening portions is arrayed in each wiring portion. The plurality of thin metal lines of at least one wiring portion of two wiring portions including the first wiring portion and the second wiring portion is formed in a wiring pattern where the opening portions, of which angles are maintained and pitches are made to be irregular with respect to rhomboid shapes of a regular rhomboid wiring pattern, have parallelogram shapes. In the display unit, pixels, which include a plurality of sub-pixels emitting light with a plurality of colors that are at least three colors different from each other, are arrayed in pixel array patterns. The conductive film is provided on the display unit such that the wiring patterns of the two wiring portions overlap with the pixel array patterns of the display unit. From at least one point of view, the wiring patterns of the two wiring portions are formed such that an indicator of evaluation of moirés is equal to or less than an evaluation threshold value, where in frequencies and intensities of the moirés of respective colors of a plurality of colors calculated from a first peak frequency and a first peak intensity of a plurality of first spectrum peaks of two-dimensional Fourier spectra of image data of the wiring patterns of the two wiring portions overlapping with each other and a second peak frequency and a second peak intensity of a plurality of second spectrum peaks of two-dimensional Fourier spectra of luminance image data of the pixel array patterns of the respective colors when light beams with the plurality of colors are respectively emitted, the indicator of evaluation is calculated from evaluation values of the moirés of the respective colors obtained by applying human visual response characteristics in accordance with an observation distance to intensities of the moirés equal to or greater than a first intensity threshold value among intensities of the moirés at frequencies of the moirés equal to or less than a frequency threshold value defined on the basis of a display resolution of the display unit.

Furthermore, in order to achieve the object, according to a third aspect of the present invention, a display device comprises: a display unit in which pixels, which include a plurality of sub-pixels emitting light with a plurality of colors that are different from each other, are arrayed in pixel array patterns which are repeated in a certain direction and a direction perpendicular to the certain direction; and the conductive film according to the first or second aspect, the conductive film being provided on the display unit.

In addition, in order to achieve the object, according to a fourth aspect of the present invention, there is provided a method of evaluating a conductive film that is provided on a display unit of a display device and has two wiring portions which are respectively formed on both sides of a transparent substrate and each of which has a plurality of thin metal lines, where the plurality of thin metal lines has a mesh-shaped wiring pattern and a plurality of opening portions is arrayed in the wiring portions. The method comprises: forming the plurality of thin metal lines of at least one wiring portion of two wiring portions in a wiring pattern where the opening portions, of which angles are maintained and pitches are made to be irregular with respect to rhomboid shapes of a regular rhomboid wiring pattern, have parallelogram shapes; arraying pixels, which include a plurality of sub-pixels emitting light with a plurality of colors that are at least three colors different from each other, in pixel array patterns, in the display unit; providing the conductive film on the display unit such that the wiring patterns of the two wiring portions overlap with the pixel array patterns of the display unit; acquiring image data of the wiring patterns of the two wiring portions overlapping with each other and luminance image data of the pixel array patterns of respective colors of the plurality of colors of the display unit, from at least one point of view; calculating a first peak frequency and a first peak intensity of a plurality of first spectrum peaks of two-dimensional Fourier spectra of image data of the regular rhomboid wiring pattern and a second peak frequency and a second peak intensity of a plurality of second spectrum peaks of two-dimensional Fourier spectra of luminance image data of the pixel array patterns of the respective colors of the plurality of colors, for each color, by performing two-dimensional Fourier transform on the image data of the regular rhomboid wiring pattern and the luminance image data of the pixel array pattern; calculating frequencies and intensities of moirés of the respective colors of the plurality of colors from the first peak frequency and the first peak intensity of the wiring pattern and the second peak frequency and the second peak intensity of the sub-pixel array patterns of the respective plurality of colors calculated in the above-mentioned manner; selecting moirés having frequencies equal to or less than a frequency threshold value and intensities equal to or greater than a first intensity threshold value defined on the basis of a display resolution of the display unit, among the frequencies and intensities of the moirés of the respective colors calculated in the above-mentioned manner; acquiring evaluation values of the moirés of the respective colors by applying human visual response characteristics in accordance with an observation distance to the intensities of the moirés at respective frequencies of the moirés of the respective colors selected in the above-mentioned manner; calculating an indicator of evaluation of the moirés from the evaluation values of the moirés of the respective colors acquired in the above-mentioned manner; and evaluating the conductive film of which the indicator of evaluation of the moirés calculated in the above-mentioned manner is equal to or less than a predetermined value.

In addition, in order to achieve the object, according to a fifth aspect of the present invention, there is provided a method of evaluating a conductive film that is provided on a display unit of a display device and has a first transparent substrate, a first wiring portion that is formed on one side of the first transparent substrate and has a plurality of thin metal lines, a second transparent substrate that is disposed on the first wiring portion, and a second wiring portion that is formed on one side of the second transparent substrate and has a plurality of thin metal lines, where the plurality of thin metal lines has a mesh-shaped wiring pattern and a plurality of opening portions is arrayed in the wiring portions. The method comprises: forming the plurality of thin metal lines of at least one wiring portion of two wiring portions including the first wiring portion and the second wiring portion in a wiring pattern where the opening portions, of which angles are maintained and pitches are made to be irregular with respect to rhomboid shapes of a regular rhomboid wiring pattern, have parallelogram shapes; arraying pixels, which include a plurality of sub-pixels emitting light with a plurality of colors that are at least three colors different from each other, in pixel array patterns, in the display unit; providing the conductive film on the display unit such that the wiring patterns of the two wiring portions overlap with the pixel array patterns of the display unit; acquiring image data of the wiring patterns of the two wiring portions overlapping with each other and luminance image data of the pixel array patterns of respective colors of the plurality of colors of the display unit, from at least one point of view; calculating a first peak frequency and a first peak intensity of a plurality of first spectrum peaks of two-dimensional Fourier spectra of image data of the regular rhomboid wiring pattern and a second peak frequency and a second peak intensity of a plurality of second spectrum peaks of two-dimensional Fourier spectra of luminance image data of the pixel array patterns of the respective colors of the plurality of colors, for each color, by performing two-dimensional Fourier transform on the image data of the regular rhomboid wiring pattern and the luminance image data of the pixel array pattern; calculating frequencies and intensities of moirés of the respective colors of the plurality of colors from the first peak frequency and the first peak intensity of the wiring pattern and the second peak frequency and the second peak intensity of the sub-pixel array patterns of the respective plurality of colors calculated in the above-mentioned manner; selecting moirés having frequencies equal to or less than a frequency threshold value and intensities equal to or greater than a first intensity threshold value defined on the basis of a display resolution of the display unit, among the frequencies and intensities of the moirés of the respective colors calculated in the above-mentioned manner; acquiring evaluation values of the moirés of the respective colors by applying human visual response characteristics in accordance with an observation distance to the intensities of the moirés at respective frequencies of the moirés of the respective colors selected in the above-mentioned manner; calculating an indicator of evaluation of the moirés from the evaluation values of the moirés of the respective colors acquired in the above-mentioned manner; and evaluating the conductive film of which the indicator of evaluation of the moirés calculated in the above-mentioned manner is equal to or less than a predetermined value.

In any one aspect of the first to fifth aspects, it is preferable that the evaluation threshold value is −2.80, and the indicator of evaluation is equal to or less than −2.80 as a common logarithm.

Further, it is preferable that a predetermined range of the irregularity is greater than 0% and equal to or less than 10%.

It is preferable that the luminance image data of the pixel array patterns of the respective colors is normalized luminance image data that is obtained by normalizing the luminance image data obtained by converting captured image data of the colors, which is obtained by capturing images of the pixel array patterns of the respective colors displayed on a display screen of the display unit, into luminance values, when the light beams with the plurality of colors are separately emitted.

Further, it is preferable that images of the pixel array patterns of the respective colors displayed on the display screen of the display unit are displayed on the display unit when the light beams with the plurality of colors are separately emitted at a maximum intensity which can be set for each color.

Furthermore, it is preferable that when the plurality of colors is three colors such as red, green, and blue, the captured image data of the images of the pixel array patterns of the respective colors such as red, green, and blue is image data that is obtained by imaging after adjusting white balance to a white color of a Macbeth chart.

It is preferable that the luminance image data of the images of the pixel array patterns of the respective colors of the plurality of colors is data that is obtained by giving the luminance image data in which a measured luminance value is normalized through a product between a resolution of the display unit and an area having a value of a mask image, where the mask image is created from the captured image data which is obtained by capturing the image of the pixel array pattern of a current color displayed on the display screen of the display unit through a microscope, when the light beams of the respective colors of the plurality of colors are separately emitted in the display unit, and the luminance image data is obtained by normalizing a luminance of a display unit of a reference display device to 1.0.

Further, it is preferable that, when the plurality of colors is three colors such as red, green, and blue, the measured luminance value is a luminance value which is obtained from spectrum data of each color of red, green, and blue by separately performing display for each color of red, green, and blue and performing measurement through a spectrometer, and the mask image is an image that is obtained by binarizing the captured image data which is obtained through imaging of the microscope.

It is preferable that both the pluralities of thin metal lines of the two wiring portions constitute the irregular parallelogram wiring pattern.

Alternatively, it is preferable that the plurality of thin metal lines of one wiring portion of the two wiring portions constitutes the irregular parallelogram wiring pattern, and the plurality of thin metal lines of another wiring portion constitutes the regular rhomboid wiring pattern.

Alternatively, it is preferable that at least one wiring portion of the two wiring portions includes an electrode portion and a non-electrode portion, the plurality of thin metal lines of one of the electrode portion and the non-electrode portion constitutes the irregular parallelogram wiring pattern, and the plurality of thin metal lines of another of the electrode portion and the non-electrode portion constitutes the regular rhomboid wiring pattern.

It is preferable that the plurality of first spectrum peaks has a peak intensity that is equal to or greater than a first threshold value which is selected from a plurality of spectrum peaks obtained by performing two-dimensional Fourier transform on the image data of the wiring pattern, and for each of the plurality of colors, the plurality of second spectrum peaks has a peak intensity that is equal to or greater than a second threshold value which is selected from a plurality of spectrum peaks obtained by performing two-dimensional Fourier transform on the luminance image data of the pixel array pattern.

Further, it is preferable that a frequency of a moiré corresponding to each color is given as a difference between the first peak frequency and the second peak frequency corresponding to each color, and an intensity of the moiré corresponding to each color is given as a product between the first peak intensity and the second peak intensity corresponding to each color.

It is preferable that an evaluation value of the moiré is calculated by weighting a visual transfer function, which corresponds to the observation distance as the visual response characteristics, to the frequency and the intensity of the moiré through convolution integration.

Further, it is preferable that the visual transfer function VTF is given by the following Expression (1).

$$\mathrm{VTF}=5.05e^{-0.138k}(1-e^{0.1k}) \qquad (1)$$

$$k=\pi du/180$$

Here, k is a spatial frequency (cycle/deg) defined by a solid angle, u shown in the above-mentioned Expression (1) is a spatial frequency (cycle/mm) defined by a length, and d is defined by an observation distance (mm).

It is preferable that the indicator (quantitative value) of evaluation of the moirés is calculated using a largest evaluation value among the evaluation values of the plurality of the moirés in which a frequency of one of the moirés is weighted in accordance with the observation distance for each color.

Further, it is preferable that the indicator (quantitative value) of evaluation of the moirés is a largest sum among sums for the plurality of colors, the sums being obtained by adding the largest evaluation values of the frequencies of all the moirés for each color, each of the largest evaluation value being selected with respect to the frequency of one of the moirés for each color.

Furthermore, it is preferable that the first intensity threshold value is −4.5 as a common logarithm, and the frequency threshold value is a spatial frequency which is obtained from the resolution of the display unit, and a moiré, which is selected in order to apply the visual response characteristics, has an intensity which is equal to or greater than −3.8.

It is preferable that assuming that a display pixel pitch of the display unit is Pd μm, the spatial frequency obtained from the resolution of the display unit is a highest frequency of the moirés which is given as 1000/Pd cycle/mm.

Further, it is preferable that, from at least two points of view of front observation and oblique observation, the evaluation value is obtained for each color of the plurality of colors, and the indicator (quantitative value) of evaluation is a largest evaluation value among evaluation values of respective colors obtained in the at least two points of view.

Furthermore, it is preferable that the pixel array patterns are the black matrix patterns.

As described above, according to the present invention, there is provided a conductive film having the random mesh-shaped wiring pattern (mesh pattern) corresponding to the intensity of the display regardless of the observation distance, even in a case where the pattern overlaps with the pixel array pattern of a display unit (display) having a different emission intensity (luminance). Thereby, it is possible to prevent moiré from occurring, and it is possible to greatly improve visibility.

In particular, according to the present invention, the conductive film has a random mesh pattern in which the emission intensity of the display unit is considered, when the conductive film overlaps with a black matrix of a display unit of a display device having a different emission intensity and is visually perceived, in a case where the transparent conductive film having the mesh pattern is used as a touch panel electrode. Thereby, it is possible to suppress occurrence of moiré which greatly disturbs image quality, and it is possible to greatly improve visibility of the display on the touch panel.

Further, according to the present invention, in addition to the above-mentioned object, also in a design of a mesh pattern of the conductive film in a case where the opening shapes of the RGB sub-pixels of the display have frequencies and intensities (shapes and sizes) different from each other, it is possible to provide best image quality in combination with the pixel array pattern of a display having a different emission intensity.

BRIEF DESCRIPTION OF THE DRAWINGS

FIG. 11A is a schematic diagram illustrating an example of a structure of the mesh wiring pattern shown in FIG. 2, FIG. 11B is a schematic diagram illustrating an example of a structure of the pixel array pattern of the display unit shown in FIG. 9, FIG. 11C is an example of a graph of a transmittance (T) of the mesh wiring pattern in the present invention, FIG. 11D is an example of a graph of an intensity (I) of a representative sub-pixel of the display unit, and FIGS. 11E and 11F are examples of graphs of transmittances (T) of the representative sub-pixels of the mesh wiring pattern and the display unit in the related arts.

FIG. 12(B) is a partially enlarged view of the pixel array patterns of FIG. 12(A).

Figure 1:
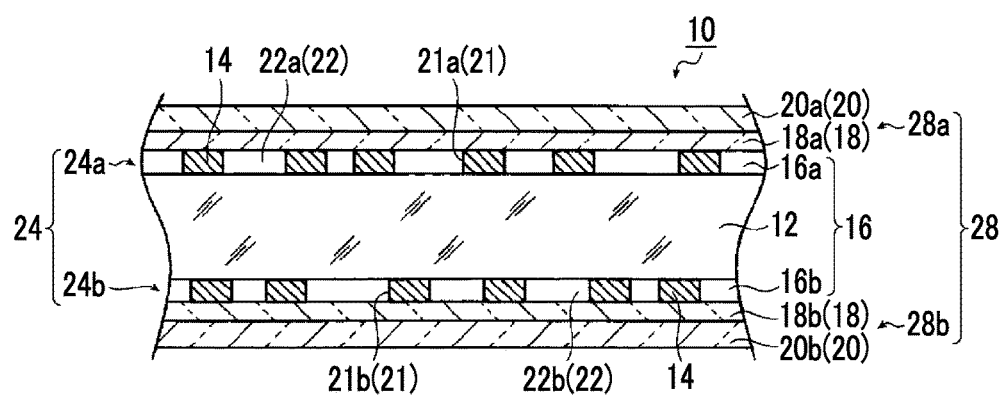
FIG. 1 is a partial cross-sectional view schematically illustrating an example of a conductive film according to a first embodiment of the present invention.

DESCRIPTION OF THE PREFERRED
EMBODIMENTS

Hereinafter, a conductive film according to the present invention, a display device having the same, and a method of evaluating the conductive film will be described in detail with reference to most preferred embodiments shown in the accompanying drawings.

In the following description, a conductive film for a touch panel will be explained as a representative example of the conductive film according to the present invention, but the present invention is not limited to this example. The conductive film has wiring portions where at least one of wiring patterns disposed on both sides of a transparent substrate is a wiring pattern having parallelogram shapes of which angles are maintained and pitches are made to be irregular. The conductive film according to the present invention may be of any type as long as it is a conductive film provided on a display unit of a display device such as a liquid crystal display (LCD), a plasma display panel (PDP), an organic electroluminescence display (OELD), or an inorganic EL display. It is needless to say that the conductive film according to the present invention may be, for example, a conductive film for electromagnetic shields.

As described in detail later, in the display unit (hereinafter also referred to as a display) of the display device overlapping with the conductive film of the present invention, pixels, which include a plurality of sub-pixels emitting light with a plurality of colors including at least three mutually different colors, for example, three colors such as red, green, and blue, are arrayed in pixel array patterns (hereinafter referred to as BM patterns). The display unit is not particularly limited as long as it is a display unit in which a luminance (brightness) of each sub-pixel (color filter) depending on an emission intensity (luminance) thereof can be considered for evaluation of visibility of moiré caused by overlapping of the conductive film. For example, in a manner similar to that of the related art, the display unit may be a display unit in which cycles of repetition and intensities (shapes and sizes) of sub-pixels (color filters), that is, sub-pixel array patterns (shapes, sizes, and cycles of the sub-pixels) may be all the same for the plurality of colors such as RGB, and which has a BM pattern which can be typified by a G sub-pixel. In a manner similar to that of the above-mentioned OELD, the display unit may be a display unit having a BM pattern including sub-pixel array patterns which are not all the same for the plurality of colors, that is, which are different for at least two colors.

In a manner similar to that of a high resolution smartphone, a tablet terminal, or the like, the display of the display device subjected to the present invention may be a display which has a high emission intensity. In a manner similar to that of a low resolution desktop PC, a television (TV), or the like, the display may be a display having a low emission intensity. In a manner similar to that of a medium resolution laptop or the like, the display may be a display having approximately a medium emission intensity.

Figure 2:
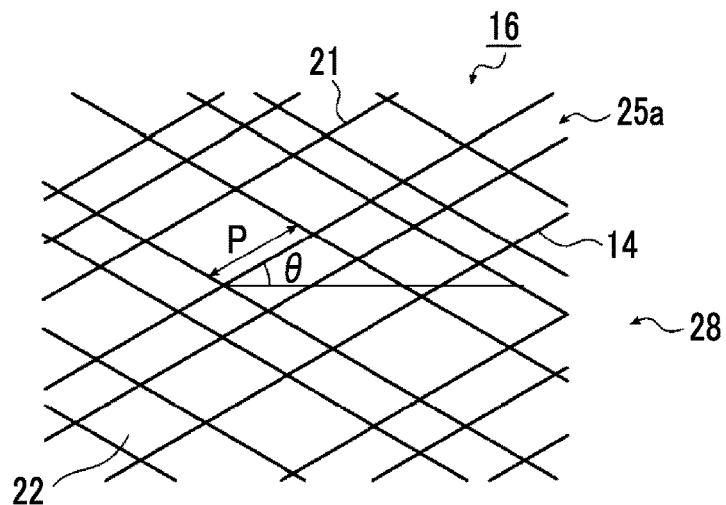
FIG. 2 is a plan view schematically illustrating an example of an irregular ng pattern of a wiring portion of the conductive film shown in FIG. 1.

FIG. 1 is a partial cross-sectional view schematically illustrating an example of a conductive film according to a first embodiment of the present invention. FIG. 2 is a plan view schematically illustrating an example of an irregular wiring pattern of a wiring portion of the conductive film shown in FIG. 1.

As shown in the drawings, a conductive film 10 of the present embodiment is a conductive film that is provided on the display unit of the display device and that has a wiring pattern which is excellent in terms of suppression of occurrence of moiré in the black matrix (BM) of the display unit, particularly, a wiring pattern which is optimized in terms of visibility of moiré in the BM pattern when the wiring pattern overlaps with the BM pattern. The conductive film 10 has: a transparent substrate 12; a first wiring portion 16a that is formed on one surface (an upper surface in FIG. 1) of the transparent substrate 12, is formed of a plurality of thin lines made of metal (hereinafter referred to as thin metal lines) 14, and functions as a first electrode portion; a first protective layer 20a that is bonded to substantially the entire surface of the first wiring portion 16a through a first adhesive layer 18a so as to cover the thin metal lines 14; a second wiring portion (electrode) 16b that is formed on the other surface (a lower surface in FIG. 1) of the transparent substrate 12, is formed of a plurality of thin metal lines 14, and functions as a second electrode portion; and a second protective layer 20b that is bonded to substantially the entire surface of the second wiring portion 16b through a second adhesive layer 18b.

Hereinafter, the first wiring portion 16a and the second wiring portion 16b are collectively referred to as simply wiring portions 16, the first adhesive layer 18a and the second adhesive layer 18b are collectively referred to as simply adhesive layers 18, and the first protective layer 20a and the second protective layer 20b are collectively referred to as simply protective layers 20.

The transparent substrate 12 is formed of a material having an insulation property and having a high light-permeability, and examples thereof include a resin, glass, and silicon. Examples of the resin include polyethylene terephthalate (PET), polymethyl methacrylate (PMMA), polypropylene (PP), polystyrene (PS), and the like.

The thin metal lines 14 are not particularly limited as long as they are thin lines made of metal having high conductivity, and include thin lines made of a line material such as gold (Au), silver (Ag) or copper (Cu). While it is more preferable indeed in terms of visibility if the thin metal lines 14 have a smaller line width, the line width has only to be 30 μm or less, for instance. For application to a touch panel, the line width of the thin metal lines 14 is preferably equal to or greater than 0.1 μm and equal to or less than 15 μm, more preferably equal to or greater than 1 μm and equal to or less than 9 μm, and still more preferably equal to or greater than 2 μm and equal to or less than 7 μm.

Each wiring portion 16 (16a, 16b) has a plurality of thin metal lines 14 having a wiring pattern 24 (24a, 24b) which is formed of mesh wires 21 (21a, 21b) arrayed in a mesh shape. Specifically, as shown in FIG. 2, the wiring pattern 24 (24a, 24b) is a mesh pattern in which opening portions (cells) 22 (22a, 22b) are arrayed in a predetermined shape formed by intersecting the plurality of thin metal lines 14 with each other.

As shown in FIG. 2, each wiring portion 16 (16a, 16b) is formed of the thin metal lines 14 and a wiring layer 28 (28a, 28b) that has a wiring pattern 24 (24a, 24b) formed in a mesh shape by the opening portions (cells) 22 (22a, 22b) between the thin metal lines 14 adjacent to each other. In plan view, the wiring pattern 24 is an irregular wiring pattern, so called, a random pattern 25 where the opening portions 22 are multiply connected in two directions between which a predetermined angle is formed. The opening portions 22 have parallelogram shapes of which the predetermined angles are maintained and pitches (that is, sizes) are different, in plan view.

In the example shown in FIG. 1, the wiring patterns 24 have, as the wiring patterns 24a and 24b, irregular parallelogram wiring patterns, so called, random patterns 25a in which the mesh shapes of the opening portions 22 have the same angles and only the pitches thereof are different as shown in FIG. 2.

Figure 3:
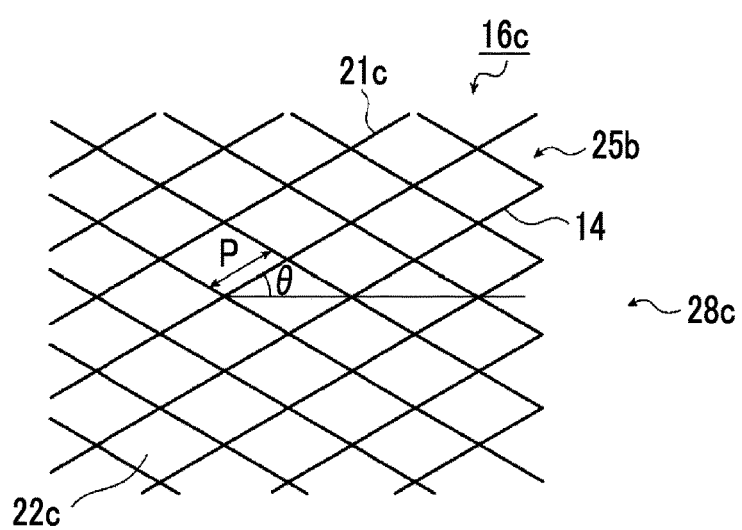
FIG. 3 is a plan view schematically illustrating a regular rhomboid wiring pattern before the wiring pattern shown in FIG. 2 is made to be irregular.

Here, in the irregular wiring pattern (random pattern) 25a shown in FIG. 2, pitches thereof are made to be irregular (random) in a predetermined range, with angles thereof maintained, with respect to pitches of rhomboid shapes of opening portions 22c of a regular rhomboid wiring pattern, so called, a uniform pattern 25b in which the multiple opening portions 22c having the same rhomboid shapes are regularly repeated as shown in FIG. 3.

Here, in the random pattern 25a, the predetermined range of the irregularity applied to the rhomboid shapes of the opening portions 22c of the wiring pattern 25b with angles maintained is preferably greater than 0% and equal to or less than 10%, more preferably in a range of 2% to 10%, and yet more preferably in a range 2% to 8%.

Further, in the random pattern 25a, the irregularity applied to the pitches of the rhomboid shapes of the opening portions 22c of the regular wiring pattern 25b are not particularly limited, and may be any form as long as the irregularity satisfies the above-mentioned range. For example, a distribution in the irregularity may be a normal distribution, and may be a uniform distribution.

The wiring portion 16c shown in FIG. 3 is formed of the thin metal lines 14 and a wiring layer 28c that has a wiring pattern 25b formed in a mesh shape by the opening portions (cells) 22c between adjacent thin metal lines 14.

As will be described in detail later, the conductive film 10 of the present invention has a wiring pattern having parallelogram shapes of which only pitches are made to be irregular (random) (angles are maintained) with respect to the rhomboid shape of the regular rhomboid wiring pattern, and has a wiring pattern which is optimized in terms of moiré visibility with respect to a predetermined luminance (luminance image data) of the BM pattern of the display unit. In the present invention, the wiring pattern, which is optimized in terms of moiré visibility with respect to the BM pattern with the predetermined luminance, is defined as a wiring pattern making moiré not perceived by human visual sensation with respect to the BM pattern with the predetermined luminance.

Accordingly, the wiring pattern 24 (24a, 24b) has a randomized parallelogram wiring pattern 25a, is a wiring pattern that is optimized in terms of moiré visibility with respect to the predetermined luminance (luminance image data) of the BM pattern of the display unit, and is a wiring pattern which allows an indicator of evaluation of moiré to be equal to or less than a predetermined evaluation threshold value. The indicator is calculated from synthetic image data of the combined wiring pattern 24, in which (transmittance image data of) the wiring patterns 24a and 24b overlap with each other, and luminance image data of the BM pattern of each color obtained when light beams with the plurality of colors of the display are respectively emitted. That is, the wiring pattern 24 is a wiring pattern including a randomized parallelogram wiring pattern which is superimposed on a display screen of the display with a predetermined emission intensity, is able to sufficiently prevent moiré from occurring and to improve visibility, and is optimized in terms of moiré visibility with respect to the BM pattern with the predetermined luminance of the display unit.

In the present invention, as described above, the regular rhomboid wiring (mesh) pattern is made to be irregular in a predetermined manner, and the parallelogram wiring pattern, which is optimized in terms of moiré visibility with respect to the BM pattern with the predetermined luminance of the display unit, is used. Thereby, it is possible to generate a robust wiring pattern.

In the parallelogram wiring (mesh) pattern 25a included in such an optimized wiring pattern, disconnections (brakes) may be inserted into a side (mesh wires 21) of the thin metal lines 14 constituting the opening portions 22. Accordingly, it is apparent that, in the wiring (mesh) pattern 25b which is not made to irregular, disconnections (brakes) may be inserted into a side (mesh wires 21c) of the thin metal lines 14 constituting the opening portions 22c. As the shape of the mesh-shaped wiring pattern having such breaks, it is possible to employ a shape of a mesh-shaped wiring pattern of a conductive film described in JP2012-276175 relating to the present application of the applicants.

Figure 4:
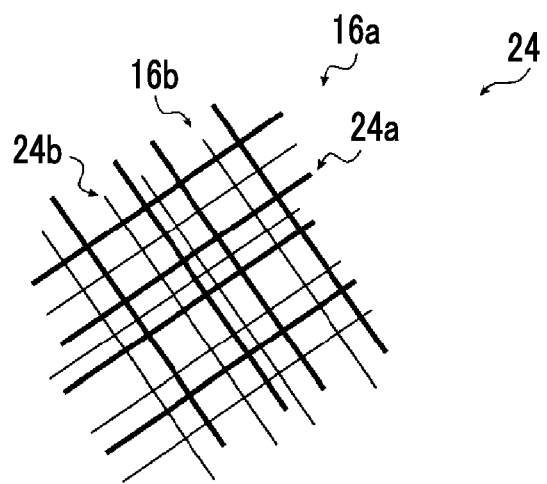
FIG. 4 is a plan view schematically illustrating an example of a combined wiring pattern which is combined by overlapping the upper and lower wiring patterns of the wiring portions of the conductive film shown in FIG. 1.
Figure 5:
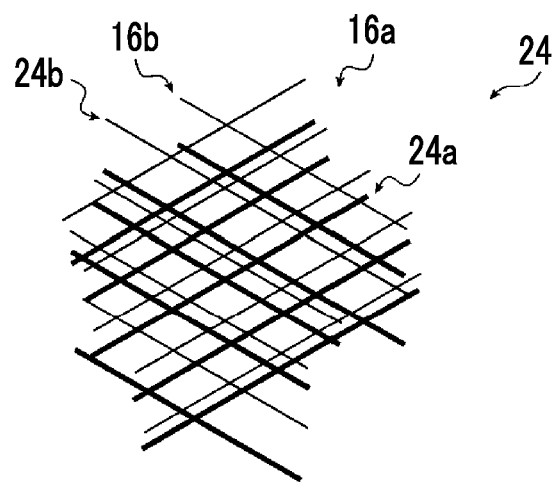
FIG. 5 is a plan view schematically illustrating an example of a combined wiring pattern which is combined by overlapping the upper and lower wiring patterns of the wiring portions of the conductive film according to another embodiment of the present invention.

In the conductive film 10 of the embodiment shown in FIG. 1, in FIG. 1, the plurality of thin metal lines 14 of the first wiring portion 16a on the upper side (viewing side) of the transparent substrate 12, and the plurality of thin metal lines 14 of the second wiring portion 16b on the lower side (display side), respectively have, as the wiring patterns 24a and 24b, the irregular wiring patterns 25a shown in FIG. 2. As shown in FIG. 4, the combined wiring pattern 24, which is made to be irregular by overlapping the irregular wiring patterns 24a and 24b on the upper and lower sides, is formed. In FIG. 4 and FIG. 5 to be described later, in order to facilitate understanding, the plurality of thin metal lines 14 constituting the upper wiring pattern 24a is indicated by the heavy lines, and the plurality of thin metal lines 14 constituting the lower wiring pattern 24b is indicated by the thin lines. Here, it is needless to say that widths of the heavy lines and the thin lines may not be real line widths of the thin metal lines 14, may be equal thereto, and may be different therefrom.

That is, in the example shown in FIG. 1, the first and second wiring portions 16a and 16b each are formed of a plurality of thin metal lines having such an irregular wiring pattern 25a shown in FIG. 2. However, the present invention is not limited to this, at least a part of either one wiring portion 16 thereof may have a plurality of thin metal lines having the irregular wiring pattern 25a shown in FIG. 2.

As described above, the irregular (randomized) wiring pattern 25a is formed of the entirety or a part of the thin metal lines of the wiring portion 16 (wiring portion 16a or 16b) on the upper or lower side of the conductive film, and the mesh-shaped wiring pattern, in which the wiring patterns of both wiring portions 16 overlaps and are combined, is randomized. As a result, it is possible to randomize the light transmitted through the mesh-shaped wiring pattern, and it is possible to improve visibility of moiré which is caused by interference between the display and the regular wiring pattern.

For example, as shown in FIG. 5, the first and second wiring portions 16a and 16b each are formed of a plurality of thin metal lines having a different wiring pattern. In the example shown in FIG. 5, the first wiring portion 16a on the upper side of the transparent substrate 12 is formed of the plurality of thin metal lines 14 having the irregular wiring pattern 25a shown in FIG. 2, and the second wiring portion 16b on the lower side of the transparent substrate 12 is formed of the plurality of thin metal lines 14 having the regular wiring pattern 25b shown in FIG. 3. On the contrary, the first wiring portion 16a may be formed of a plurality of thin metal lines 14 having the regular wiring pattern 25b shown in FIG. 3, and the second wiring portion 16b may be formed of the plurality of thin metal lines 14 having the irregular wiring pattern 25a. In such a manner, the combined wiring pattern, in which the irregular wiring pattern 25a and the regular wiring pattern 25b overlap with each other, can be made to be irregular.

Figure 6:
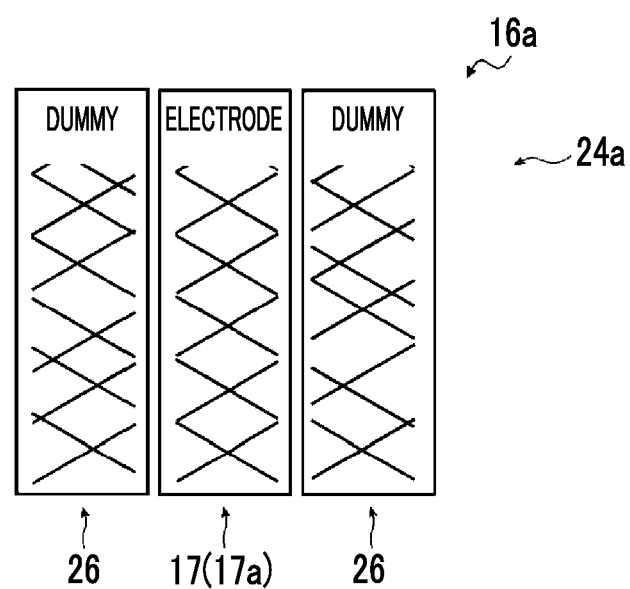
FIG. 6 is a plan view schematically illustrating an example of the upper wiring pattern of the wiring portion of the conductive film according to another embodiment of the present invention.

Alternatively, as shown in FIG. 6, the plurality of thin metal lines 14 of either one of the first or second wiring portions 16a and 16b may be divided into dummy electrode portions (non-electrode portions) 26 and the electrode portion 17 constituting the wiring layer 28, by using the disconnections (brakes), as described above. Then, either one of the electrode portion 17 or the dummy electrode portion 26 may be formed of the plurality of thin metal lines 14 having the irregular wiring pattern 25a shown in FIG. 2, and the other one may be formed of the plurality of thin metal lines 14 having the regular wiring pattern 25b shown in FIG. 3. Such a configuration may be applied to the conductive film 11 of a second embodiment of the present invention shown in FIG. 7 to be described later. In such a manner, it is possible to make irregular the combined wiring pattern in which a combination between the irregular wiring pattern 25a and the regular wiring pattern 25b overlaps with the wiring pattern 25a or wiring pattern 25b.

In FIG. 6, the first wiring portion 16a on the upper side of the transparent substrate 12 is divided into an electrode portion 17a and two dummy electrode portions 26 on the right and left sides thereof, by using disconnections (brakes). The two dummy electrode portions 26 each are formed of the plurality of thin metal lines 14 having the irregular wiring pattern 25a shown in FIG. 2. The electrode portion 17a is formed of the plurality of thin metal lines 14 having the regular wiring pattern 25b shown in FIG. 3. However, it is apparent that a configuration opposite to the above-mentioned configuration may be adopted.

A structure of the conductive film 11 of the second embodiment of the present invention shown in FIG. 7 will be described below.

As described above, the first protective layer 20a is bonded to the substantially entire surface of the wiring layer 28a formed of the first wiring portion 16a through the first adhesive layer 18a so as to cover the thin metal lines 14 of the first wiring portion 16a. Further, the second protective layer 20b is bonded to the substantially entire surface of the wiring layer 28b formed of the second wiring portion 16b through the second adhesive layer 18b so as to cover the thin metal lines 14 of the second wiring portion 16b.

Here, examples of materials of the adhesive layers 18 (the first adhesive layer 18a and the second adhesive layer 18b) include a wet lamination adhesive, a dry lamination adhesive, a hot melt adhesive, and the like. The material of the first adhesive layer 18a and the material of the second adhesive layer 18b may be the same or may be different.

The protective layers 20 (the first protective layer 20a and the second protective layer 20b) each are made of a high transmissive material including resin, glass, and silicon, similarly to the transparent substrate 12. The material of the first protective layer 20a and the material of the second protective layer 20b may be the same or may be different.

It is preferable that both a refractive index n1 of the first protective layer 20a and a refractive index n2 of the second protective layer 20b are values equal or approximate to a refractive index n0 of the transparent substrate 12. In this case, both the relative refractive index nr1 of the transparent substrate 12 with respect to the first protective layer 20a and the relative refractive index nr2 of the transparent substrate 12 with respect to the second protective layer 20b are values approximate to 1.

In this specification, the refractive index means a refractive index for the light at a wavelength of 589.3 nm (sodium D ray). For example, in regard to resins, the refractive index is defined by ISO 14782: 1999 (corresponding to JIS K 7105) that is an international standard. Further, the relative refractive index nr1 of the transparent substrate 12 with respect to the first protective layer 20a is defined as nr1=(n1/n0), and the relative refractive index nr2 of the transparent substrate 12 with respect to the second protective layer 20b is defined as nr2=(n2/n0).

Here, the relative refractive index nr1 and the relative refractive index nr2 are preferably in a range equal to or greater than 0.86 and equal to or less than 1.15, and more preferably in a range equal to or greater than 0.91 and equal to or less than 1.08.

By limiting the ranges of the relative refractive index nr1 and the relative refractive index nr2 as the above-mentioned range and controlling a member-to-member light transmittance between the transparent substrate 12 and the protective layers 20 (20a, 20b), visibility of moiré can be further improved, and thus the conductive film can be improved.

In the conductive film 10 of the embodiment shown in FIG. 1, the wiring portions 16 (16a and 16b) on both the upper and lower sides of the transparent substrate 12 each are formed as an electrode portion having the plurality of thin metal lines 14. However, the present invention is not limited to this, and at least one of the first and second wiring portions 16a and 16b may be formed of an electrode portion and a non-electrode portion (dummy electrode portion).

Figure 7:
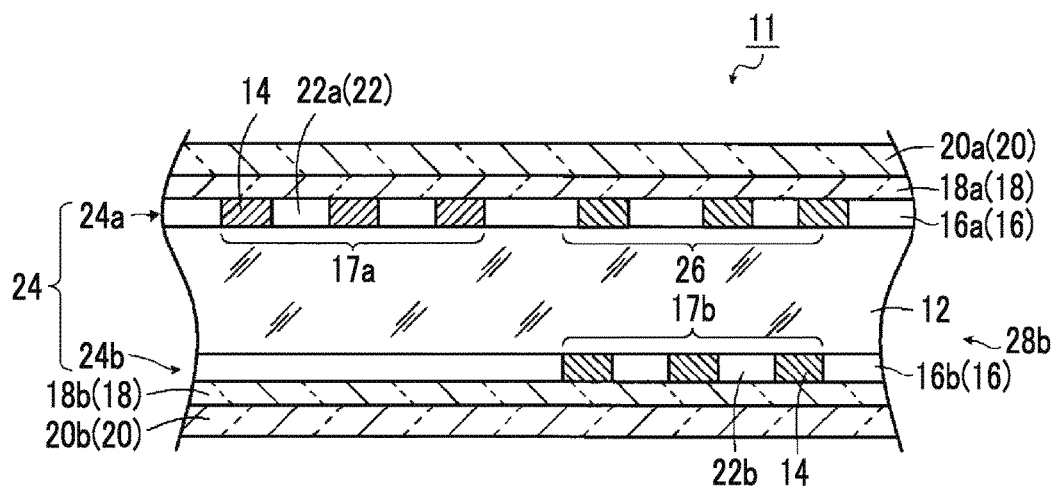
FIG. 7 is a schematic partial cross-sectional view of an example of a conductive film according to a second embodiment of the present invention.

FIG. 7 is a schematic partial cross-sectional view of an example of the conductive film according to the second embodiment of the present invention. The plan view of the wiring patterns of the conductive film according to the second embodiment shown in FIG. 7 is the same as the plan view of the wiring patterns shown in FIGS. 2 and 3, and accordingly, will be omitted herein.

As shown in the drawing, the conductive film 11 according to the second embodiment has: the first wiring portion 16a that is formed of the first electrode portion 17a and the dummy electrode portion 26 which are formed on one surface (on the upper side in FIG. 7) of the transparent substrate 12; the second wiring portion 16b that is formed of the second electrode portion 17b which is formed on the other surface (on the lower side in FIG. 7) of the transparent substrate 12; the first protective layer 20a that is bonded to the substantially entire surface of the first wiring portion 16a, which is formed of the first electrode portion 17a and the dummy electrode portion 26, through the first adhesive layer 18a; and the second protective layer 20b that is boned to the substantially entire surface of the second wiring portion 16b, which is formed of the second electrode portion 17b, through the second adhesive layer 18b.

In the conductive film 11, the first electrode portion 17a and the dummy electrode portion 26 each are formed of the plurality of thin metal lines 14 and both thereof are formed as the wiring layer 28a on one surface (on the upper side in FIG. 7) of the transparent substrate 12, and the second electrode portion 17b is formed of the plurality of thin metal lines 14 and is formed as the wiring layer 28b on the other surface (on the lower side in FIG. 7) of the transparent substrate 12. Here, the dummy electrode portion 26 is formed on one surface (on the upper side in FIG. 7) of the transparent substrate 12 similarly to the first electrode portion 17a, and has the plurality of thin metal lines 14 similarly arrayed at positions corresponding to the plurality of thin metal lines 14 of the second electrode portion 17b formed on the other surface (on the lower side in FIG. 7), as shown in the drawing.

The dummy electrode portion 26 is separated from the first electrode portion 17a by a predetermined distance, and is in the state of being electrically insulated from the first electrode portion 17a.

In the conductive film 11 according to the present embodiment, the dummy electrode portion 26 formed of the plurality of thin metal lines 14 corresponding to the plurality of thin metal lines 14 of the second electrode portion 17b formed on the other surface (on the lower side in FIG. 7) of the transparent substrate 12 is formed on one surface (on the upper side in FIG. 7) of the transparent substrate 12.

Therefore, scattering due to the thin metal lines on the one surface (on the upper side in FIG. 7) of the transparent substrate 12 can be controlled, and it is thus possible to improve visibility of electrode.

Here, the first electrode portion 17a and the dummy electrode portion 26 of the wiring layer 28a have the wiring pattern 24a having a mesh shape which is formed by the thin metal lines 14 and opening portions 22. The second electrode portion 17b of the wiring layer 28b has a wiring pattern 24b having a mesh shape which is formed by the thin metal lines 14 and opening portions 22, similarly to the first electrode portion 17a. As described above, the transparent substrate 12 is formed of an insulating material, and the second electrode portion 17b is in the state of being electrically insulated from the first electrode portion 17a and the dummy electrode portion 26.

In addition, the first and second electrode portions 17a and 17b and the dummy electrode portion 26 each can be formed of the same material as the wiring portions 16 of the conductive film 10 shown in FIG. 1 in the same manner.

The first protective layer 20a is bonded to the substantially entire surface of the wiring layer 28a formed of the first electrode portion 17a and the dummy electrode portion 26 through the first adhesive layer 18a so as to cover the thin metal lines 14 of the first electrode portion 17a and the dummy electrode portion 26 of the first wiring portion 16a.

Further, the second protective layer 20b is bonded to the substantially entire surface of the wiring layer 28b formed of the second electrode portion 17b through the second adhesive layer 18b so as to cover the thin metal lines 14 of the second electrode portion 17b of the second wiring portion 16b.

It should be noted that the first and second adhesive layers 18a and 18b and the first and second protective layers 20a and 20b of the conductive film 11 shown in FIG. 7 are those of the conductive film 10 shown in FIG. 1, and a description thereof will be omitted.

In the conductive film 11 of the present embodiment, the second wiring portion 16b having the second electrode portion 17b does not have the dummy electrode portion. However, the present invention is not limited to this, and in the second wiring portion 16b, the dummy electrode portion, which is electrically insulated from the second electrode portion 17b at a predetermined interval away from the first electrode portion 17a and is formed of the thin metal lines 14, may be disposed at a position corresponding to the first electrode portion 17a of the first wiring portion 16a.

In the conductive film 11 of the present embodiment, the dummy electrode portion 26 is provided on the first wiring portion 16a, and such a dummy electrode portion is provided on the second wiring portion 16b. Thereby, the dummy electrode portions may be disposed to correspond to respective mesh wires of the first electrode portion 17a of the first wiring portion 16a and the second electrode portion 17b of the second wiring portion 16b. Therefore, scattering due to the thin metal lines on the one surface (on the upper or lower side in FIG. 7) of the transparent substrate 12 can be controlled, and it is thus possible to improve visibility of electrode.

In the conductive films 10 and 11 of the first and second embodiments shown in FIGS. 1 and 7, the wiring portions 16 (16a and 16b) are respectively formed on both upper and lower sides of the transparent substrate 12. However, the present invention is not limited to this, and in a manner similar to that of a conductive film 11A of a third embodiment of the present invention shown in FIG. 8, the following structure may be adopted: the wiring portion 16 formed of the plurality of thin metal lines 14 may be formed on one surface (the upper surface in FIG. 8) of the transparent substrate 12, and two conductive film elements, in which the protective layers 20 are bonded to substantially the entire surfaces of the wiring portions 16 through the adhesive layers 18 so as to cover the thin metal lines 14, overlap with each other.

Figure 8:
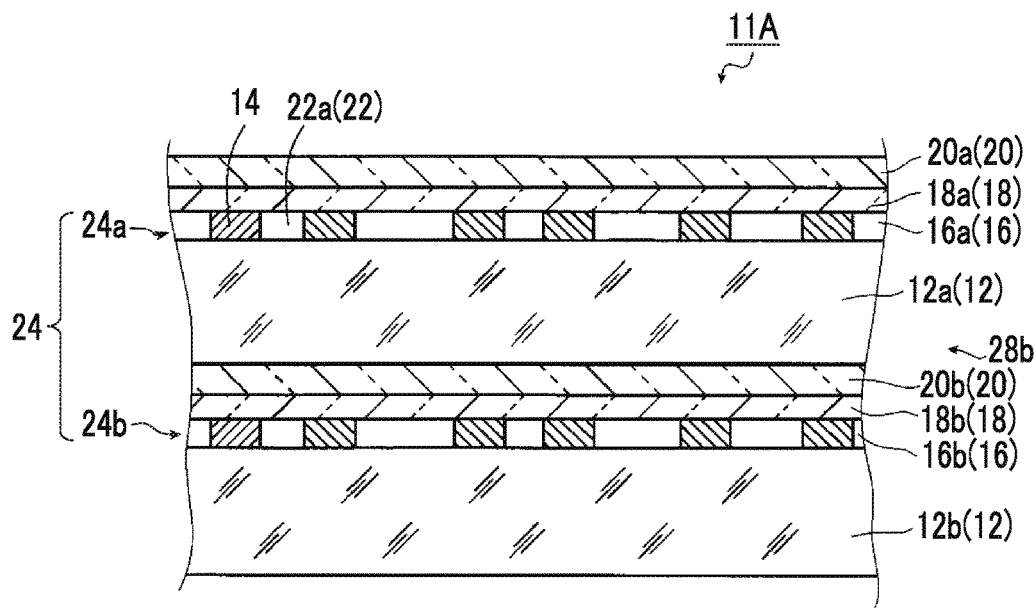
FIG. 8 is a schematic partial cross-sectional view of an example of a conductive film according to a third embodiment of the present invention.

The conductive film 11A of the third embodiment of the present invention shown in FIG. 8 has: a lower transparent substrate 12b in FIG. 8; the second wiring portion 16b that is formed of the plurality of thin metal lines 14 formed on the upper surface of the transparent substrate 12b; the second protective layer 20b that is bonded onto the second wiring portion 16b through the second adhesive layer 18b; an upper transparent substrate 12a that is bonded onto and disposed on the second protective layer 20b through for example an adhesive or the like; the first wiring portion 16a that is formed of the plurality of thin metal lines 14 formed on the upper surface of the transparent substrate 12a; and the protective layer 20a that is bonded onto the first wiring portion 16a through the adhesive layer 18a.

Here, the entirety or a part of at least one of the thin metal lines 14 of the first wiring portion 16a and/or second wiring portion 16b is the irregular wiring pattern shown in FIG. 2.

Figure 9:
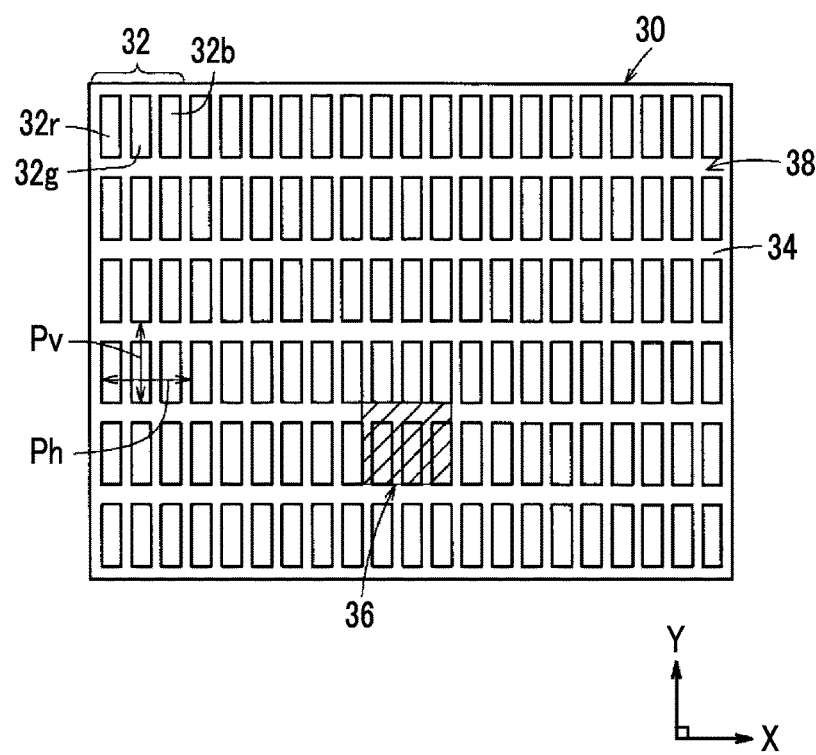
FIG. 9 is a schematic explanatory diagram illustrating an example of a pixel array pattern of a part of the display unit using the conductive film according to the present invention.

The above-mentioned conductive films 10, 11, and 11A of the first, second, and third embodiments of the present invention are applied to, for example, a touch panel (44: refer to FIG. 10) of a display unit 30 (display) schematically shown in FIG. 9. However, from at least one point of view, there is provided a wiring pattern which is optimized in terms of moiré visibility with respect to a luminance value of the pixel array (BM) pattern of each color depending on the emission intensity of the display. In the present invention, the wiring pattern, which is optimized in terms of moiré visibility with respect to the luminance value of the pixel array (BM) pattern of each color depending on the emission intensity of the display, is defined as a wiring pattern or a group of one or more wiring patterns making moiré not perceived by human visual sensation with respect to the BM pattern of the current color even when any color light beam of the light beams with respective colors of the plurality of the sub-pixels of the display is emitted alone, from at least one point of view. That is, the optimized wiring pattern is defined as a group of wiring patterns making moiré not perceived by human visual sensation with respect to a BM pattern of a color in which moiré is most likely to occur, for example, a color having a highest luminance value at the time of lighting on for each color of a plurality of colors such as RGB, that is, with respect to a BM pattern having a worst value. In the present invention, a group of two or more wiring patterns optimized may be ranked, from a wiring pattern making moiré most difficult to be perceived to a wiring pattern making moiré somewhat difficult to perceive, so as to determine one wiring pattern which makes moiré most difficult to perceive.

Here, in the present invention, in terms of optimization of moiré visibility of the wiring pattern, a reason why the luminance value of the BM pattern of each color depending on the emission intensity of the display is used is, for example, as follows. It is assumed that the conductive film has a wiring pattern with line widths and pitches of the thin metal lines shown in FIG. 11A, and the display has a BM pattern in which one pixel is typified by one sub-pixel as shown in FIG. 11A. In this case, considering one pixel of the display, transmittance image data of the wiring pattern is as shown in FIGS. 11C and 11E. In both the present invention and the related art such as JP2013-214545A, parts corresponding to the line widths of the thin metal lines do not transmit light, and thus 0 can be set, and gaps between the thin metal lines transmit light, and thus 1.0 can be set. As a result, both can be represented as binary data, and each value is completely constant. However, since the BM of the display does not transmit light, a transmittance thereof is 0, but since each sub-pixel (color filter) transmits light, an intensity of the light, for example, a luminance value thereof changes depending on the emission intensity of the display as shown in FIG. 11D. In contrast, transmittance image data of array pattern of the sub-pixels (color filters), that is, the BM pattern of the display according to the related art such as JP2013-214545A is as shown in FIG. 11F. The sub-pixel (color filter) of the display transmits light, and thus 1.0 is set. The BM of the display does not transmit light, and thus 0 is set. Therefore, the emission intensity of the display is not considered.

Meanwhile, as in a high resolution smartphone, if the emission intensity is strong, moiré visually perceived is strong, and if the emission intensity is weak, moiré visually perceived is weak. Therefore, as in the related art, indicators of evaluation of moirés obtained in displays having different emission intensities, that is, quantitative values thereof cannot be compared on the basis of the transmittance image data only. As a result, it is not possible to correctly evaluate the visibility of moiré.

Hence, in the present invention, emission intensities of different displays are evaluated and normalized on the basis of an emission intensity of a reference display. Thereby, it is possible to optimize the moiré visibility of the wiring pattern which can be applied to various displays having different emission intensities.

Next, in the present invention, the wiring pattern, which is optimized in terms of moiré visibility with respect to the BM (pixel array) pattern in a state where light with each color of the plurality of colors is emitted alone, is defined as a randomized combined wiring pattern which includes at least one of the upper and lower wiring patterns made to be irregular (that is, randomized), is randomized by overlapping the upper and lower wiring patterns, and is thereby optimized in terms of moiré visibility with respect to the luminance value of the BM pattern of each color depending on the emission intensity of the display. Here, the wiring pattern, which is made to be irregular, that is, which is randomized, is defined as a pattern in which pitches of rhomboid shapes of the above-mentioned regular rhomboid wiring pattern are made to be irregular in a predetermined manner in a predetermined direction, for example, a direction which is parallel with a side of each rhomboid of the wiring pattern and a direction perpendicular thereto.

Application of irregularity and optimization of moiré visibility of the wiring pattern, which are essential in the present invention, at the luminance value of the BM pattern of each color depending on the emission intensity of the display will be described later.

The conductive film according to the present invention basically has the above-mentioned configuration.

FIG. 9 is a schematic explanatory diagram schematically illustrating an example of a pixel array pattern of a part of the display unit using the conductive film of the present invention.

As the part thereof is shown in FIG. 9, the display unit 30 has a plurality of pixels 32 arrayed in a matrix shape to constitute a predetermined pixel array pattern. Each pixel 32 has a configuration in which three sub-pixels (a red sub-pixel 32r, a green sub-pixel 32g, and a blue sub-pixel 32b) are arrayed in a horizontal direction. Each sub-pixel has a rectangular shape which is long in the vertical direction. The arrangement pitch (horizontal pixel pitch Ph) of the pixels 32 in the horizontal direction and the arrangement pitch (vertical pixel pitch Pv) of the pixels 32 in the vertical direction are substantially equal to each other. That is, a shape (refer to a region 36 indicated by hatching), which is formed of a single pixel 32 and a black matrix (BM) 34 (pattern material) surrounding the single pixel 32, is a square shape. Further, an aspect ratio of the single pixel 32 is not 1, and satisfies the following expression: a length thereof in the horizontal (transverse) direction> a length thereof in the vertical (longitudinal) direction.

As can be clearly seen from FIG. 9, the pixel array pattern formed of the sub-pixels 32r, 32g, and 32b of each of the plurality of pixels 32 is defined by a BM pattern 38 of BMs 34 respectively surrounding the sub-pixels 32r, 32g, and 32b. Moiré, which occurs when the conductive film 10 or 11 is superposed on the display unit 30, is caused by interference between the BM pattern 38 of the BMs 34 of the display unit 30 and the wiring pattern 24 of the conductive film 10 or 11. Therefore, precisely, the BM pattern 38 is an inverted pattern of the pixel array pattern, but here, these patterns are regarded as the same patterns.

For example, the conductive film 10, 11, or 11A may be disposed on a display panel of the display unit 30 having the BM pattern 38 formed by the BMs 34. In this case, the wiring pattern 24 (a combined wiring pattern of the wiring patterns 24a and 24b) of the conductive film 10, 11, or 11A, in which at least one of the wiring patterns 24a and 24b is randomized, is optimized in terms of moiré visibility with respect to the BM (pixel array) pattern 38. Therefore, there is no interference in spatial frequency between the array cycle of the pixels 32 and the wiring array of the thin metal lines 14 of the conductive film 10, 11, or 11A, and occurrence of moiré is suppressed. As a result, the conductive film is excellent in terms of visibility of moiré. Hereinafter, the conductive film 10 will be described as a representative example, but the description is the same as those of the conductive film 11 and 11A.

It should be noted that the display unit 30 shown in FIG. 9 may be formed as a display panel such as a liquid crystal panel, a plasma panel, an organic EL panel, or an inorganic EL panel, and an emission intensity thereof may be different in accordance with a resolution.

The BM pattern and the emission intensity of the display, which can be applied to the present invention, is not particularly limited, and may be the same as the BM pattern and the emission intensity of a known display. For example, as shown in FIGS. 12(A), 12(B), 13A, 13B, and 13C, a display such as OELD having different cycles and intensities of the respective colors of RGB may be used. A display, which is formed of RGB sub-pixels having the same shapes as shown in FIG. 9 or FIGS. 14A and 14B and in which an intensity variation of the sub-pixels is large, or a display, in which an intensity variation of the sub-pixels is small and only a G sub-pixel (channel) having a highest intensity is considered, may be used. In particular, a display such as a smartphone or a tablet having a high intensity may be used.

Figure 12:
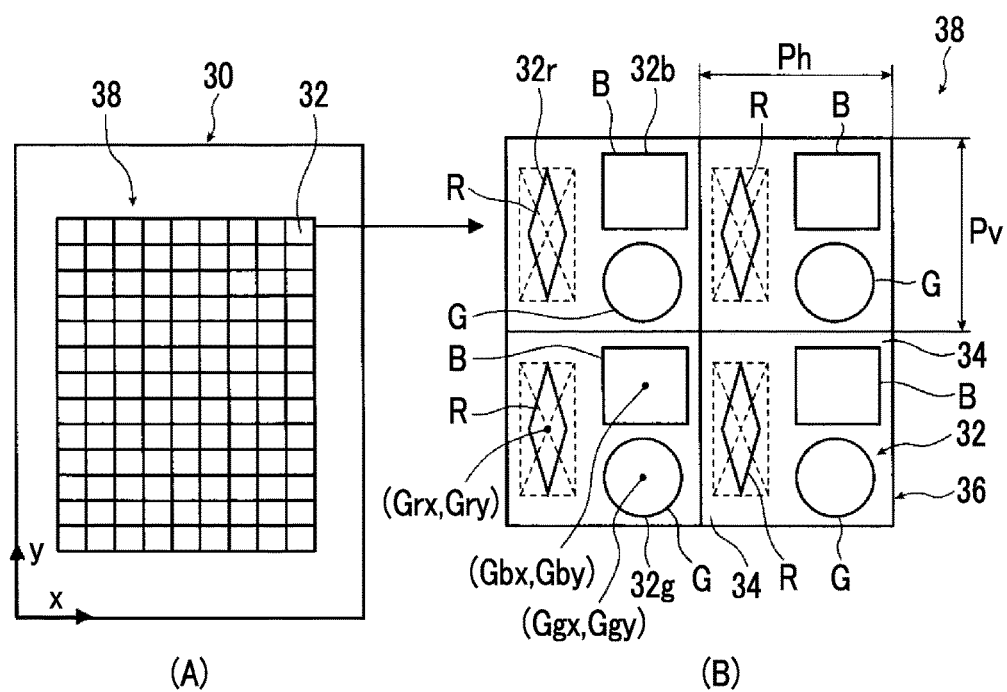
FIGS. 12(A) and 12(B) are respectively schematic explanatory diagrams illustrating an example of a part of pixel array patterns of a display using the conductive film according to the present invention.

FIGS. 12(A) and 12(B) are respectively a schematic explanatory diagram illustrating an example of a part of pixel array patterns of a display unit using the conductive film according to the present invention, and a partially enlarged view of the part.

As shown in FIG. 12(A), the display unit 30 has a plurality of pixels 32 arrayed in a matrix shape to constitute a predetermined pixel array pattern. As shown in FIG. 12(A), each pixel 32 has a configuration in which three sub-pixels (a red sub-pixel 32r, a green sub-pixel 32g, and a blue sub-pixel 32b) are arrayed in a horizontal direction.

In the present invention, it is necessary for the pixel array pattern of the display unit to satisfy any of the following three conditions: a condition in which at least two sub-pixels among a plurality of sub-pixels in a single pixel, the three sub-pixels in the example shown in the drawing, have different shapes; a condition in which cycles of sub-pixel array patterns formed by arrays each corresponding to at least two sub-pixels among a plurality of (three) sub-pixels in a single pixel are different; or a condition in which a plurality of (three) sub-pixels in a single pixel is not lined up in one direction. In addition, in the present invention, the cycles of the sub-pixel array patterns, that is, the cycles of the sub-pixels (color filters) also include a cycle of sub-pixels in a single pixel.

In the example shown in FIG. 12(B), each sub-pixel 32r has a rhomboid shape that is vertically long in the y (vertical) direction in the drawing, and is disposed on the left side of each square-shaped pixel 32 in the drawing, each sub-pixel 32g has a circular shape, and is disposed on the lower right side of the pixel 32 in the drawing, and each sub-pixel 32b has a rectangular shape (square shape), and is disposed on the upper right side of the pixel 32 in the drawing. In the display unit 30 shown in FIGS. 12(A) and 12(B), a pixel array pattern 38 corresponds to a case where forms of three sub-pixels 32r, 32g, and 32b within a single pixel are different such that intensities thereof are different, and corresponds to a case where a plurality of (three) sub-pixels in a single pixel is not lined up in a single direction.

In the example shown in the drawing, the arrangement pitch (horizontal pixel pitch Ph) of the pixels 32 in the horizontal direction and the arrangement pitch (vertical pixel pitch Pv) of the pixels 32 in the vertical direction are substantially equal to each other, and are referred to as a pixel pitch Pd. That is, a region, which is formed of the three sub-pixels 32r, 32g, and 32b of a single pixel 32, and a pixel region 36, which is formed of a black matrix (BM) 34 (pattern material) surrounding the sub-pixels 32r, 32g, and 32b, have square shapes. It should be noted that the pixel region 36 corresponds to a single pixel 32, and therefore the pixel region 36 is hereinafter also referred to as a pixel.

It should be noted that the pixel pitch Pd (the horizontal or vertical pixel pitch Ph or Pv) may have any value if it is a pitch corresponding to a resolution of the display unit 30, and may be, for example, a pitch in a range of 84 μm to 264 μM.

In the examples shown in the drawing, the shapes of the sub-pixels 32r, 32g, and 32b within one pixel are respectively a rhomboid, a circle, and a rectangle. However, the present invention is not limited to this, and the shapes may be any shapes if there is provided the pixel array pattern 38. In the pixel array pattern 38, three sub-pixels having the same forms shown in FIG. 9 are lined up in the horizontal direction of the drawing, each pixel 32 is repeated in the horizontal direction and the vertical direction, and the cycles and intensities of the sub-pixels (color filters) are the same for the three sub-pixels of RGB.

Figure 13A:
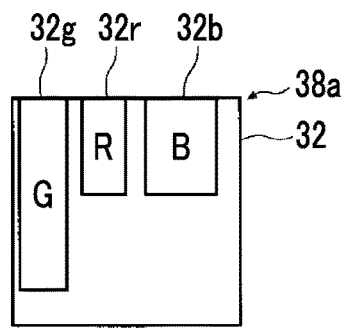
FIGS. 13A to 13C are respectively schematic explanatory diagrams illustrating examples of constituent units of pixel array patterns in which at least either shapes or cycles of three sub-pixels applied to the present invention are different.
Figure 13B:
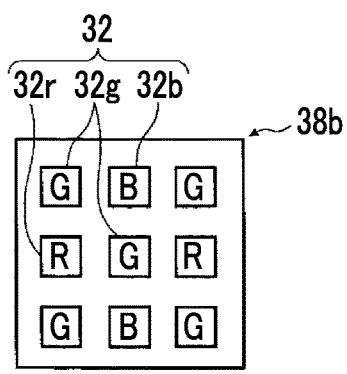
Figure 13C:
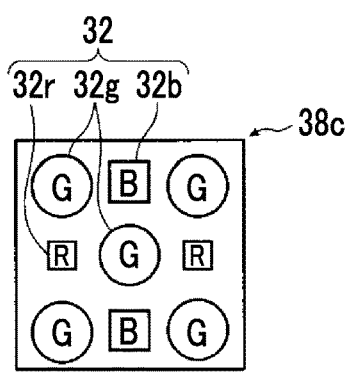
Figure 14A:
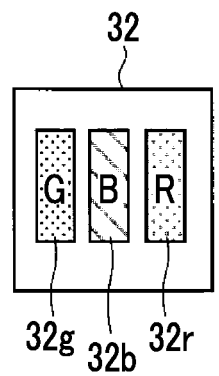
FIGS. 14A and 14B are respectively explanatory diagrams schematically illustrating examples of variations of intensities of three sub-pixels in the pixels of the pixel array pattern of the display unit shown in FIG. 9.
Figure 14B:
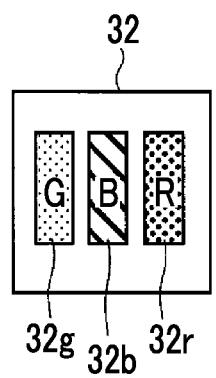

Alternatively, the sub-pixels (color filters) 32r, 32g, and 32b having opening shapes called a pin tile structure shown in FIGS. 13A to 13C may be used. In addition, there may be provided sub-pixel array patterns each of which is formed of the sub-pixels 32r, 32g, and 32b.

As shown in FIG. 13A, the forms of the three sub-pixels 32r, 32g, and 32b of the pixel 32 may be different (the shapes may be rectangles, but the sizes thereof may be different). This case corresponds to the case where the intensities thereof are different. In this case, it can be said that the cycles of the sub-pixels are the same.

That is, in the example shown in FIG. 13A, the pixel array pattern 38a is formed such that each pixel is formed of the three sub-pixels 32r, 32g, and 32b having different forms. Any of the cycles of the respective sub-pixel array patterns of the three sub-pixels 32r, 32g, and 32b is the same as the cycle of the pixel array pattern 38a.

It should be noted that in the present invention, the condition, in which the forms of the sub-pixels are different, is defined to include not only a case where the shapes of the sub-pixels are different but also a case where the sizes of the sub-pixels are different.

As shown in FIG. 13B, even when the forms of the three sub-pixels 32r, 32g, and 32b are the same, a repetition cycle (the cycle of the sub-pixel array pattern) of the sub-pixels 32g may be different from repetition cycle of the sub-pixels 32r and 32b. In this example, the cycle of the sub-pixels 32g is a half of the cycle of the sub-pixels 32r and 32b. In this case, it can be said that the intensities of the sub-pixels are the same.

That is, in the example shown in FIG. 13B, a pixel array pattern 38b is formed such that each pixel 32 is formed of four sub-pixels including the two sub-pixels 32g and the sub-pixels 32r and 32b. Either of the cycles of the respective sub-pixel array patterns of the sub-pixels 32r and 32b is the same as the cycle of the pixel array pattern 38a. The cycle of the sub-pixel array pattern of the sub-pixels 32g is a half of the cycle of the pixel array pattern 38a.

As shown in FIG. 13C, the repetition cycle (the cycle of the sub-pixel patterns) and the form (both the shape and the size) of the sub-pixels 32g may be different from those of the sub-pixels 32r and 32b. This case corresponds to the case where both the cycles and the intensities of the sub-pixels are different.

That is, in the example shown in FIG. 13C, in a manner similar to the example shown in FIG. 13B, a pixel array pattern 38c is formed such that each pixel 32 is formed of four sub-pixels including the two sub-pixels 32g and the sub-pixels 32r and 32b. Either of the cycles of the respective sub-pixel array patterns of the sub-pixels 32r and 32b is the same as the cycle of the pixel array pattern 38a. The cycle of the sub-pixel array pattern of the sub-pixels 32g is a half of the cycle of the pixel array pattern 38a.

FIG. 14A shows a BM structure of a pixel in which an intensity variation of GBR sub-pixels is large and which is formed of GBR sub-pixels having the same shapes. FIG. 14B shows a BM structure of a pixel in which an intensity variation of GBR sub-pixels is small and which is formed of GBR sub-pixels having the same shapes. Considering only a G sub-pixel having a highest intensity, a wiring pattern of the conductive film can be designed.

Figure 15:
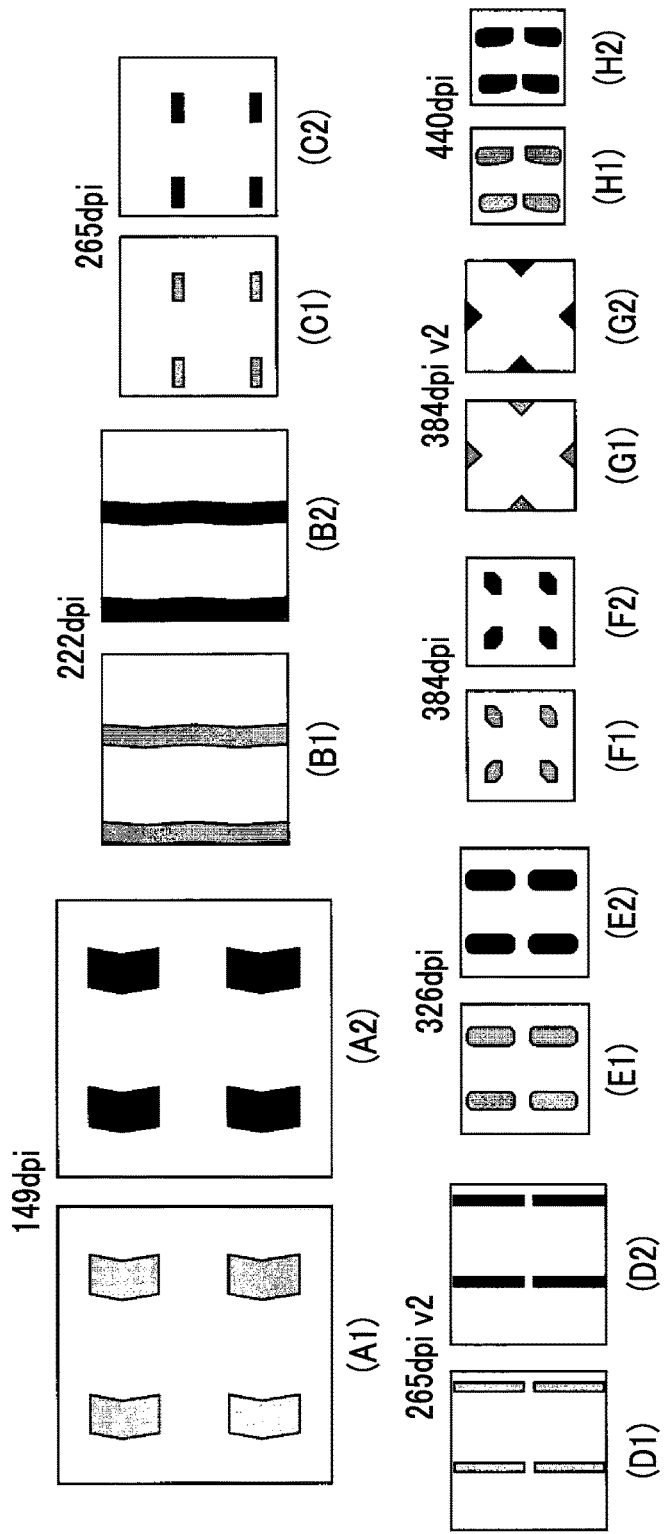
FIGS. 15(A1) to 15(H2) are schematic diagrams illustrating examples of repetition units each having 2×2 pixels of representative sub-pixels of pixel array patterns of display units of which resolutions, shapes, and intensities are different.

The resolutions and intensities of the BMs each having 2×2 pixels of the display used in the present invention are shown in FIGS. 15(A1) to 15(H2). Resolutions, shapes, or intensities (luminances) of the respective BMs shown in FIGS. 15(A1) to 15(H2) are different. FIGS. 15(A1) to 15(H2) show only the G channel (G sub-pixels), and do not show the B channel (B sub-pixels) and the R channel (R sub-pixels), but it is apparent that the resolutions and the shapes thereof are the same.

FIGS. 15(A1) and 15(A2) each show four G sub-pixels having reed shapes, which are curved toward the center and the left side in the drawing, at a resolution of 149 dpi, where intensities thereof are 0.5 and 1.0 when the intensities of the reference display are normalized.

FIGS. 15(B1) and 15(B2) each show four G sub-pixels having band shapes which extend in the vertical direction in the drawing, at a resolution of 222 dpi, where intensities thereof are 0.5 and 1.0 when the intensities of the reference display are normalized.

FIGS. 15(C1) and 15(C2) each show four G sub-pixels having plate shapes which are arrayed in the horizontal direction in the drawing, at a resolution of 265 dpi, where intensities thereof are 0.5 and 1.0 when the intensities of the reference display are normalized.

FIGS. 15(D1) and 15(D2) each show four G sub-pixels having plate shapes which are arrayed in the vertical direction in the drawing, at a resolution of 265 dpi, where intensities thereof are 0.5 and 1.0 when the intensities of the reference display are normalized.

FIGS. 15(E1) and 15(E2) each show four G sub-pixels having rectangular shapes which are arrayed in the horizontal direction in the drawing, at a resolution of 326 dpi, where intensities thereof are 0.5 and 1.0 when the intensities of the reference display are normalized.

FIGS. 15(F1) and 15(F2) each show four G sub-pixels having small rectangular shapes which are arrayed in four angular directions in the drawing, at a resolution of 384 dpi, where intensities thereof are 0.5 and 1.0 when the intensities of the reference display are normalized.

FIGS. 15(G1) and 15(G2) each show four G sub-pixels having triangular shapes which are arrayed in directions of four sides in the drawing, at a resolution of 384 dpi, where intensities thereof are 0.5 and 1.0 when the intensities of the reference display are normalized.

FIGS. 15(H1) and 15(H2) each show four G sub-pixels having rectangular shapes which are arrayed in the vertical direction in the drawing, at a resolution of 440 dpi, where intensities thereof are 0.5 and 1.0 when the intensities of the reference display are normalized.

For example, the conductive film 10, 11, or 11A may be disposed on a display panel of the display unit 30 having the BM pattern 38 formed by the BMs 34 that defines the above-mentioned sub-pixel array pattern of RGB. In this case, the wiring pattern 24 is made to be irregular (random) and optimized in terms of moiré visibility with respect to the luminance value of the BM (pixel array) pattern 38 including the sub-pixel array patterns of RGB. Therefore, there is almost no interference in spatial frequency between the array cycle of the pixels 32 and the wiring array of the thin metal lines 14 of the conductive film 10, 11, or 11A, and occurrence of moiré is suppressed.

However, the pixel array pattern of the display, which is used when optimization of moiré is optimized, is precisely defined by each sub-pixel array pattern of the plurality of colors such as RGB, for example, repetition frequencies and shapes of the sub-pixels. Therefore, it is necessary to accurately define a resolution of the sub-pixels with respect to the resolution of the display. However, in the present invention, it is necessary to use the light intensity of the pixel array pattern of the display, for example, the luminance value (luminance image data). Therefore, in terms of the intensity frequency, it can be said that it is not necessary to clearly divide RGB since a problem arises in that sub-pixels (indicate a single channel) with a certain intensity are arrayed in a certain manner. Consequently, in order to design a randomized mesh pattern which is optimal for the display, when indicators, that is, quantitative values of evaluation of moiré are calculated, a worst value thereof at the time of lighting on for each color of RGB may be used.

Figure 10:
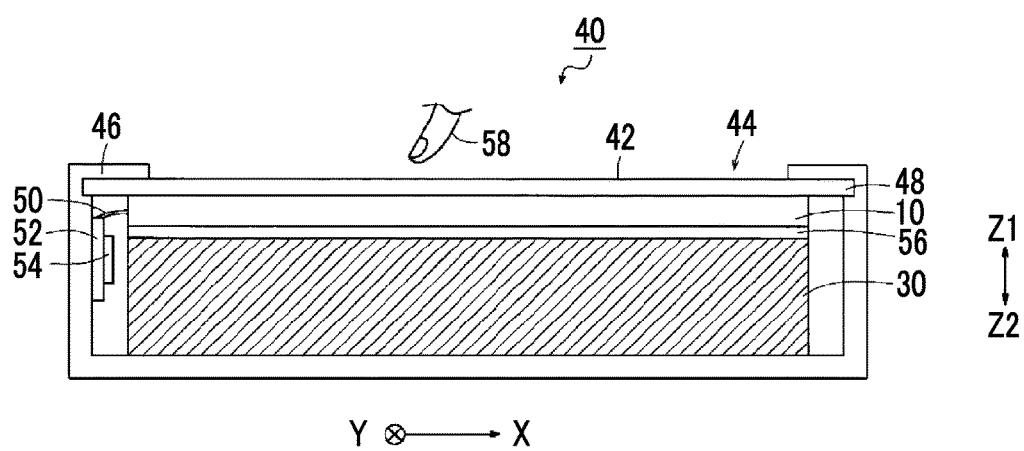
FIG. 10 is a schematic cross-sectional view of an example of a display device provided with the conductive film shown in FIG. 1.

Next, a display device, in which the conductive film of the present invention is incorporated, will be described with reference to FIG. 10. In FIG. 10, a projected capacitive type touch panel, in which the conductive film 10 according to the first embodiment of the present invention is incorporated, will be described as a representative example of a display device 40, but it is needless to say that the present invention is not limited to this example.

As shown in FIG. 10, the display device 40 includes the display unit 30 (refer to FIG. 9) that can display a color image and/or a monochrome image, a touch panel 44 that detects a contact position on an input surface 42 (located on the side as directed by the arrow Z1), and a housing 46 in which the display unit 30 and the touch panel 44 are housed. A user is able to access the touch panel 44 through a large opening portion provided in one surface (on the side as directed by the arrow Z1) of the housing 46.

The touch panel 44 includes not only the conductive film 10 (refer to FIGS. 1 and 2) described above but also a cover member 48 stacked on one surface (on the side as directed by the arrow Z1) of the conductive film 10, a flexible substrate 52 electrically connected to the conductive film 10 through a cable 50, and a detection control unit 54 disposed on the flexible substrate 52.

The conductive film 10 is bonded to one surface (on the side directed by the arrow Z1) of the display unit 30 through an adhesive layer 56. The conductive film 10 is disposed on the display screen such that the other main surface side (second wiring portion 16b side) is opposite to the display unit 30.

The cover member 48 functions as the input surface 42 by covering one surface of the conductive film 10. In addition, by preventing a contact member 58 (for example, a finger or a stylus pen) from coming into direct contact with the conductive film 10, it is possible to suppress the occurrence of a scratch, adhesion of dust, and the like, and thus it is possible to stabilize conductivity of the conductive film 10.

The material of the cover member 48 may be, for example, glass or a resin film. One surface (on the side as directed by the arrow Z2) of the cover member 48 may be coated with silicon oxide or the like, and may be adhered to one surface (on the side as directed by the arrow Z1) of the conductive film 10. Further, in order to prevent damage due to rubbing or the like, the conductive film 10 and the cover member 48 may be configured to be bonded to each other.

The flexible substrate 52 is an electronic substrate having flexibility. In the example shown in this diagram, the flexible substrate 52 is fixed to an inner wall of the housing 46, while the position of the substrate may be varied. The detection control unit 54 constitutes an electronic circuit that catches a change in the capacitance between the contact member 58 and the conductive film 10 and detects the contact position (or the approach position) when the contact member 58 as a conductor is brought into contact with (or comes closer to) the input surface 42.

The display device, to which the conductive film according to the present invention is applied, basically has the above-mentioned configuration.

Next, in the present invention, processes of evaluating moiré visibility on a wiring pattern of the conductive film with respect to a predetermined pixel array (BM) pattern of the display device having a predetermined intensity (luminance value) and performing optimization will be described. That is, a description will be given of the processes of evaluating and determining a randomized wiring pattern which is optimized such that moiré with respect to a predetermined pixel array (BM) pattern of the display device with a predetermined intensity is not perceived by human visual sensation, from at least one point of view, in the conductive film according to the present invention.

Figure 16:
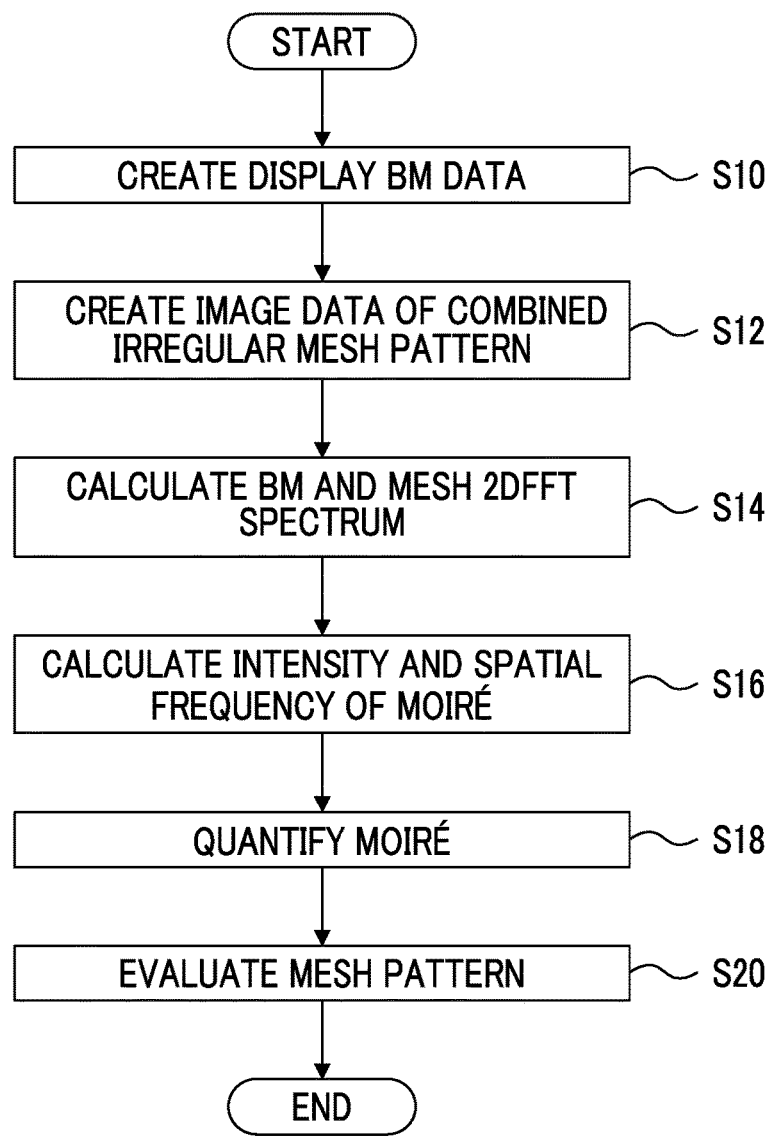
FIG. 16 is a flowchart illustrating an example of a method of evaluating wiring on the conductive film according to the present invention.

FIG. 16 is a flowchart illustrating an example of a method of evaluating the conductive film of the present invention.

In the method of evaluating the wiring pattern of the conductive film of the present invention, moirés (frequencies and intensities) of the respective colors with frequencies equal to or less than a highest frequency of moirés and predetermined intensities defined in accordance with a display resolution of the display unit, are collected on the basis of the frequencies and the intensities of moirés which are obtained through frequency analysis using fast Fourier transforms (FFT) of luminance image data of the BM (pixel array) patterns at the time of lighting on for each color of the plurality of colors (for example, RGB) of the display unit of the display device and image data of the combined wiring pattern which is made to irregular by forming the entirety or a part of at least one of the upper and lower wiring patterns of the conductive film as a parallelogram wiring pattern which is made to be irregular, evaluation values of moirés of the respective colors are obtained by applying human visual response characteristics to intensities of moirés at the frequencies of the collected moirés of the respective colors in accordance with the observation distance, an indicator (quantitative value) of evaluation of moirés is calculated on the basis of evaluation values of a plurality of moirés, a combined wiring pattern, which satisfies a condition where the calculated indicator of evaluation of moirés is set in advance, is evaluated as a combined wiring pattern which is optimized such that moirés are not visually perceived, and thereby it is evaluated and determined that the upper and lower wiring patterns forming the combined wiring pattern is optimized. Here, the entirety or a part of at least one of the upper and lower wiring patterns is a parallelogram wiring pattern which is made to be irregular in a predetermined range with angles of rhomboid shapes maintained with respect to the pitches of the rhomboid shapes of the rhomboid wiring pattern. In the method according to the present invention, FFT is generally used for the frequencies and intensities of moirés, and the following processes are defined because the frequency and intensities of a target may greatly vary depending on the way of usage.

In the present invention, first, it is preferable that the following is considered: the display screen of the display unit of the display device is observed from one point of view in the front. In this case, the present invention is not limited to this, but the display screen may be observed from any point of view if moiré visibility can be improved in a case where observation is performed from at least one point of view.

As might be expected, in the present invention, it is preferable that the following cases are considered: a case where the display screen is observed from the front (a case of front observation); and a case where the display screen is obliquely observed (a case of oblique observation).

Hereinafter, the following item will be described: imaging is performed for each color on the BM (pixel array) pattern which has sub-pixels with three colors such as RGB.

In the method according to the present invention, as shown in FIG. 16, first, in step S10 as process 1, display BM data is created.

Figure 17:
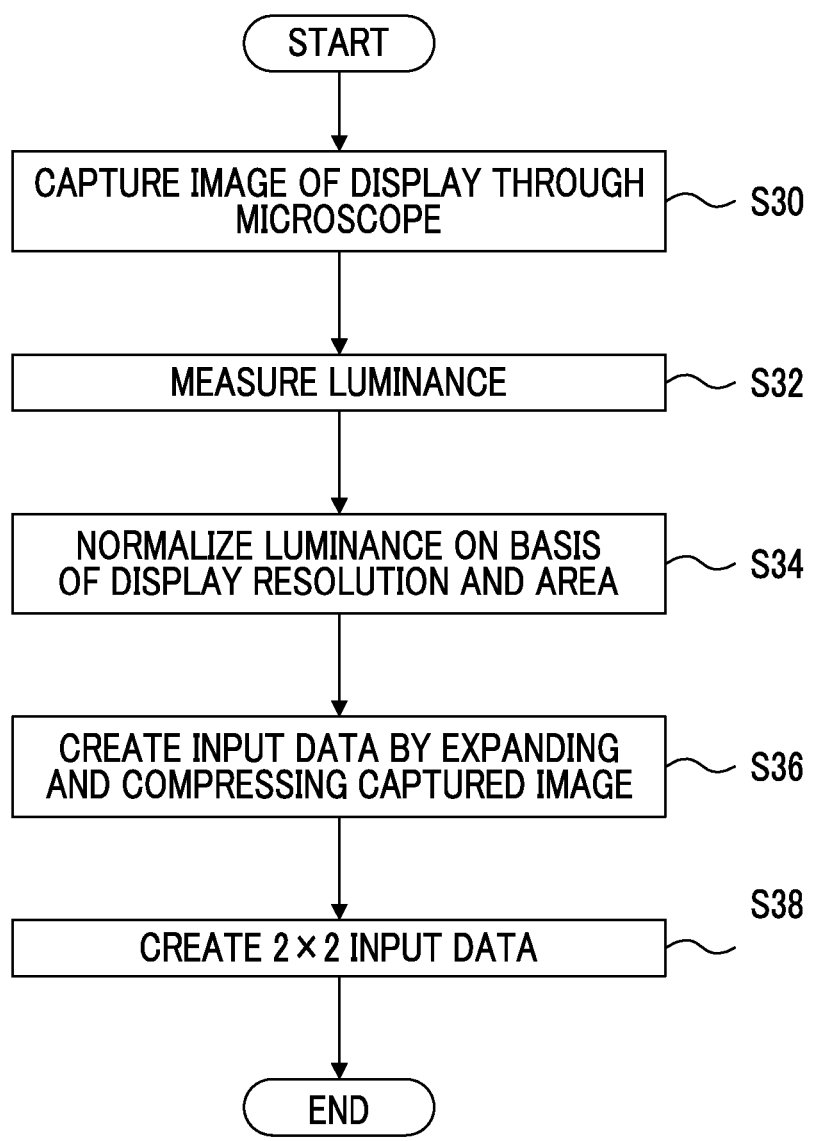
FIG. 17 is a flowchart illustrating a specific example of a method of creating display BM data for a method of evaluating the conductive film of the present invention.

Here, a method of creating display BM data in step S10 is shown in detail in FIG. 17.

FIG. 17 is a flowchart illustrating a specific example of the method of creating display BM data in the method of evaluating the conductive film of the present invention.

As shown in FIG. 17, first, in step S30, imaging of the display is performed using a microscope. That is, in step S30, an image of the display screen (an image of the sub-pixel array pattern of each color) of the display unit of the display device is captured for each color of RGB.

In step S30, first, the display unit 30 of the display device 40 is turned on for each color of RGB. At this time, it is preferable that the luminance is maximized in a range in which it can be obtained through setting change of a light emitting side (display device 40).

Subsequently, an image of the sub-pixels is captured in a state where the sub-pixels of each color of RGB are lit on. That is, an image of transmitted light of each of the sub-pixels (RGB color filters) 32r, 32g, and 32b of the pixel array patterns 38 (38a to 38c) of the display unit 30 shown in FIGS. 9, 12(B), and 13A to 13C is captured by using a microscope. In the imaging, it is preferable that white balance of a microscope is adjusted to white color of Macbeth chart.

A target display, and a microscope, a lens, and a camera used in imaging are not particularly limited, but, for example, LP101WX1(SL) (n3) (manufactured by LG DISPLAY Corp.) can be used as the display, STM6 (manufactured by OLYMPUS Corp.) can be used as the microscope, UMPlanFl10x (manufactured by OLYMPUS Corp.) can be used as the lens, d QIC-F-CLR-12-C (manufactured by QIMAGING Corp.) can be used as the camera.

In the example of the present invention, the LP101WX1 (SL) (n3) is used as the display, first, only the G channel is lit on with a maximum (MAX) intensity, the STM6 manufactured by OLYMPUS Corp. is used as the microscope, the UMPlanFl10x manufactured by OLYMPUS Corp. is used as the objective lens, and thereby imaging is performed.

Here, as the imaging conditions, for example, an exposure time period can be set to 12 ms, a gain can be set to 1.0, and white balance (G, R, B) can be set to (1.00, 2.17, 1.12). In addition, it is preferable that the captured image is subjected to shading correction.

Figure 18A:
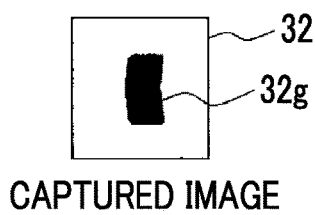
FIG. 18A is a schematic diagram illustrating an example of a captured image of a G sub-pixel of the display unit using the conductive film according to the present invention.

As a result, it is possible to acquire an image of one pixel of a G channel sub-pixel shown in FIG. 18A.

Here, in the present invention, the display is not limited, and any display may be used as a reference display, but it is preferable that the LP101WX1(SL) (n3) is used as a reference of the display.

Further, the BM pattern of the display LP101WX1(SL) (n3) has the BM patterns shown in FIGS. 15(A1) and 15(A2). It should be noted that FIGS. 15(A1) and 15(A2) show only G channel patterns but the same configuration is applied to the RB channels.

An image of one pixel of each sub-pixel of the RB channels can also be captured in the same manner as an image of one pixel of the G channel sub-pixel.

Next, after imaging, RGB luminance pixel information (luminance image data) is acquired by measuring spectra of the sub-pixel images through a spectrometer (small fiber optical spectrometer) and performing luminance conversion on the basis of the measured spectrum data.

For example, as described below, RGB sub-pixel (BM) input data may be created using the spectrometer.

Figure 18B:
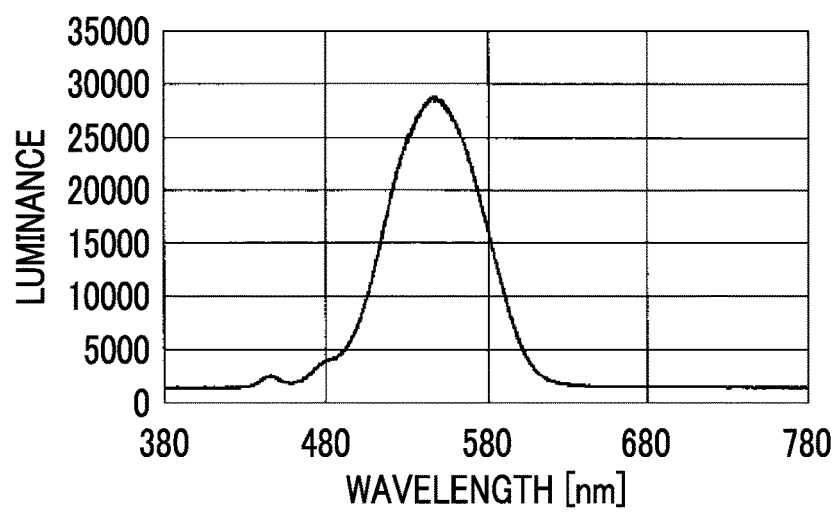
FIG. 18B is a graph illustrating an example of a spectrum of the G sub-pixel.

1. First, in step S32, measurement of the luminances is performed. The sub-pixels of the G channel of the display unit 30 are lit on in a single color, and light is measured by the spectrometer. As a result, for example, spectrum data shown in FIG. 18B can be obtained from the G sub-pixels. Spectrum data can be obtained from the RB sub-pixels in the same manner as the G sub-pixels.

In luminance measurement, a spectrometer USB2000+ manufactured by OCEAN OPTICS Inc. is used, a diffuser plate (CC-3-UV-S manufactured by OCEAN OPTICS Inc.) at the leading end of a fiber of the spectrometer is used, and an integration time period is set to 250 ms.

2. Next, in step S34, the image, which is captured through the microscope in step S10, is masked and binarized, and a mask image is created from image data of the captured image. In a method of creating the mask image, in a case of the G channel, an average value of pixel sizes of the light-on BMs is calculated, and mask data is acquired when the average value is set to a threshold value. Then, the mask image is created. The threshold value is an average value of only the G channel of an image corresponding to one pixel in the captured image. Also in a case of RB channel, in a manner similar to that of the G channel, the mask image is created from the image data of the captured image.

3. Subsequently, the luminance image data, which is normalized by a resolution×an area having a mask image value, is given to the obtained mask image, and is set as input data.

Figure 19:
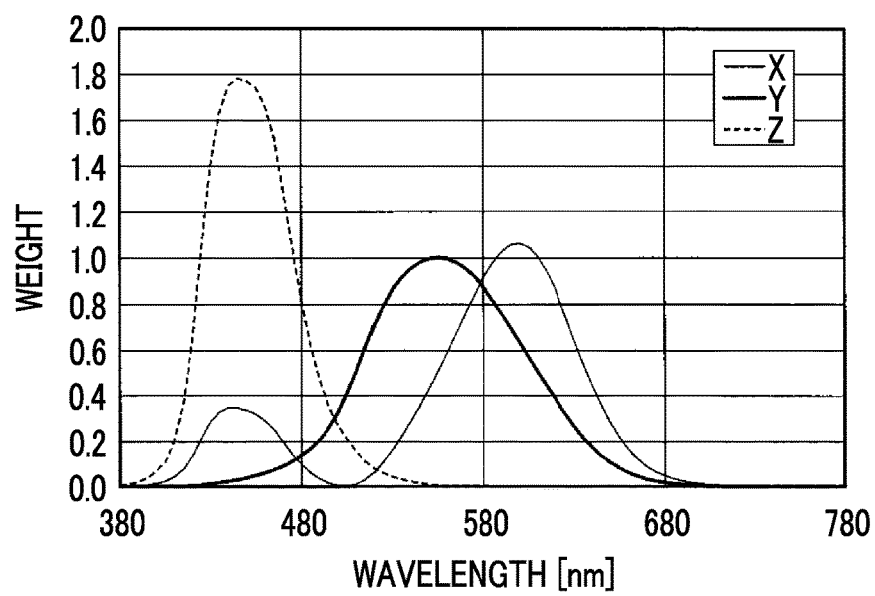
FIG. 19 is a graph illustrating an example of XYZ color matching functions applied to the present invention.

That is, a location of 1 of (0, 1) mask data of the mask image obtained in the section 2 is replaced with an integral value through the XYZ color matching functions shown in FIG. 19 in the spectrum data obtained in the section 1. For example, if the input data of the G sub-pixel is intended to be created, a product (G×Y) of the spectrum data G of G shown in FIG. 18B and the spectrum data Y of the luminance Y of the XYZ color matching function shown in FIG. 19 may be acquired. In addition, if the input data of the B sub-pixel is intended to be created, a product (B×Y) of the spectrum data B of B and the spectrum data Y of the luminance Y of the XYZ color matching function shown in FIG. 19 may be acquired. Likewise, the input data of the R sub-pixel may be created. At this time, the calculated luminance (luminance image data) Y is proportional to an opening area (area having the mask image value) of the sub-pixels and the number of pixels (resolution) included in a sensor of the spectrometer, and is therefore normalized by the number of pixels×the opening area, that is, the resolution×the area having the mask image value. The reason for this is that a macro luminance can be regarded as a value which is obtained by multiplying the opening area of the sub-pixels by the number of pixels included in the sensor in a case where the sub-pixels are regarded as a set of infinitesimal light sources.

Figure 18C:
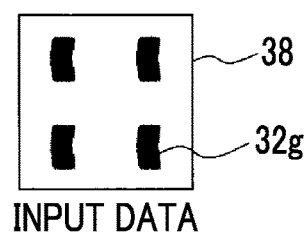
FIG. 18C is a schematic diagram illustrating an example of input data of 2×2 pixels.

Subsequently, in step S36, the resolution of the microscope image is different from desired input data (12700 dpi). Therefore, the input data pieces of the RGB sub-pixels obtained in step S34 each are expanded and compressed (reduced) in a bicubic method, the display luminance of the present example is normalized to 1.0 in step S38, and display BM data (normalized luminance image data) is created as input data of 2 pixels×2 pixels shown in FIG. 18C.

In such a manner, it is possible to acquire the display BM data.

The display BM data, which is obtained in such a manner, becomes normalized luminance image data which is normalized on the basis of the luminance of the reference display. Therefore, even compared with another display, the comparison can be performed on the basis of absolute values.

Meanwhile, before the two-dimensional fast Fourier transform (2DFFT (base 2)) is performed on the display BM data, it is preferable that input data of 2 pixels×2 pixels is repeatedly copied by an integer multiple approximate to an image size of 20000 pix×20000 pix, and thereby the normalized luminance image data is created as input data for moiré evaluation.

It should be noted that the input data pieces of the RGB sub-pixels obtained in step S34 each may be set at a resolution of 12700 dpi which is a high resolution through bilinear interpolation, without creation of the input data of 2 pixels×2 pixels, and an image size thereof may be bicubic-converted into 109 pix (pixels)×109 pix (pixels). It should be noted that, if the resolution of the optical imaging system is given, it is possible to calculate the values in accordance with the resolution.

Subsequently, the normalized luminance image, of which the image size is 109 pix×109 pix, with the resolution of 12700 dpi is repeatedly copied by an integer multiple (183 times) approximate to an image size of 20000 pix×20000 pix for each color of RGB, and thereby the normalized luminance image data as input data for moiré evaluation my be created.

The method of acquiring the display BM data (normalized luminance image data) indicating the RGB luminance pixel information by capturing images of the RGB sub-pixel array patterns of the display unit 30 is not limited to the method of measuring spectra of the respective sub-pixel images through the above-mentioned spectrometer and performing luminance conversion on the basis of the measured spectrum data. The captured image data may be directly converted into luminance values of the respective colors (RGB).

For example, on the basis of captured image data of the captured image of the sub-pixel array pattern of each color, a luminance value of each color (RGB) is converted, and luminance image data (total three data pieces) of RGB is created on the basis of a luminance of the display=1.0.

Assuming that red image data is R, green image data is G, blue image data is B, and the luminance value is Y, for conversion from the captured image into the luminance value, Y (luminance value) is calculated through the following conversion Expression (2), and R, G, and B color filter images (luminance ratio images) are created.

$$Y=0.300R+0.590G+0.110B \qquad (2)$$

The maximum value of the G sub-pixel (color filter) image (luminance ratio image) obtained in such a manner is 1.0 (=0.25*255), that is, the luminance images of the R, G, and B sub-pixels as references are normalized. Thereby, a normalized luminance image (image data) of each of the RGB sub-pixels can be created.

Next, in process 2, image data of the combined irregular mesh pattern 24 of the conductive film is created.

As shown in FIG. 16, in step S12, by forming the entirety or a part of at least one of the upper and lower wiring patterns as the irregular parallelogram wiring pattern, the image data of the combined irregular mesh pattern 24 is created.

Here, the image data of the combined irregular mesh pattern 24 is created as follows.

First, transmittance image data pieces of the mesh-shaped wiring patterns 24a and 24b (thin metal lines 14) on the upper and lower sides of the conductive film 10 (refer to FIGS. 1 to 6) are respectively created and acquired, and image data of a combined wiring (mesh) pattern, in which the mesh-shaped wiring patterns 24a and 24b on the upper and lower sides overlap with each other, is created on the basis of the respective acquired transmittance image data pieces.

For example, in a case where the upper and lower wiring patterns 24a and 24b each are the random wiring pattern 25a shown in FIG. 2, for example, the patterns overlap with each other as shown in FIG. 4. Therefore, the image data (for example, binary data) of the combined wiring pattern 24, in which the patterns overlap with each other as shown in FIG. 4, is created on the basis of the transmittance image data (for example, binary data) of the wiring pattern 25a.

Further, for example, the upper wiring pattern 24a may be the random wiring pattern 25a shown in FIG. 2, and the lower wiring pattern 24b may be the regular wiring pattern 25b shown in FIG. 3. In this case, for example, the patterns overlap with each other as shown in FIG. 5. Therefore, on the basis of the transmittance image data of the wiring pattern 25a and the transmittance image data of the wiring pattern 25b (for example, both are binary data), image data (for example, binary data) of the combined wiring pattern 24, in which the patterns overlap with each other as shown in FIG. 5, is created.

Further, for example, as shown in FIG. 6, the upper wiring pattern 24a may be a combination between the dummy electrode portion 26 formed in the random wiring pattern 25a and the electrode portion 17a formed in the regular wiring pattern 25b, and the lower wiring pattern 24b may be the random wiring pattern 25a shown in FIG. 2. In this case, first, on the basis of the transmittance image data of the wiring pattern 25a and the transmittance image data of the wiring pattern 25b (for example, both are binary data), transmittance image data (for example, binary data) of a combined wiring pattern, in which the patterns are combined as shown in FIG. 6, is created. In addition, on the basis of the transmittance image data (for example, binary data) of the combined wiring pattern and the transmittance image data of the wiring pattern 25a (for example, both are binary data), image data (for example, binary data) of the combined wiring pattern 24, in which the patterns overlap with each other, is created.

The regular (mesh) wiring pattern 25b is, for example, as shown in FIG. 3, a rhomboid pattern in which a predetermined angle of the thin metal lines 14 as wiring with respect to the horizontal line is set. For example, the angle may be set to be less than 45° [deg]. In the example shown in the drawing, the pattern is a rhomboid pattern which has a predetermined pitch oblique at an angle of 30°.

In contrast, the random (mesh) wiring pattern 25a is a parallelogram wiring pattern which is made to be irregular in a predetermined range with the angle of the rhomboid shape maintained with respect to the pitch of the rhomboid shape of the regular rhomboid mesh pattern 25b.

In such a manner, the image data of the combined irregular mesh pattern 24 can be created.

The image data of the random wiring pattern 25a shown in FIG. 2, the regular wiring pattern 25b shown in FIG. 3, and the combined mesh pattern 24 may be provided in advance, or may be stored in advance. In this case, the pattern may be acquired from the provided or stored patterns.

Further, when the image data of the combined mesh pattern 24 and the transmittance image data of the random wiring pattern 25a and the regular wiring pattern 25b are created, a resolution thereof is set to, for example, 25400 dpi. In addition, the size of the transmittance image data is defined such that the pixel size is set as, for example, an integer multiple of the size (for example, 109 pix×109 pix) of a cyclic unit approximate to 20000 pix×20000 pix, similarly to the BM pattern 38. In such a manner, the image data and the transmittance image data can be created with the defined size.

Next, a method of making the regular rhomboid mesh pattern irregular in a predetermined manner will be described.

Figure 25:
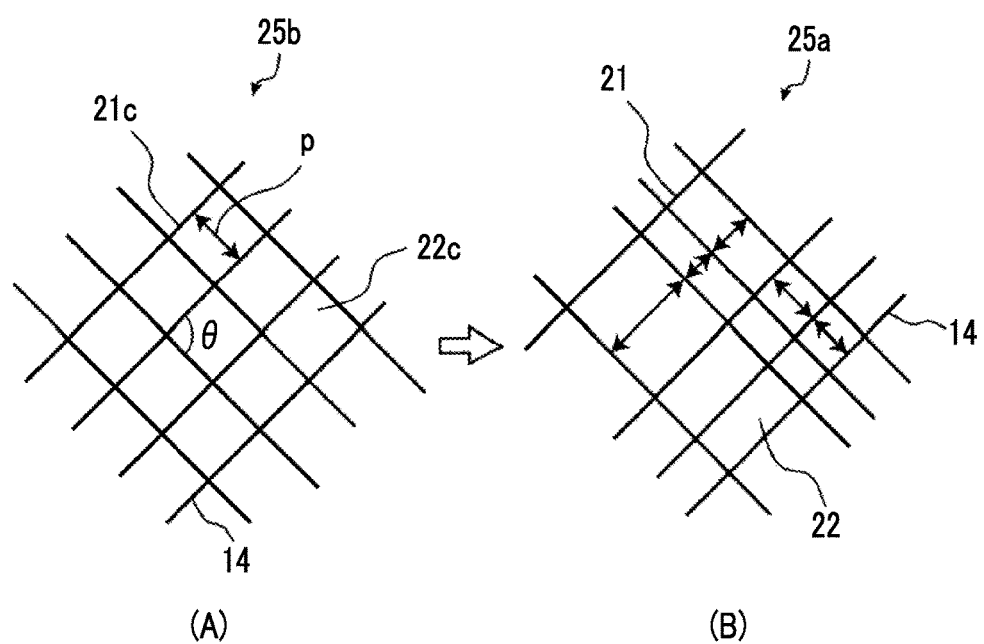
FIG. 25(A) is a rhomboid mesh pattern which is not made to be irregular.
FIG. 25(B) is a schematic diagram illustrating an example of a parallelogram mesh pattern, which is made to be irregular by making the rhomboid mesh pattern of FIG. 25(A) irregular, in a conductive film according to another embodiment of the present invention.

For example, a method of making the pitch of the rhomboid shape of the rhomboid wiring pattern 25b, which is shown in FIG. 25(A), irregular in a predetermined range and creating the random parallelogram wiring pattern 25a shown in FIG. 25(B) will be described as a representative example.

First, in the rhomboid shape of the regular rhomboid wiring pattern 25b shown in FIG. 25(A), a pitch p of the rhomboid shape is made to be irregular in a predetermined manner by shifting some thin metal lines 14 by a predetermined distance in parallel with two sides of the rhomboid facing each other. As a result, it is possible to obtain the randomized parallelogram wiring pattern 25a shown FIG. 25(B).

At this time, the two sides facing each other are maintained to be parallel with each other, and an angle $\theta$ is maintained. Therefore, the rhomboid shape of each opening is changed to a parallelogram shape. In a case where one line constituting the rhomboid is shifted in such a manner, the angle $\theta$ of the rhomboid is maintained before and after the pitch is made to be irregular. Consequently, the pitch p of the rhomboid is randomly changed, and the angle $\theta$ is maintained. Therefore, the pattern can be regarded as an angle maintenance pattern in which the pitch p of the rhomboid is randomly changed and the angle $\theta$ is kept constant.

In the present invention, irregularity is defined by a distribution of the pitches of the parallelograms made to be irregular to the pitches of the rhomboids which are not made to be irregular in the regular rhomboid wiring pattern 25b, for example, an average proportion based on a normal distribution or a uniform distribution.

In the present invention, a predetermined limit range of the irregularity defined as described above is preferably greater than 0% and equal to or less than 10%, more preferably in range of 2% to 10%, and yet more preferably in a range of 2% to 8%.

Here, the reason why the irregularity is limited in the predetermined limit range is as follows. In the limit range, occurrence of moiré is further suppressed, and image quality can be further improved in terms of visibility of moiré, and occurrence of moiré can be further suppressed even in a case where the overlapping BM patterns are slightly changed. As a result, it is possible to maintain excellent performance in terms of visibility of moiré. However, if the irregularity is out of the limit range, it is not possible to obtain the effect of application of the irregularity.

The method of making the regular rhomboid mesh pattern irregular in the predetermined range can be performed as described above.

Next, in process 3, by performing two-dimensional fast Fourier transform (2DFFT (base 2)) on each of the normalized luminance image data of the sub-pixels created in process 1 (step S10) and the image data of the combined mesh pattern created in process 2 (step S12), a spatial frequency of the spectrum peak and a peak spectrum intensity are calculated.

That is, as shown in FIG. 16, in step S14, first, by performing 2DFFT (the image size is 20000 pix×20000 pix) on the transmittance image data of the mesh pattern and the luminance image data of the sub-pixel array pattern (BM pattern) of each color of the BM pattern 38 for each color of RGB, Fourier spectra are calculated. Here, it is preferable that normalization is performed such that an intensity of a DC component is an average value of an image.

First, the peak frequency and the peak intensity are obtained by performing 2DFFT on the luminance image data for moiré evaluation obtained in step S10. Here, the peak intensity is treated as an absolute value of the Fourier spectrum.

This process is repeatedly performed for each color of RGB. At this time, if all small intensities not contributing to moiré are used, calculation becomes complicated, and an effect of improvement in accuracy is saturated. Therefore, it is preferable to provide a threshold value on the basis of the intensity. For example, in a case where the absolute value of the spectrum intensity is represented as a common logarithm, it is preferable to employ a value which is larger than $-2.2$ ($\log_{10}$(intensity)>$-2.2$).

Figure 20A:
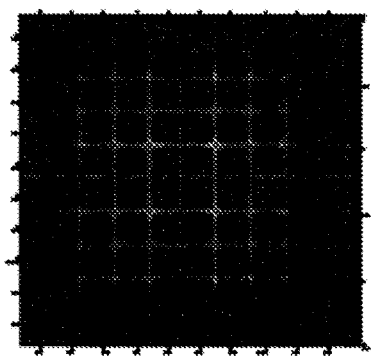
FIGS. 20A and 20B are respectively diagrams illustrating intensity characteristics of two-dimensional Fourier spectra of respective transmittance image data pieces of the pixel array pattern shown in FIG. 15(A1) and the wiring pattern shown in FIG. 1.

FIG. 20A shows an example of intensity characteristics of two-dimensional Fourier spectrum of the luminance image data of the G color (sub-pixel array pattern) obtained in such a manner.

Subsequently, by performing the 2DFFT on the image data of the combined mesh pattern 24 created in process 2 (step S12), the peak frequency and the peak intensity of the plurality of spectrum peaks of the two-dimensional Fourier spectra of the image data of the combined mesh pattern 24 are calculated. Here, the peak intensity is treated as an absolute value. For simplification of calculation, for example, in a case where the absolute value of the spectrum intensity is represented as a common logarithm, it is preferable that, only a threshold value of the intensity greater than $-2.0$ is treated.

Figure 20B:
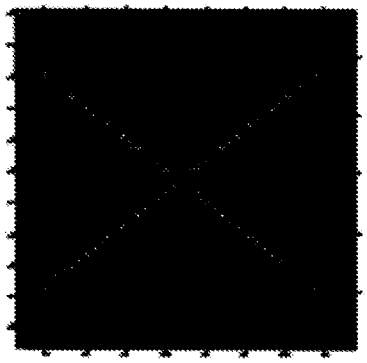

FIG. 20B shows an example of intensity characteristics of the two-dimensional Fourier spectra of the image data of the combined mesh pattern 24 obtained in such a manner.

In a case of changing a point of view, a spatial frequency of the mesh of the combined mesh pattern 24, an intensity thereof, and a spectrum intensity of the BM are different from those in the front view. For example, if the point of view for the combined mesh pattern 24 is set at 30°, it is preferable that an amount of deviation between the upper mesh pattern 24a and the lower mesh pattern 24b is set in consideration of a substrate thickness (for example, PET: 100 μm). It is preferable that the spectrum intensity of the BM is 0.9 times the intensity thereof in the front view.

As described above, FIGS. 20A and 20B are respectively diagrams illustrating the intensity characteristics of the two-dimensional Fourier spectra of the image data of the combined mesh pattern 24 and the luminance image data of the G color (sub-pixel array pattern) of the BM pattern 38.

In FIGS. 20A and 20B, white portions have high intensities, and indicate spectrum peaks. Therefore, from the results shown in FIGS. 20A and 20B, the peak frequencies and the peak intensities of spectrum peaks are calculated respectively for the image data of the combined mesh pattern 24 and the luminance image data of the BM pattern 38 at the time of lighting on for each color depending on the sub-pixel array patterns of three RGB colors. In other words, positions of the spectrum peaks on frequency coordinates in the intensity characteristics of the two-dimensional Fourier spectra of the image data of the combined mesh pattern 24 and the luminance image data of the BM pattern 38 (the sub-pixel array pattern of each color) at the time of lighting on for each color respectively shown in FIGS. 20A and 20B, that is, the peak positions indicate peak frequencies. The intensities of the two-dimensional Fourier spectra at the peak positions indicate peak intensities.

Here, the peak frequencies and the peak intensities of the spectrum peaks of the image data of the combined mesh pattern 24 and the luminance image data of the BM pattern 38 (the sub-pixel array pattern of each color) at the time of lighting on for each color are calculated and acquired in a manner similar to that of the following description. Hereinafter, summary thereof will be described. In addition, hereinafter, the luminance image data of the BM pattern 38 (the sub-pixel array pattern of each color) at the time of lighting on for each color is simply referred to as each sub-pixel array pattern of the BM pattern 38 represented as the luminance image data. The image data of the combined mesh pattern 24 is simply referred to as the combined mesh pattern 24 represented as the image data.

Figure 21:
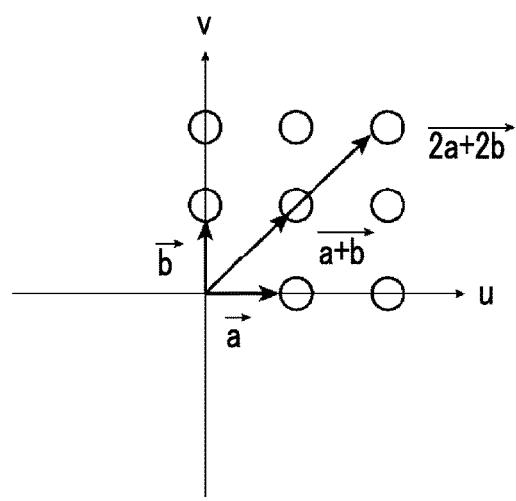
FIG. 21 is a graph illustrating a frequency peak position of the pixel array pattern of the display unit shown in FIG. 15(A1).

First, in the process of acquiring the peak frequencies, for peak calculation, the frequency peaks are obtained from basic frequencies of the combined mesh pattern 24 and the sub-pixel array patterns of the BM pattern 38. The reason for this is that, since the luminance image data and the image data for performing the 2DFFT processing are discrete values, the peak frequency depends on an inverse of the image size. As shown in FIG. 21, each frequency peak position can be represented by combination based on a bar and b bar as independent two-dimensional fundamental frequency vector components. Consequently, it is apparent that the obtained peak positions have a lattice shape.

Figure 22A:
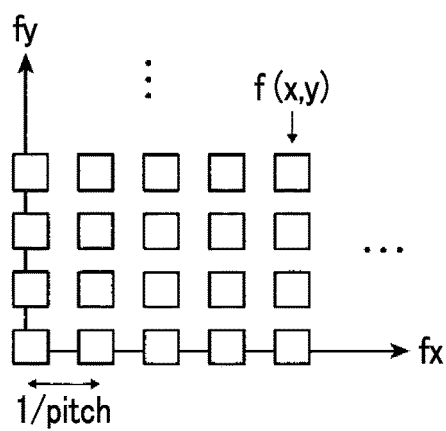
FIG. 22A is a graph a frequency peak position of an input pattern image.

That is, as shown in FIG. 22A, the positions of the spectrum peaks of the combined mesh pattern 24 and the sub-pixel array patterns of the BM pattern 38 on the frequency coordinates fxfy, that is, the peak positions are given as positions of points having a lattice shape on the frequency coordinates fxfy in which an inverse (1/p (pitch)) of the pattern pitch is set as a lattice interval.

In addition, FIG. 21 is a graph illustrating the frequency peak positions in the case of the luminance image data of the BM pattern 38 (the sub-pixel array pattern of the G color) at the time of emitting G-color light, and the frequency peak positions in a case of the image data of the combined mesh pattern 24 can also be obtained in a manner similar to that in the above description.

Figure 23A:
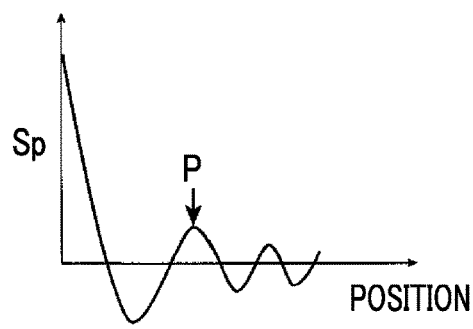
FIGS. 23A and 23B are respectively a graph in which exemplary intensity characteristics of two-dimensional Fourier spectrum are represented by a curve and a bargraph in which the intensity characteristics are represented by bars.
Figure 23B:
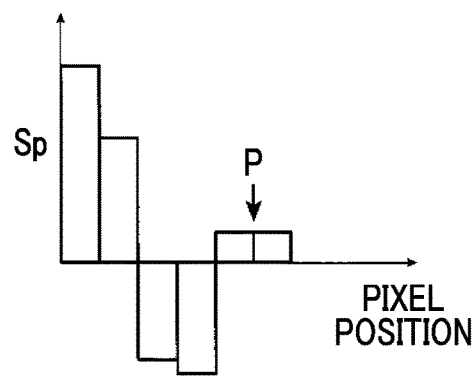

In contrast, in the process of acquiring the peak intensities, the peak positions are obtained by acquiring the peak frequencies, and thus the intensities (absolute values) of the two-dimensional Fourier spectra at the peak positions are obtained. At that time, FFT processing is performed on digital data, and thus in some cases, the peak position may be between a plurality of pixels. For example, when intensity (Sp) characteristics of the two-dimensional Fourier spectrum are represented by the curve (analog value) shown in FIG. 23A, intensity characteristics of the two-dimensional Fourier spectrum subjected to the digital processing are represented by a bargraph (digital values) shown in FIG. 23B. A peak P of the intensity of the two-dimensional Fourier spectrum shown in FIG. 23A is between two pixels in corresponding FIG. 23B.

Figure 22B:
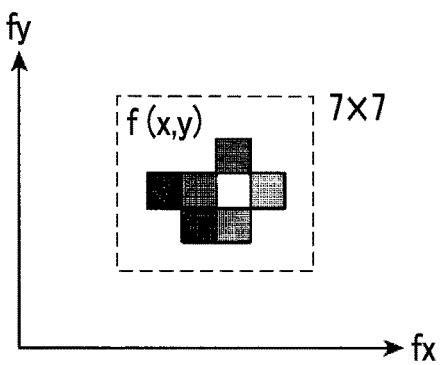
FIG. 22B is a graph illustrating calculation of a peak intensity at the frequency peak position.

Accordingly, if the intensity present at the peak position is intended to be acquired, as shown in FIG. 22B, it is preferable that the peak intensity is the sum of the intensities (absolute values) having highest ranks at a plurality of points among spectrum intensities of a plurality of pixels within a region including a plurality of pixels around the peak position, for example, the sum of the intensities having highest ranks at five points among spectrum intensities of the pixels within a region of 7×7 pixels.

Here, it is preferable that the obtained peak intensity is normalized by the image area (image size). For example, it is preferable that the intensity is normalized by the above-mentioned image size (Parseval's theorem).

Next, in process 4, a spatial frequency and a intensity of moiré are calculated from the peak frequencies and the peak intensities of the image data of the combined mesh pattern 24 and the peak frequencies and the peak intensities of the luminance image data of the BM pattern 38 (sub-pixel array pattern) at the time of lighting on for each color of RGB obtained in process 3 (step S14).

Specifically, as shown in FIG. 16, in step S16, the frequencies and the intensities of moirés for respective colors are calculated from the peak frequencies and the peak intensities of both two-dimensional Fourier spectra of the combined mesh pattern 24 and the sub-pixel array patterns of the respective RGB colors of the BM pattern 38 respectively calculated in step S14. Here, the peak intensities and the intensities of moirés are also treated as absolute values.

Here, spatial frequencies and intensities of moirés can be calculated through a convolution operation of the peak frequencies and the peak intensities of the sub-pixel array patterns of the respective RGB colors of the BM pattern 38 and the peak frequency and the peak intensity of the combined mesh pattern 24.

In real space, moiré is caused by multiplication of the image data of the combined mesh pattern 24 and the luminance image data of the BM pattern 38 (the sub-pixel array pattern of each color of RGB) at the time of lighting on for each color. Thus, in frequency space, both image data pieces are subjected to convolution integration (convolution). However, in steps S14 and S16, the peak frequencies and the peak intensities of both two-dimensional Fourier spectra of the combined mesh pattern 24 and the sub-pixel array pattern of each color of the BM pattern 38 are calculated. Therefore, a difference (an absolute value of a difference) between both frequency peaks of the combined mesh pattern 24 and the sub-pixel array pattern of a single color of RGB is obtained, the obtained difference is set as a frequency of moiré, a product between two sets of vector intensities obtained by combining both is obtained, and the obtained product is set as an intensity (absolute value) of moiré.

The frequency of moiré and the intensity of moiré are obtained for each color of RGB.

Here, the difference between the frequency peaks of the intensity characteristics of both two-dimensional Fourier spectra of the combined mesh pattern 24 and the sub-pixel array pattern of each color of the BM pattern 38 respectively shown in FIGS. 20A and 20B corresponds to a relative distance between the peak positions of both frequency peaks on the frequency coordinates, in intensity characteristics obtained by superimposing the intensity characteristics of both two-dimensional Fourier spectra for each color.

A plurality of spectrum peaks of both two-dimensional Fourier spectra between the combined mesh pattern 24 and the sub-pixel array pattern of each color of the BM pattern 38 is present for each color. Therefore, a plurality of the differences between the frequency peaks which are values of the relative distances, that is, a plurality of the frequencies of moiré is obtained. Consequently, if there are multiple spectrum peaks of both two-dimensional Fourier spectra, there are multiple obtained frequencies of moiré, and thus there are multiple obtained intensities of moiré.

However, in a case where the intensities of moiré at the obtained frequencies of moiré are weak, moiré is not visually perceived. Thus, it is preferable to deal with only moiré of which the intensity of moiré is regarded to be weak and is equal to or greater than a predetermined value, for example, moiré of which the intensity is equal to or greater than −4.5.

Here, in the display device, the display resolution is determined, thus the highest frequency, at which display can be performed on the display device, is determined depending on the resolution thereof. Hence, moiré having a frequency higher than the highest frequency is not displayed on the display device, and therefore it is not necessary to set the moiré as an evaluation target. Accordingly, the highest frequency of moiré can be defined in accordance with the display resolution. Here, the highest frequency of moiré, which has to be considered in the present invention, can be set to 1000/Pd (cycle/mm) when the pixel pitch of the pixel array pattern of the display is Pd (μm).

From the above description, in the present invention, in the frequencies and the intensities of moiré obtained from the spectrum peaks of both two-dimensional Fourier spectra, moiré as the evaluation (quantification) target in the present invention is moiré, of which a frequency is equal to or less than the highest frequency of moiré of 1000/Pd defined in accordance with the target display resolution (for example, 151 dpi in the present example), and moiré of which an intensity of moiré is equal to or greater than −4.5. In the present invention, the reason why moiré having the intensity of moiré equal to or greater than −4.5 is set as a target is as follows. If multiple moirés of which the intensity is less than −4.5 occur and thus the sum thereof is used, even originally invisible moiré may have to be scored. For this reason, in the present invention, a threshold value, which is equal to or greater than −4.5, is provided from an empirical visibility limit.

Next, in process 5, moiré is quantified using the frequency and the intensity of moiré for each sub-pixel of each color of RGB calculated in process 4 (step S16), and a quantitative value as an indicator of evaluation of moiré is obtained.

That is, as shown in FIG. 16, in step S18, convolution of the visual transfer function (VTF) and the spectrum peaks for moiré evaluation remaining in step S16 is performed, and quantified.

Before quantification of moiré, if there are multiple spectrum peaks of both two-dimensional Fourier spectra, there are multiple obtained frequencies of moiré, and thus it takes time to perform calculation processing. In such a case, the spectrum peaks of both two-dimensional Fourier spectra are provided in advance, spectrum peaks having weak peak intensities may be excluded, and only spectrum peaks having certain strong intensities may be selected. In that case, only the differences between the selected peaks are obtained, and thus it is possible to shorten the calculation time.

For example, as a target, convolution of the moiré spectrum and a visual transfer function (VTF) (which is 1.0 in a low frequency region equal to or less than the maximum value) at the observation distance of 400 mm is performed, and thereafter it is possible to deal with only moirés with an intensity of −3.8 or more.

Here, in order to extract only moirés which are visible to human eyes, the VTF corresponding to the observation distance of 400 mm is used on the basis of scattering effects in a system.

The spectrum peaks, which remain in such a manner, can be set as spectrum peaks for moiré evaluation. At this time, it is preferable that only peaks equal to or greater than −3.8 as a common logarithm are used as the spectrum intensities. Thereby, it is possible to extract perceived moiré.

Figure 24:
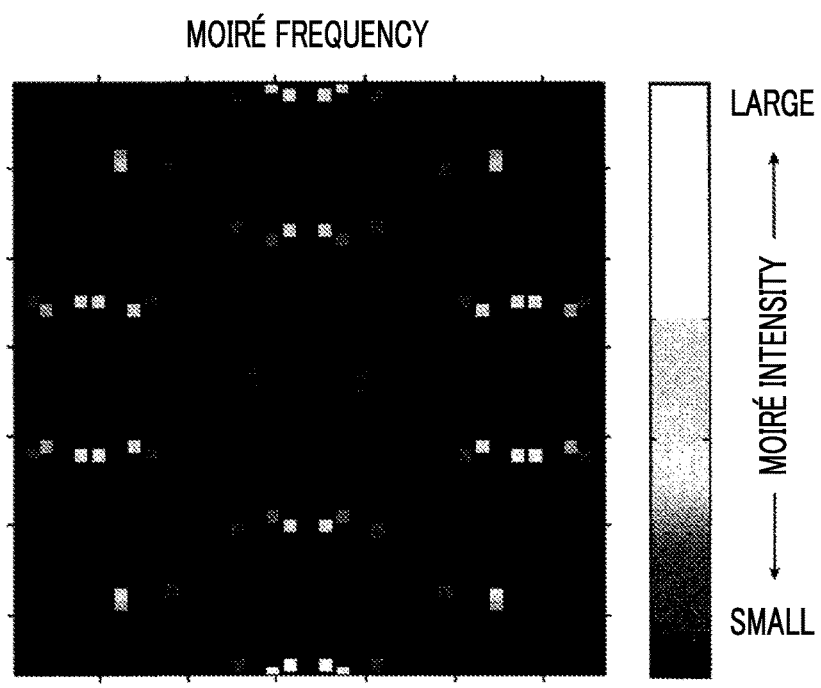
FIG. 24 is a schematic explanatory diagram schematically illustrating frequencies of moiré and intensities of moiré caused by interference between the pixel array pattern shown in FIG. 15(A1) and the wiring pattern shown in FIG. 1.

FIG. 24 shows frequencies of moiré and intensities of moiré obtained in such a manner. FIG. 24 is a schematic explanatory diagram schematically illustrating the frequencies of moiré and the intensities of moiré caused by interference between the pixel array pattern shown in FIG. 15(A1) and the wiring pattern shown in FIGS. 1 and 2. Those may be results of convolution integration of intensity characteristics of the two-dimensional Fourier spectra shown in FIGS. 20A and 20B.

In FIG. 24, the frequencies of moiré are represented by position on the vertical and lateral axes, and the intensities of moiré are represented by gray (achromatic color) density, where as the thickness of the color decreases and the color becomes white, the frequency increases.

In the quantification of moiré, specifically, in step S18, in the frequencies and the intensities (absolute values) of moirés for the sub-pixels of the respective colors of RGB obtained in step S16, a plurality of evaluation values of moirés of the respective colors is calculated by applying human visual response characteristics (VTF) corresponding to the observation distance of 750 mm as an example of human visual response characteristics represented by the following Expression (1), that is, by performing convolution integration. Here, in order to score moiré, the VTF corresponding to the observation distance of 750 mm is used.

$$VTF=5.05e^{-0.138k}(1-e^{0.1k}) \quad (1)$$

$$k=\pi du/180$$

Here, k is a spatial frequency (cycle/deg) defined by a solid angle, u shown in the above-mentioned Expression (1) is a spatial frequency (cycle/mm) defined by a length, and d is defined by an observation distance (mm).

The visual transfer function represented in the above-mentioned Expression (1) is called a Dooley-Shaw function, and is obtained with reference to description of a reference (R. P. Dooley, R. Shaw: Noise Perception in Electrophotography, J. Appl. Photogr. Eng., 5, 4 (1979), pp. 190-196.).

In such a manner, it is possible to obtain the evaluation value of moiré using a common logarithm of the intensity for each color of RGB.

Here, the above-mentioned steps S10 to S18 are repeated for each color of RGB, and the evaluation values of moirés of RGB may be obtained. However, in each step of the above-mentioned steps S10 to S18, the calculation may be performed for each color of RGB.

A worst value, that is, a maximum value among the evaluation values of moirés of RGB obtained in such a manner is set as the indicator (quantitative value) of evaluation of moiré. A value of the indicator of evaluation of moirés is obtained as a value (common logarithm value) of a common logarithm of the indicator of evaluation of moirés represented by a common logarithm is obtained. It is preferable that evaluation is also performed by combining an evaluation image with RGB display in accordance with calculation of the worst value.

It can be said that the quantitative value of moiré, which is the indicator of evaluation of moiré, is a value of quantification of moiré and noise in the related art. In the present invention, noise is defined as a state in which a lot of moirés are present. Accordingly, in the present invention, if there is a peak in a single frequency, it is determined that moiré is present. In contrast, if there is a plurality of peaks in the vicinity of a single frequency, it is determined that noise is present. Basically, if randomicity is applied, a single peak intensity of moiré is attenuated, and the attenuated intensities are distributed in the vicinity of the peak. Therefore, if a plurality of distributed moiré peaks (noise) appears at a frequency which is disadvantageous to visual sense, a quantitative value of moiré becomes worse. Hence, in the present invention, as the indicators of evaluation of visibility of moiré and noise, the quantitative value of moiré is used.

The above-mentioned indicator of evaluation of moiré is obtained in a case where the conductive film 10 laminated on the display screen of the display unit 30 of the display device (display) 40 is observed from the front of the display screen. However, the present invention is not limited to this, and the indicator of evaluation of moiré in a case where observation is performed in a direction oblique to the front may be obtained.

In the case where the indicator of evaluation of moiré is obtained in a case where observation is performed in a direction oblique to the front, the intensities of RGB of the display 40 at the time of oblique observation are calculated at 90% of the luminance at the time of front observation, the process returns to step S14, and the peak frequencies and the peak intensities of the Fourier spectra of the respective colors are calculated again. Thereafter, steps S16 to S18 are repeated in the same manner, and the indicator of evaluation of moiré at the time of oblique observation is calculated.

In such a manner, if the indicators of evaluation of moiré are calculated at the time of front observation and oblique observation, a large value (worst value) among the indicators of evaluation of moiré at the time of front observation and oblique observation is calculated as the indicator of evaluation of moiré to be provided for moiré evaluation.

In a case where only one of the front observation and the oblique observation is not performed, the indicator of evaluation of moiré at the front observation or the oblique observation is set as the indicator of evaluation of moiré to be directly provided for moiré evaluation.

Next, in process 6, evaluation of the wiring pattern is performed on the basis of the indicator (quantitative value: worst value) of evaluation of moiré calculated in process 5 (step S24).

That is, as shown in FIG. 16, in step S20, if a common logarithm value of the indicator of evaluation of moiré of the current combined mesh pattern 24 obtained in step S18 is equal to or less than a predetermined evaluation threshold value, it is evaluated that the current combined mesh pattern 24 is an optimized combined mesh pattern of the conductive film of the present invention. For example, as shown FIG. 4 or 5, the current combined mesh pattern is set as the optimized combined mesh pattern in which, as shown in FIGS. 2 and 25(B), the entirety or a part of at least one of the upper and lower sides is formed of an irregular parallelogram wiring pattern in a predetermined range with angles maintained with respect to the rhomboid shapes of the regular rhomboid mesh pattern shown in FIGS. 3 and 25(A). As a result, it is evaluated that a conductive film having such an optimized combined mesh pattern is in the conductive film of the present invention.

Accordingly, it is evaluated that the upper wiring pattern 24a and the lower wiring pattern 24b overlapping with each other is a upper wiring pattern 24a and a lower wiring pattern 24b which are optimized in the conductive film of the present invention. In addition, it is evaluated that the random wiring pattern 25a shown in FIGS. 2 and 25(B) constitutes at least one of the upper wiring pattern 24a and the lower wiring pattern 24b or constitutes a part thereof. As a result, the wiring patterns are evaluated and set as wiring patterns used in the conductive film of the present invention.

The reason why the value of the indicator of evaluation of moiré is limited to be equal to or less than the predetermined evaluation threshold value as a common logarithm is as follows. If the value is greater than the predetermined evaluation threshold value, moiré, which is caused by interference between each sub-pixel array pattern of the BM pattern and the wiring pattern overlapping with each other, is visually perceived, and the visually perceived moiré offers a sense of discomfort to a user who observes the moiré. In a case where the value of the indicator of evaluation of moiré is equal to or less than the predetermined evaluation threshold value, the moiré may slightly offer a sense of discomfort, but does not matter.

Here, the predetermined evaluation threshold value is appropriately set in accordance with shapes and properties of the conductive film and the display device. The shapes and properties includes a line width of the thin metal line 14 of the combined mesh pattern 24, a shape, an angle, and a size (such a pitch) of the opening portion 22, a phase angle (a rotation angle, and a deviation angle) of the wiring pattern of two wiring layers, a shape, a size (such a pitch), and an arrangement angle of the BM pattern 38, and the like. However, for example, the predetermined value is preferably −2.80 ($10^{-2.80}$ as an antilogarithm) as a common logarithm, more preferably −3.17 as a common logarithm, yet more preferably −4.00 as a common logarithm. That is, for example, the indicator of evaluation of moiré is preferably equal to or less than −2.80 ($10^{-2.80}$ as an antilogarithm) as a common logarithm, more preferably equal to or less than −3.17 as a common logarithm, and yet more preferably equal to or less than −4.00 as a common logarithm.

In the present invention, in a manner similar to reference examples to be described later, regarding the conductive film using the regular rhomboid wiring pattern which is made to be irregular, the indicator (quantitative value) of evaluation of moiré is obtained in the above-mentioned evaluation method is obtained in accordance with the above-mentioned evaluation method, and functional evaluation to be described later is performed on the conductive film. It is preferable that the evaluation threshold value of the present invention is set in advance on the basis of a result of the functional evaluation.

Although described in detail later, the indicator of evaluation of moiré is obtained for each of the multiple combined mesh patterns 24 including the random wiring pattern 25*a*, and three functional evaluators perform functional evaluation on moiré, which is caused by interference between the combined mesh pattern 24 and the sub-pixel array pattern of each color of three colors such as RGB of the BM pattern, with their own eyes. If the indicator (quantitative value) of evaluation of moiré is equal to or less than −2.80 as a common logarithm, in a state where the display is lit on, deterioration is slightly observed in terms of visibility of moiré which is caused by interference between the superposed combined wiring pattern and the sub-pixel array pattern of each color of three colors such as RGB of the BM pattern, and the moiré may slightly offer a sense of discomfort but does not matter. If the indicator is equal to or less than −3.17 as a common logarithm, the most moiré does not matter. If the indicator is equal to or less than −4.00 as a common logarithm, deterioration is not observed.

Consequently, in the combined mesh pattern optimized in the present invention, the indicator (quantitative value) of evaluation of moiré is preferably specified to be equal to or less than −2.80 ($10^{-2.80}$ as an antilogarithm) as a common logarithm, more preferably specified to be equal to or less than −3.17 as a common logarithm, and yet more preferably specified to be equal to or less than −4.00 as a common logarithm.

It is apparent that a plurality of optimized combined mesh patterns 24 is obtained in accordance with the line width of the thin metal line 14 of the combined mesh pattern 24, the shape of the opening portion 22, the size (pitch and angle), a phase angle (a rotation angle, and a deviation angle) of the wiring pattern of two wiring layers, and the like. Here, a combined mesh pattern 24 having a small common logarithm value of the indicator of evaluation of moiré may be a best combined mesh pattern 24, and the plurality of optimized combined mesh patterns 24 may be prioritized.

In such a manner, the wiring patterns of the conductive film of the present invention can be determined, and then be evaluated.

As a result, the BM pattern of the display unit of the display device in a state of lighting on is superposed such that occurrence of moiré is suppressed. Thus, also for the display device with a different resolution, it is possible to provide the conductive film of the present invention which is excellent in moiré visibility regardless of the observation distance and has the optimized wiring pattern including the irregular wiring pattern.

In the present invention, in the optimized combined wiring pattern which is optimized with respect to the predetermined BM pattern of the display that emits light with a predetermined luminance, the random wiring pattern, which is made to be irregular in the above-mentioned predetermined range, is added. Therefore, occurrence of moiré is further suppressed, and image quality becomes further excellent in terms of visibility of moiré. Even in a case where the overlapping BM patterns are slightly changed, it is possible to suppress occurrence of moiré, and it is possible to maintain excellent performance in terms of visibility of moiré.

Hereinbefore, the conductive film according to the present invention, the display device comprising the conductive film, and the method of evaluating the conductive film have been described with reference to various embodiments and examples. However, it is apparent that the present invention is not limited to the embodiments and the examples and may be improved or modified in various forms without departing from the scope of the present invention.

EXAMPLES

Hereinafter, the present invention will be described in detail on the basis of examples.

As the upper wiring patterns 24*a* and the lower wiring patterns 24*b*, the following patterns are used: a plurality of the pixel array (BM) patterns 38 of the display that have different resolutions, emission intensities, and sub-pixel shapes typified by the G sub-pixel array patterns shown in FIG. 15(A1) to 15(H2); and random mesh patterns that have regular rhomboid shapes shown in FIG. 25(A) before the patterns are made to be irregular, have the different shapes and sizes (pitches p and angles θ) of the opening portions, are made to be irregular (random) in a predetermined range with angles maintained with respect to the pitches of the rhomboid shapes of the multiple regular rhomboid mesh patterns having different line widths of the thin metal lines (mesh), and have multiple parallelograms shown in FIG. 25(B). The combined mesh patterns 24, each of which is formed of the upper wiring pattern 24*a* and the lower wiring pattern 24*b* and which have different random shapes, are provided as simulation samples and actual samples, and the combined mesh pattern 24 and the BM pattern 38 of each color overlap with each other. With such a configuration, the indicator (quantitative value) of evaluation of moiré was obtained, and the three functional evaluators performed functional evaluation on moiré, which is caused by interference between both overlapping patterns in a simulation image of moiré, with their eyes.

Here, as shown in FIG. 16, regarding evaluation of moiré, functional evaluation was performed in the following manner: the image data of the combined mesh pattern created in step S12 was superposed on the luminance image data of the sub-pixel array pattern of each color of the pixel array (BM) pattern created in step S10; an inverse transform image of moiré, in which a transmittance image is superposed on a luminance image, was created, and was displayed on the display; and the three functional evaluators observed the displayed inverse transform image.

32 combinations, in which the line widths of the mesh, the resolution of the display, and the emission intensity of the display were different, were set as conditions 1 to 32. The conditions 1 to 32 are shown in Table 1.

Results thereof are shown in Table 2.

Here, the functional evaluation results were obtained in the following manner. The moiré is evaluated on 5 levels of 1 to 5. In a case where deterioration of visibility of moiré is observed and offers a strong sense of discomfort, the evaluation level is set to 1. In a case where deterioration of visibility of moiré is observed and offers a sense of discomfort, the evaluation level is set to 2. In a case where deterioration of visibility of moiré is observed and offers a weak sense of discomfort, the evaluation level is set to 3. In a case where deterioration of visibility of moiré is observed but does not offer a sense of discomfort, the evaluation level is set to 4. In a case where deterioration of visibility of moiré is not observed, the evaluation level is set to 5.

In terms of moiré visibility, moiré is allowable if the evaluation level is equal to or greater than 3. However, it is preferable that the evaluation level is equal to or greater than 4, and it is most preferable that the evaluation level is 5.

In the present example, the shape of the opening portion 22 of the mesh pattern 24 was changed such that the pitch p was changed to 100 µm and 150 µm and the angle θ was changed to 30° and 40°.

Further, the line width of the mesh pattern 24 was changed to 2 µm and 4 µm.

In addition, the resolutions of the displays using 8 types of the BM patterns shown in FIG. 15(A1) to 15(H1) respectively were 149 dpi, 222 dpi, 265 dpi, 265 dpi, 326 dpi, 384 dpi, 384 dpi, and 440 dpi.

Furthermore, when the entire range of the intensity was given as a range of 0 to 255, even in any display, the emission intensity of the display was changed to 64 (luminance 1) and 128 (luminance 2).

The irregularity (randomicity) was 0% (not applied), and was set to 5% and 8%.

For imaging the sub-pixel array pattern of each color of the pixel array (BM) pattern 38, STM6 (manufactured by OLYMPUS Corp.) was used as the microscope, UMPlanFl10x (manufactured by OLYMPUS Corp.) was used as the lens, and QIC-F-CLR-12-C (manufactured by QIMAGING Corp.) was used as the camera. Here, as the imaging conditions, for example, a gain was set to 1.0, and white balance (G, R, B) was set to (1.00, 2.17, 1.12). Further, the captured image was subjected to shading correction.

Calculation of the indicator (quantitative value) of evaluation of moiré was performed as described above in the method shown in FIG. 16.

TABLE 1

| CONDITION | MESH LINE WIDTH (µm) | DISPLAY RESOLUTION (dpi) | DISPLAY EMISSION INTENSITY (0-255) |
|---|---|---|---|
| 1 | 2 | 149 | 64 |
| 2 | 2 | 149 | 128 |
| 3 | 2 | 222 | 64 |
| 4 | 2 | 222 | 128 |
| 5 | 2 | 265 | 64 |
| 6 | 2 | 265 | 64 |
| 7 | 2 | 265 | 128 |
| 8 | 2 | 265 | 128 |
| 9 | 2 | 326 | 64 |
| 10 | 2 | 326 | 128 |
| 11 | 2 | 384 | 64 |
| 12 | 2 | 384 | 64 |
| 13 | 2 | 384 | 128 |
| 14 | 2 | 384 | 128 |
| 15 | 2 | 440 | 64 |
| 16 | 2 | 440 | 128 |
| 17 | 4 | 149 | 64 |
| 18 | 4 | 149 | 128 |
| 19 | 4 | 222 | 64 |
| 20 | 4 | 222 | 128 |
| 21 | 4 | 265 | 64 |
| 22 | 4 | 265 | 64 |
| 23 | 4 | 265 | 128 |
| 24 | 4 | 265 | 128 |
| 25 | 4 | 326 | 64 |
| 26 | 4 | 326 | 128 |
| 27 | 4 | 384 | 64 |
| 28 | 4 | 384 | 64 |
| 29 | 4 | 384 | 128 |
| 30 | 4 | 384 | 128 |
| 31 | 4 | 440 | 64 |
| 32 | 4 | 440 | 128 |

TABLE 2

| | CONDITION | RANDOMICITY [%] | ANGLE (°) | PITCH (µm) | QUANTITATIVE VALUE OF MOIRÉ | EVALUATION RESULT | |
|---|---|---|---|---|---|---|---|
| EXAMPLE 1 | 1 | 0 | 40 | 150 | −2.94 | 3 | REFERENCE EXAMPLE |
| EXAMPLE 2 | 1 | 4 | 40 | 150 | −3.05 | 3 | INVENTION EXAMPLE |
| EXAMPLE 3 | 1 | 8 | 40 | 150 | −3.11 | 3 | INVENTION EXAMPLE |
| EXAMPLE 4 | 1 | 0 | 40 | 100 | −3.16 | 3 | REFERENCE EXAMPLE |
| EXAMPLE 5 | 1 | 4 | 40 | 100 | −3.16 | 3 | INVENTION EXAMPLE |
| EXAMPLE 6 | 1 | 8 | 40 | 100 | −3.18 | 4 | INVENTION EXAMPLE |
| EXAMPLE 7 | 1 | 0 | 30 | 150 | −3.41 | 4 | REFERENCE EXAMPLE |
| EXAMPLE 8 | 1 | 4 | 30 | 150 | −3.41 | 4 | INVENTION EXAMPLE |
| EXAMPLE 9 | 1 | 8 | 30 | 150 | −3.43 | 4 | INVENTION EXAMPLE |
| EXAMPLE 10 | 1 | 4 | 30 | 100 | −3.52 | 4 | INVENTION EXAMPLE |
| EXAMPLE 11 | 1 | 0 | 30 | 100 | −3.84 | 4 | REFERENCE EXAMPLE |
| EXAMPLE 12 | 1 | 8 | 30 | 100 | −3.84 | 4 | INVENTION EXAMPLE |
| EXAMPLE 13 | 2 | 0 | 40 | 150 | −2.59 | 2 | COMPARATIVE EXAMPLE |
| EXAMPLE 14 | 2 | 4 | 40 | 150 | −2.74 | 2 | COMPARATIVE EXAMPLE |
| EXAMPLE 15 | 2 | 4 | 40 | 100 | −2.81 | 3 | INVENTION EXAMPLE |

TABLE 2-continued

| | CONDITION | RANDOMICITY [%] | ANGLE (°) | PITCH (μm) | QUANTITATIVE VALUE OF MOIRÉ | EVALUATION RESULT | |
|---|---|---|---|---|---|---|---|
| EXAMPLE 16 | 2 | 8 | 40 | 150 | −2.81 | 3 | INVENTION EXAMPLE |
| EXAMPLE 17 | 2 | 0 | 40 | 100 | −2.83 | 3 | REFERENCE EXAMPLE |
| EXAMPLE 18 | 2 | 8 | 40 | 100 | −2.83 | 3 | INVENTION EXAMPLE |
| EXAMPLE 19 | 2 | 0 | 30 | 150 | −2.93 | 3 | REFERENCE EXAMPLE |
| EXAMPLE 20 | 2 | 4 | 30 | 150 | −3.02 | 3 | INVENTION EXAMPLE |
| EXAMPLE 21 | 2 | 8 | 30 | 150 | −3.08 | 3 | INVENTION EXAMPLE |
| EXAMPLE 22 | 2 | 0 | 30 | 100 | −3.18 | 4 | REFERENCE EXAMPLE |
| EXAMPLE 23 | 2 | 4 | 30 | 100 | −3.20 | 4 | INVENTION EXAMPLE |
| EXAMPLE 24 | 2 | 8 | 30 | 100 | −3.23 | 4 | INVENTION EXAMPLE |
| EXAMPLE 25 | 3 | 0 | 30 | 100 | NaN | 5 | REFERENCE EXAMPLE |
| EXAMPLE 26 | 3 | 0 | 40 | 100 | NaN | 5 | REFERENCE EXAMPLE |
| EXAMPLE 27 | 3 | 0 | 30 | 150 | NaN | 5 | REFERENCE EXAMPLE |
| EXAMPLE 28 | 3 | 0 | 40 | 150 | NaN | 5 | REFERENCE EXAMPLE |
| EXAMPLE 29 | 3 | 4 | 30 | 100 | NaN | 5 | INVENTION EXAMPLE |
| EXAMPLE 30 | 3 | 4 | 40 | 100 | NaN | 5 | INVENTION EXAMPLE |
| EXAMPLE 31 | 3 | 4 | 30 | 150 | NaN | 5 | INVENTION EXAMPLE |
| EXAMPLE 32 | 3 | 4 | 40 | 150 | NaN | 5 | INVENTION EXAMPLE |
| EXAMPLE 33 | 3 | 8 | 30 | 100 | NaN | 5 | INVENTION EXAMPLE |
| EXAMPLE 34 | 3 | 8 | 40 | 100 | NaN | 5 | INVENTION EXAMPLE |
| EXAMPLE 35 | 3 | 8 | 30 | 150 | NaN | 5 | INVENTION EXAMPLE |
| EXAMPLE 36 | 3 | 8 | 40 | 150 | NaN | 5 | INVENTION EXAMPLE |
| EXAMPLE 37 | 4 | 0 | 30 | 100 | NaN | 5 | REFERENCE EXAMPLE |
| EXAMPLE 38 | 4 | 4 | 30 | 100 | NaN | 5 | INVENTION EXAMPLE |
| EXAMPLE 39 | 4 | 4 | 40 | 100 | NaN | 5 | INVENTION EXAMPLE |
| EXAMPLE 40 | 4 | 4 | 30 | 150 | NaN | 5 | INVENTION EXAMPLE |
| EXAMPLE 41 | 4 | 8 | 30 | 100 | NaN | 5 | INVENTION EXAMPLE |
| EXAMPLE 42 | 4 | 8 | 40 | 100 | NaN | 5 | INVENTION EXAMPLE |
| EXAMPLE 43 | 4 | 8 | 30 | 150 | NaN | 5 | INVENTION EXAMPLE |
| EXAMPLE 44 | 4 | 0 | 30 | 150 | −3.51 | 4 | REFERENCE EXAMPLE |
| EXAMPLE 45 | 4 | 0 | 40 | 150 | −3.58 | 4 | REFERENCE EXAMPLE |
| EXAMPLE 46 | 4 | 4 | 40 | 150 | −3.63 | 4 | INVENTION EXAMPLE |
| EXAMPLE 47 | 4 | 8 | 40 | 150 | −3.96 | 4 | INVENTION EXAMPLE |
| EXAMPLE 48 | 4 | 0 | 40 | 100 | −4.30 | 4 | REFERENCE EXAMPLE |
| EXAMPLE 49 | 5 | 0 | 40 | 150 | NaN | 5 | REFERENCE EXAMPLE |
| EXAMPLE 50 | 5 | 4 | 30 | 150 | NaN | 5 | INVENTION EXAMPLE |
| EXAMPLE 51 | 5 | 4 | 40 | 150 | NaN | 5 | INVENTION EXAMPLE |
| EXAMPLE 52 | 5 | 8 | 30 | 150 | NaN | 5 | INVENTION EXAMPLE |
| EXAMPLE 53 | 5 | 8 | 40 | 150 | NaN | 5 | INVENTION EXAMPLE |
| EXAMPLE 54 | 5 | 0 | 40 | 100 | −3.35 | 4 | REFERENCE EXAMPLE |
| EXAMPLE 55 | 5 | 0 | 30 | 100 | −3.39 | 4 | REFERENCE EXAMPLE |
| EXAMPLE 56 | 5 | 4 | 30 | 100 | −3.40 | 4 | INVENTION EXAMPLE |
| EXAMPLE 57 | 5 | 4 | 40 | 100 | −3.45 | 4 | INVENTION EXAMPLE |
| EXAMPLE 58 | 5 | 8 | 30 | 100 | −3.46 | 4 | INVENTION EXAMPLE |
| EXAMPLE 59 | 5 | 8 | 40 | 100 | −3.49 | 4 | INVENTION EXAMPLE |
| EXAMPLE 60 | 5 | 0 | 30 | 150 | −3.55 | 4 | REFERENCE EXAMPLE |
| EXAMPLE 61 | 6 | 8 | 30 | 150 | NaN | 5 | INVENTION EXAMPLE |
| EXAMPLE 62 | 6 | 0 | 40 | 100 | −2.91 | 3 | REFERENCE EXAMPLE |
| EXAMPLE 63 | 6 | 0 | 30 | 100 | −2.97 | 3 | REFERENCE EXAMPLE |
| EXAMPLE 64 | 6 | 4 | 30 | 100 | −2.98 | 3 | INVENTION EXAMPLE |
| EXAMPLE 65 | 6 | 4 | 40 | 100 | −3.02 | 3 | INVENTION EXAMPLE |
| EXAMPLE 66 | 6 | 8 | 30 | 100 | −3.04 | 3 | INVENTION EXAMPLE |
| EXAMPLE 67 | 6 | 8 | 40 | 100 | −3.05 | 3 | INVENTION EXAMPLE |
| EXAMPLE 68 | 6 | 0 | 30 | 150 | −3.13 | 3 | REFERENCE EXAMPLE |
| EXAMPLE 69 | 6 | 4 | 30 | 150 | −3.19 | 4 | INVENTION EXAMPLE |
| EXAMPLE 70 | 6 | 4 | 40 | 150 | −3.36 | 4 | INVENTION EXAMPLE |
| EXAMPLE 71 | 6 | 0 | 40 | 150 | −3.37 | 4 | REFERENCE EXAMPLE |
| EXAMPLE 72 | 6 | 8 | 40 | 150 | −3.42 | 4 | INVENTION EXAMPLE |
| EXAMPLE 73 | 7 | 0 | 40 | 100 | −3.01 | 3 | REFERENCE EXAMPLE |
| EXAMPLE 74 | 7 | 0 | 30 | 100 | −3.09 | 3 | REFERENCE EXAMPLE |
| EXAMPLE 75 | 7 | 4 | 30 | 100 | −3.10 | 3 | INVENTION EXAMPLE |
| EXAMPLE 76 | 7 | 4 | 40 | 100 | −3.15 | 3 | INVENTION EXAMPLE |
| EXAMPLE 77 | 7 | 8 | 30 | 100 | −3.16 | 3 | INVENTION EXAMPLE |
| EXAMPLE 78 | 7 | 8 | 40 | 100 | −3.19 | 4 | INVENTION EXAMPLE |
| EXAMPLE 79 | 7 | 0 | 30 | 150 | −3.25 | 4 | REFERENCE EXAMPLE |
| EXAMPLE 80 | 7 | 4 | 30 | 150 | −3.30 | 4 | INVENTION EXAMPLE |
| EXAMPLE 81 | 7 | 8 | 30 | 150 | −3.40 | 4 | INVENTION EXAMPLE |
| EXAMPLE 82 | 7 | 0 | 40 | 150 | −3.50 | 4 | REFERENCE EXAMPLE |
| EXAMPLE 83 | 7 | 4 | 40 | 150 | −3.50 | 4 | INVENTION EXAMPLE |
| EXAMPLE 84 | 7 | 8 | 40 | 150 | −3.56 | 4 | INVENTION EXAMPLE |
| EXAMPLE 85 | 8 | 8 | 30 | 150 | NaN | 5 | INVENTION EXAMPLE |
| EXAMPLE 86 | 8 | 0 | 30 | 100 | −2.52 | 1 | COMPARATIVE EXAMPLE |
| EXAMPLE 87 | 8 | 4 | 30 | 100 | −2.52 | 1 | COMPARATIVE EXAMPLE |
| EXAMPLE 88 | 8 | 8 | 30 | 100 | −2.57 | 1 | COMPARATIVE EXAMPLE |
| EXAMPLE 89 | 8 | 0 | 40 | 100 | −2.60 | 2 | COMPARATIVE EXAMPLE |
| EXAMPLE 90 | 8 | 4 | 40 | 100 | −2.72 | 2 | COMPARATIVE EXAMPLE |
| EXAMPLE 91 | 8 | 8 | 40 | 100 | −2.76 | 2 | COMPARATIVE EXAMPLE |

TABLE 2-continued

| | CONDITION | RANDOMICITY [%] | ANGLE (°) | PITCH (μm) | QUANTITATIVE VALUE OF MOIRÉ | EVALUATION RESULT | |
|---|---|---|---|---|---|---|---|
| EXAMPLE 92 | 8 | 0 | 30 | 150 | −2.83 | 3 | REFERENCE EXAMPLE |
| EXAMPLE 93 | 8 | 4 | 30 | 150 | −2.88 | 3 | INVENTION EXAMPLE |
| EXAMPLE 94 | 8 | 4 | 40 | 150 | −3.06 | 3 | INVENTION EXAMPLE |
| EXAMPLE 95 | 8 | 0 | 40 | 150 | −3.06 | 3 | REFERENCE EXAMPLE |
| EXAMPLE 96 | 8 | 8 | 40 | 150 | −3.12 | 3 | INVENTION EXAMPLE |
| EXAMPLE 97 | 9 | 8 | 30 | 150 | NaN | 5 | INVENTION EXAMPLE |
| EXAMPLE 98 | 9 | 0 | 30 | 100 | −3.28 | 4 | REFERENCE EXAMPLE |
| EXAMPLE 99 | 9 | 0 | 40 | 150 | −3.31 | 4 | REFERENCE EXAMPLE |
| EXAMPLE 100 | 9 | 4 | 30 | 100 | −3.36 | 4 | INVENTION EXAMPLE |
| EXAMPLE 101 | 9 | 4 | 40 | 100 | −3.44 | 4 | INVENTION EXAMPLE |
| EXAMPLE 102 | 9 | 8 | 30 | 100 | −3.45 | 4 | INVENTION EXAMPLE |
| EXAMPLE 103 | 9 | 0 | 40 | 100 | −3.76 | 4 | REFERENCE EXAMPLE |
| EXAMPLE 104 | 9 | 0 | 30 | 150 | −3.77 | 4 | REFERENCE EXAMPLE |
| EXAMPLE 105 | 9 | 4 | 40 | 100 | −3.81 | 4 | INVENTION EXAMPLE |
| EXAMPLE 106 | 9 | 8 | 40 | 150 | −3.82 | 4 | INVENTION EXAMPLE |
| EXAMPLE 107 | 9 | 8 | 40 | 100 | −3.89 | 4 | INVENTION EXAMPLE |
| EXAMPLE 108 | 9 | 4 | 30 | 150 | −4.31 | 4 | INVENTION EXAMPLE |
| EXAMPLE 109 | 10 | 8 | 30 | 150 | NaN | 5 | INVENTION EXAMPLE |
| EXAMPLE 110 | 10 | 0 | 30 | 100 | −2.98 | 3 | REFERENCE EXAMPLE |
| EXAMPLE 111 | 10 | 0 | 40 | 150 | −3.01 | 3 | REFERENCE EXAMPLE |
| EXAMPLE 112 | 10 | 4 | 30 | 100 | −3.06 | 3 | INVENTION EXAMPLE |
| EXAMPLE 113 | 10 | 4 | 40 | 150 | −3.13 | 3 | INVENTION EXAMPLE |
| EXAMPLE 114 | 10 | 8 | 30 | 100 | −3.17 | 4 | INVENTION EXAMPLE |
| EXAMPLE 115 | 10 | 0 | 30 | 150 | −3.39 | 4 | REFERENCE EXAMPLE |
| EXAMPLE 116 | 10 | 0 | 40 | 100 | −3.46 | 4 | REFERENCE EXAMPLE |
| EXAMPLE 117 | 10 | 8 | 40 | 150 | −3.52 | 4 | INVENTION EXAMPLE |
| EXAMPLE 118 | 10 | 4 | 40 | 100 | −3.52 | 4 | INVENTION EXAMPLE |
| EXAMPLE 119 | 10 | 8 | 40 | 100 | −3.59 | 4 | INVENTION EXAMPLE |
| EXAMPLE 120 | 10 | 4 | 30 | 150 | −3.71 | 4 | INVENTION EXAMPLE |
| EXAMPLE 121 | 11 | 4 | 30 | 150 | NaN | 5 | INVENTION EXAMPLE |
| EXAMPLE 122 | 11 | 8 | 30 | 150 | NaN | 5 | INVENTION EXAMPLE |
| EXAMPLE 123 | 11 | 0 | 40 | 100 | −2.51 | 1 | COMPARATIVE EXAMPLE |
| EXAMPLE 124 | 11 | 4 | 40 | 100 | −2.54 | 1 | COMPARATIVE EXAMPLE |
| EXAMPLE 125 | 11 | 8 | 40 | 100 | −2.56 | 1 | COMPARATIVE EXAMPLE |
| EXAMPLE 126 | 11 | 0 | 40 | 150 | −2.76 | 2 | COMPARATIVE EXAMPLE |
| EXAMPLE 127 | 11 | 4 | 40 | 150 | −2.88 | 3 | INVENTION EXAMPLE |
| EXAMPLE 128 | 11 | 8 | 40 | 150 | −2.91 | 3 | INVENTION EXAMPLE |
| EXAMPLE 129 | 11 | 0 | 30 | 100 | −3.58 | 4 | REFERENCE EXAMPLE |
| EXAMPLE 130 | 11 | 4 | 30 | 100 | −3.96 | 4 | INVENTION EXAMPLE |
| EXAMPLE 131 | 11 | 8 | 30 | 100 | −3.97 | 4 | INVENTION EXAMPLE |
| EXAMPLE 132 | 11 | 0 | 30 | 150 | −4.15 | 4 | REFERENCE EXAMPLE |
| EXAMPLE 133 | 12 | 0 | 30 | 150 | NaN | 5 | REFERENCE EXAMPLE |
| EXAMPLE 134 | 12 | 4 | 30 | 150 | NaN | 5 | INVENTION EXAMPLE |
| EXAMPLE 135 | 12 | 8 | 30 | 150 | NaN | 5 | INVENTION EXAMPLE |
| EXAMPLE 136 | 12 | 8 | 40 | 150 | NaN | 5 | INVENTION EXAMPLE |
| EXAMPLE 137 | 12 | 0 | 40 | 100 | −3.32 | 4 | REFERENCE EXAMPLE |
| EXAMPLE 138 | 12 | 4 | 40 | 100 | −3.38 | 4 | INVENTION EXAMPLE |
| EXAMPLE 139 | 12 | 0 | 30 | 100 | −3.42 | 4 | REFERENCE EXAMPLE |
| EXAMPLE 140 | 12 | 8 | 40 | 100 | −3.44 | 4 | INVENTION EXAMPLE |
| EXAMPLE 141 | 12 | 4 | 30 | 100 | −3.53 | 4 | INVENTION EXAMPLE |
| EXAMPLE 142 | 12 | 0 | 40 | 150 | −3.55 | 4 | REFERENCE EXAMPLE |
| EXAMPLE 143 | 12 | 4 | 40 | 150 | −3.57 | 4 | INVENTION EXAMPLE |
| EXAMPLE 144 | 12 | 8 | 30 | 100 | −3.67 | 4 | INVENTION EXAMPLE |
| EXAMPLE 145 | 13 | 0 | 40 | 100 | −2.21 | 1 | COMPARATIVE EXAMPLE |
| EXAMPLE 146 | 13 | 4 | 40 | 100 | −2.24 | 1 | COMPARATIVE EXAMPLE |
| EXAMPLE 147 | 13 | 8 | 40 | 100 | −2.26 | 1 | COMPARATIVE EXAMPLE |
| EXAMPLE 148 | 13 | 0 | 40 | 150 | −2.45 | 1 | COMPARATIVE EXAMPLE |
| EXAMPLE 149 | 13 | 4 | 40 | 150 | −2.58 | 1 | COMPARATIVE EXAMPLE |
| EXAMPLE 150 | 13 | 8 | 40 | 150 | −2.61 | 2 | COMPARATIVE EXAMPLE |
| EXAMPLE 151 | 13 | 0 | 30 | 100 | −3.28 | 4 | REFERENCE EXAMPLE |
| EXAMPLE 152 | 13 | 4 | 30 | 100 | −3.35 | 4 | INVENTION EXAMPLE |
| EXAMPLE 153 | 13 | 8 | 30 | 100 | −3.43 | 4 | INVENTION EXAMPLE |
| EXAMPLE 154 | 13 | 0 | 30 | 150 | −3.76 | 4 | REFERENCE EXAMPLE |
| EXAMPLE 155 | 13 | 4 | 30 | 150 | −3.98 | 4 | INVENTION EXAMPLE |
| EXAMPLE 156 | 13 | 8 | 30 | 150 | −4.02 | 4 | INVENTION EXAMPLE |
| EXAMPLE 157 | 14 | 4 | 30 | 150 | NaN | 5 | INVENTION EXAMPLE |
| EXAMPLE 158 | 14 | 8 | 30 | 150 | NaN | 5 | INVENTION EXAMPLE |
| EXAMPLE 159 | 14 | 8 | 40 | 150 | NaN | 5 | INVENTION EXAMPLE |
| EXAMPLE 160 | 14 | 0 | 40 | 100 | −3.02 | 3 | REFERENCE EXAMPLE |
| EXAMPLE 161 | 14 | 4 | 40 | 100 | −3.08 | 3 | INVENTION EXAMPLE |
| EXAMPLE 162 | 14 | 0 | 30 | 100 | −3.12 | 3 | REFERENCE EXAMPLE |
| EXAMPLE 163 | 14 | 8 | 40 | 100 | −3.15 | 3 | INVENTION EXAMPLE |
| EXAMPLE 164 | 14 | 4 | 30 | 100 | −3.23 | 4 | INVENTION EXAMPLE |
| EXAMPLE 165 | 14 | 0 | 40 | 150 | −3.24 | 4 | REFERENCE EXAMPLE |
| EXAMPLE 166 | 14 | 4 | 40 | 150 | −3.27 | 4 | INVENTION EXAMPLE |
| EXAMPLE 167 | 14 | 8 | 30 | 100 | −3.37 | 4 | INVENTION EXAMPLE |

TABLE 2-continued

| | CONDITION | RANDOMICITY [%] | ANGLE (°) | PITCH (μm) | QUANTITATIVE VALUE OF MOIRÉ | EVALUATION RESULT | |
|---|---|---|---|---|---|---|---|
| EXAMPLE 168 | 14 | 0 | 30 | 150 | −4.47 | 4 | REFERENCE EXAMPLE |
| EXAMPLE 169 | 15 | 0 | 30 | 100 | NaN | 5 | REFERENCE EXAMPLE |
| EXAMPLE 170 | 15 | 4 | 30 | 100 | NaN | 5 | INVENTION EXAMPLE |
| EXAMPLE 171 | 15 | 4 | 40 | 150 | NaN | 5 | INVENTION EXAMPLE |
| EXAMPLE 172 | 15 | 8 | 30 | 100 | NaN | 5 | INVENTION EXAMPLE |
| EXAMPLE 173 | 15 | 8 | 40 | 100 | NaN | 5 | INVENTION EXAMPLE |
| EXAMPLE 174 | 15 | 8 | 30 | 150 | NaN | 5 | INVENTION EXAMPLE |
| EXAMPLE 175 | 15 | 8 | 40 | 150 | NaN | 5 | INVENTION EXAMPLE |
| EXAMPLE 176 | 15 | 0 | 40 | 100 | −3.73 | 4 | REFERENCE EXAMPLE |
| EXAMPLE 177 | 15 | 0 | 30 | 150 | −3.73 | 4 | REFERENCE EXAMPLE |
| EXAMPLE 178 | 15 | 0 | 40 | 150 | −3.94 | 4 | REFERENCE EXAMPLE |
| EXAMPLE 179 | 15 | 4 | 40 | 100 | −4.06 | 4 | INVENTION EXAMPLE |
| EXAMPLE 180 | 15 | 4 | 30 | 150 | −4.19 | 4 | INVENTION EXAMPLE |
| EXAMPLE 181 | 16 | 0 | 30 | 100 | NaN | 5 | REFERENCE EXAMPLE |
| EXAMPLE 182 | 16 | 4 | 30 | 100 | NaN | 5 | INVENTION EXAMPLE |
| EXAMPLE 183 | 16 | 8 | 30 | 100 | NaN | 5 | INVENTION EXAMPLE |
| EXAMPLE 184 | 16 | 8 | 30 | 150 | NaN | 5 | INVENTION EXAMPLE |
| EXAMPLE 185 | 16 | 0 | 30 | 150 | −3.03 | 3 | REFERENCE EXAMPLE |
| EXAMPLE 186 | 16 | 0 | 40 | 100 | −3.36 | 4 | REFERENCE EXAMPLE |
| EXAMPLE 187 | 16 | 0 | 40 | 150 | −3.37 | 4 | REFERENCE EXAMPLE |
| EXAMPLE 188 | 16 | 4 | 40 | 150 | −3.46 | 4 | INVENTION EXAMPLE |
| EXAMPLE 189 | 16 | 8 | 40 | 150 | −3.59 | 4 | INVENTION EXAMPLE |
| EXAMPLE 190 | 16 | 4 | 30 | 150 | −3.61 | 4 | INVENTION EXAMPLE |
| EXAMPLE 191 | 16 | 4 | 40 | 100 | −3.69 | 4 | INVENTION EXAMPLE |
| EXAMPLE 192 | 16 | 8 | 40 | 100 | −3.71 | 4 | INVENTION EXAMPLE |
| EXAMPLE 193 | 17 | 0 | 40 | 150 | −2.67 | 2 | COMPARATIVE EXAMPLE |
| EXAMPLE 194 | 17 | 4 | 40 | 150 | −2.75 | 2 | COMPARATIVE EXAMPLE |
| EXAMPLE 195 | 17 | 8 | 40 | 150 | −2.77 | 2 | COMPARATIVE EXAMPLE |
| EXAMPLE 196 | 17 | 4 | 40 | 100 | −2.82 | 3 | INVENTION EXAMPLE |
| EXAMPLE 197 | 17 | 0 | 40 | 100 | −2.84 | 3 | REFERENCE EXAMPLE |
| EXAMPLE 198 | 17 | 8 | 40 | 100 | −2.84 | 3 | INVENTION EXAMPLE |
| EXAMPLE 199 | 17 | 0 | 30 | 150 | −2.97 | 3 | REFERENCE EXAMPLE |
| EXAMPLE 200 | 17 | 4 | 30 | 150 | −3.03 | 3 | INVENTION EXAMPLE |
| EXAMPLE 201 | 17 | 8 | 30 | 150 | −3.05 | 3 | INVENTION EXAMPLE |
| EXAMPLE 202 | 17 | 0 | 30 | 100 | −3.19 | 4 | REFERENCE EXAMPLE |
| EXAMPLE 203 | 17 | 4 | 30 | 100 | −3.21 | 4 | INVENTION EXAMPLE |
| EXAMPLE 204 | 17 | 8 | 30 | 100 | −3.24 | 4 | INVENTION EXAMPLE |
| EXAMPLE 205 | 18 | 0 | 40 | 150 | −2.33 | 1 | COMPARATIVE EXAMPLE |
| EXAMPLE 206 | 18 | 4 | 40 | 150 | −2.40 | 1 | COMPARATIVE EXAMPLE |
| EXAMPLE 207 | 18 | 8 | 40 | 150 | −2.43 | 1 | COMPARATIVE EXAMPLE |
| EXAMPLE 208 | 18 | 4 | 40 | 100 | −2.49 | 1 | COMPARATIVE EXAMPLE |
| EXAMPLE 209 | 18 | 0 | 40 | 100 | −2.51 | 1 | COMPARATIVE EXAMPLE |
| EXAMPLE 210 | 18 | 8 | 40 | 100 | −2.51 | 1 | COMPARATIVE EXAMPLE |
| EXAMPLE 211 | 18 | 0 | 30 | 150 | −2.62 | 2 | COMPARATIVE EXAMPLE |
| EXAMPLE 212 | 18 | 4 | 30 | 150 | −2.69 | 2 | COMPARATIVE EXAMPLE |
| EXAMPLE 213 | 18 | 0 | 30 | 100 | −2.72 | 2 | COMPARATIVE EXAMPLE |
| EXAMPLE 214 | 18 | 8 | 30 | 150 | −2.72 | 2 | COMPARATIVE EXAMPLE |
| EXAMPLE 215 | 18 | 4 | 30 | 100 | −2.73 | 2 | COMPARATIVE EXAMPLE |
| EXAMPLE 216 | 18 | 8 | 30 | 100 | −2.77 | 2 | COMPARATIVE EXAMPLE |
| EXAMPLE 217 | 19 | 0 | 40 | 100 | NaN | 5 | REFERENCE EXAMPLE |
| EXAMPLE 218 | 19 | 0 | 30 | 150 | NaN | 5 | REFERENCE EXAMPLE |
| EXAMPLE 219 | 19 | 4 | 40 | 100 | NaN | 5 | INVENTION EXAMPLE |
| EXAMPLE 220 | 19 | 4 | 30 | 150 | NaN | 5 | INVENTION EXAMPLE |
| EXAMPLE 221 | 19 | 8 | 40 | 100 | NaN | 5 | INVENTION EXAMPLE |
| EXAMPLE 222 | 19 | 8 | 30 | 150 | NaN | 5 | INVENTION EXAMPLE |
| EXAMPLE 223 | 19 | 8 | 40 | 150 | NaN | 5 | INVENTION EXAMPLE |
| EXAMPLE 224 | 19 | 0 | 30 | 100 | −3.14 | 3 | REFERENCE EXAMPLE |
| EXAMPLE 225 | 19 | 4 | 30 | 100 | −3.28 | 4 | INVENTION EXAMPLE |
| EXAMPLE 226 | 19 | 8 | 30 | 100 | −3.35 | 4 | INVENTION EXAMPLE |
| EXAMPLE 227 | 19 | 0 | 40 | 150 | −3.59 | 4 | REFERENCE EXAMPLE |
| EXAMPLE 228 | 19 | 4 | 40 | 150 | −3.63 | 4 | INVENTION EXAMPLE |
| EXAMPLE 229 | 20 | 0 | 30 | 100 | −2.73 | 2 | COMPARATIVE EXAMPLE |
| EXAMPLE 230 | 20 | 4 | 30 | 100 | −2.99 | 3 | INVENTION EXAMPLE |
| EXAMPLE 231 | 20 | 8 | 30 | 100 | −3.05 | 3 | INVENTION EXAMPLE |
| EXAMPLE 232 | 20 | 0 | 40 | 100 | −3.09 | 3 | REFERENCE EXAMPLE |
| EXAMPLE 233 | 20 | 4 | 40 | 100 | −3.14 | 3 | INVENTION EXAMPLE |
| EXAMPLE 234 | 20 | 0 | 30 | 150 | −3.17 | 4 | REFERENCE EXAMPLE |
| EXAMPLE 235 | 20 | 8 | 40 | 100 | −3.23 | 4 | INVENTION EXAMPLE |
| EXAMPLE 236 | 20 | 0 | 40 | 150 | −3.29 | 4 | REFERENCE EXAMPLE |
| EXAMPLE 237 | 20 | 4 | 40 | 150 | −3.33 | 4 | INVENTION EXAMPLE |
| EXAMPLE 238 | 20 | 4 | 30 | 150 | −3.35 | 4 | INVENTION EXAMPLE |
| EXAMPLE 239 | 20 | 8 | 40 | 150 | −3.38 | 4 | INVENTION EXAMPLE |
| EXAMPLE 240 | 20 | 8 | 30 | 150 | −3.46 | 4 | INVENTION EXAMPLE |
| EXAMPLE 241 | 21 | 0 | 30 | 100 | −2.99 | 3 | REFERENCE EXAMPLE |
| EXAMPLE 242 | 21 | 4 | 30 | 100 | −3.01 | 3 | INVENTION EXAMPLE |
| EXAMPLE 243 | 21 | 0 | 40 | 100 | −3.03 | 3 | REFERENCE EXAMPLE |

TABLE 2-continued

| | CONDITION | RANDOMICITY [%] | ANGLE (°) | PITCH (μm) | QUANTITATIVE VALUE OF MOIRÉ | EVALUATION RESULT | |
|---|---|---|---|---|---|---|---|
| EXAMPLE 244 | 21 | 8 | 30 | 100 | −3.06 | 3 | INVENTION EXAMPLE |
| EXAMPLE 245 | 21 | 4 | 40 | 100 | −3.16 | 3 | INVENTION EXAMPLE |
| EXAMPLE 246 | 21 | 8 | 40 | 100 | −3.20 | 4 | INVENTION EXAMPLE |
| EXAMPLE 247 | 21 | 0 | 30 | 150 | −3.26 | 4 | REFERENCE EXAMPLE |
| EXAMPLE 248 | 21 | 4 | 30 | 150 | −3.32 | 4 | INVENTION EXAMPLE |
| EXAMPLE 249 | 21 | 8 | 30 | 150 | −3.46 | 4 | INVENTION EXAMPLE |
| EXAMPLE 250 | 21 | 4 | 40 | 150 | −3.51 | 4 | INVENTION EXAMPLE |
| EXAMPLE 251 | 21 | 0 | 40 | 150 | −3.51 | 4 | REFERENCE EXAMPLE |
| EXAMPLE 252 | 21 | 8 | 40 | 150 | −3.58 | 4 | INVENTION EXAMPLE |
| EXAMPLE 253 | 22 | 0 | 40 | 100 | −2.67 | 2 | COMPARATIVE EXAMPLE |
| EXAMPLE 254 | 22 | 0 | 30 | 100 | −2.68 | 2 | COMPARATIVE EXAMPLE |
| EXAMPLE 255 | 22 | 4 | 30 | 100 | −2.69 | 2 | COMPARATIVE EXAMPLE |
| EXAMPLE 256 | 22 | 4 | 40 | 100 | −2.73 | 2 | COMPARATIVE EXAMPLE |
| EXAMPLE 257 | 22 | 8 | 30 | 100 | −2.74 | 2 | COMPARATIVE EXAMPLE |
| EXAMPLE 258 | 22 | 8 | 40 | 100 | −2.76 | 2 | COMPARATIVE EXAMPLE |
| EXAMPLE 259 | 22 | 0 | 30 | 150 | −2.84 | 3 | REFERENCE EXAMPLE |
| EXAMPLE 260 | 22 | 4 | 30 | 150 | −2.88 | 3 | INVENTION EXAMPLE |
| EXAMPLE 261 | 22 | 8 | 30 | 150 | −3.03 | 3 | INVENTION EXAMPLE |
| EXAMPLE 262 | 22 | 4 | 40 | 150 | −3.07 | 3 | INVENTION EXAMPLE |
| EXAMPLE 263 | 22 | 0 | 40 | 150 | −3.07 | 3 | REFERENCE EXAMPLE |
| EXAMPLE 264 | 22 | 8 | 40 | 150 | −3.13 | 3 | INVENTION EXAMPLE |
| EXAMPLE 265 | 23 | 0 | 30 | 100 | −2.65 | 2 | COMPARATIVE EXAMPLE |
| EXAMPLE 266 | 23 | 4 | 30 | 100 | −2.68 | 2 | COMPARATIVE EXAMPLE |
| EXAMPLE 267 | 23 | 0 | 40 | 100 | −2.70 | 2 | COMPARATIVE EXAMPLE |
| EXAMPLE 268 | 23 | 8 | 30 | 100 | −2.76 | 2 | COMPARATIVE EXAMPLE |
| EXAMPLE 269 | 23 | 4 | 40 | 100 | −2.77 | 2 | COMPARATIVE EXAMPLE |
| EXAMPLE 270 | 23 | 8 | 40 | 100 | −2.83 | 3 | INVENTION EXAMPLE |
| EXAMPLE 271 | 23 | 0 | 30 | 150 | −2.92 | 3 | REFERENCE EXAMPLE |
| EXAMPLE 272 | 23 | 4 | 30 | 150 | −3.02 | 3 | INVENTION EXAMPLE |
| EXAMPLE 273 | 23 | 8 | 30 | 150 | −3.16 | 3 | INVENTION EXAMPLE |
| EXAMPLE 274 | 23 | 4 | 40 | 150 | −3.21 | 4 | INVENTION EXAMPLE |
| EXAMPLE 275 | 23 | 0 | 40 | 150 | −3.21 | 4 | REFERENCE EXAMPLE |
| EXAMPLE 276 | 23 | 8 | 40 | 150 | −3.26 | 4 | INVENTION EXAMPLE |
| EXAMPLE 277 | 24 | 0 | 30 | 100 | −2.17 | 1 | COMPARATIVE EXAMPLE |
| EXAMPLE 278 | 24 | 4 | 30 | 100 | −2.18 | 1 | COMPARATIVE EXAMPLE |
| EXAMPLE 279 | 24 | 8 | 30 | 100 | −2.23 | 1 | COMPARATIVE EXAMPLE |
| EXAMPLE 280 | 24 | 0 | 40 | 100 | −2.34 | 1 | COMPARATIVE EXAMPLE |
| EXAMPLE 281 | 24 | 4 | 40 | 100 | −2.38 | 1 | COMPARATIVE EXAMPLE |
| EXAMPLE 282 | 24 | 8 | 40 | 100 | −2.44 | 1 | COMPARATIVE EXAMPLE |
| EXAMPLE 283 | 24 | 0 | 30 | 150 | −2.52 | 1 | COMPARATIVE EXAMPLE |
| EXAMPLE 284 | 24 | 4 | 30 | 150 | −2.59 | 1 | COMPARATIVE EXAMPLE |
| EXAMPLE 285 | 24 | 0 | 40 | 150 | −2.70 | 2 | COMPARATIVE EXAMPLE |
| EXAMPLE 286 | 24 | 4 | 40 | 150 | −2.72 | 2 | COMPARATIVE EXAMPLE |
| EXAMPLE 287 | 24 | 8 | 30 | 150 | −2.73 | 2 | COMPARATIVE EXAMPLE |
| EXAMPLE 288 | 24 | 8 | 40 | 150 | −2.82 | 3 | INVENTION EXAMPLE |
| EXAMPLE 289 | 25 | 0 | 40 | 100 | −2.92 | 3 | REFERENCE EXAMPLE |
| EXAMPLE 290 | 25 | 4 | 40 | 100 | −2.93 | 3 | INVENTION EXAMPLE |
| EXAMPLE 291 | 25 | 0 | 40 | 150 | −3.02 | 3 | REFERENCE EXAMPLE |
| EXAMPLE 292 | 25 | 4 | 30 | 100 | −3.08 | 3 | INVENTION EXAMPLE |
| EXAMPLE 293 | 25 | 0 | 30 | 100 | −3.10 | 3 | REFERENCE EXAMPLE |
| EXAMPLE 294 | 25 | 8 | 40 | 100 | −3.11 | 3 | INVENTION EXAMPLE |
| EXAMPLE 295 | 25 | 4 | 40 | 150 | −3.12 | 3 | INVENTION EXAMPLE |
| EXAMPLE 296 | 25 | 8 | 30 | 100 | −3.15 | 3 | INVENTION EXAMPLE |
| EXAMPLE 297 | 25 | 8 | 40 | 150 | −3.25 | 4 | INVENTION EXAMPLE |
| EXAMPLE 298 | 25 | 0 | 30 | 150 | −3.47 | 4 | REFERENCE EXAMPLE |
| EXAMPLE 299 | 25 | 4 | 30 | 150 | −3.57 | 4 | INVENTION EXAMPLE |
| EXAMPLE 300 | 25 | 8 | 30 | 150 | −3.91 | 4 | INVENTION EXAMPLE |
| EXAMPLE 301 | 26 | 0 | 40 | 100 | −2.61 | 2 | COMPARATIVE EXAMPLE |
| EXAMPLE 302 | 26 | 4 | 40 | 100 | −2.63 | 2 | COMPARATIVE EXAMPLE |
| EXAMPLE 303 | 26 | 8 | 40 | 100 | −2.69 | 2 | COMPARATIVE EXAMPLE |
| EXAMPLE 304 | 26 | 0 | 40 | 150 | −2.71 | 2 | COMPARATIVE EXAMPLE |
| EXAMPLE 305 | 26 | 4 | 30 | 100 | −2.77 | 2 | COMPARATIVE EXAMPLE |
| EXAMPLE 306 | 26 | 0 | 30 | 100 | −2.78 | 2 | COMPARATIVE EXAMPLE |
| EXAMPLE 307 | 26 | 4 | 40 | 150 | −2.80 | 3 | INVENTION EXAMPLE |
| EXAMPLE 308 | 26 | 8 | 30 | 100 | −2.86 | 3 | INVENTION EXAMPLE |
| EXAMPLE 309 | 26 | 8 | 40 | 150 | −2.95 | 3 | INVENTION EXAMPLE |
| EXAMPLE 310 | 26 | 0 | 30 | 150 | −3.16 | 3 | REFERENCE EXAMPLE |
| EXAMPLE 311 | 26 | 4 | 30 | 150 | −3.27 | 4 | INVENTION EXAMPLE |
| EXAMPLE 312 | 26 | 8 | 30 | 150 | −3.62 | 4 | INVENTION EXAMPLE |
| EXAMPLE 313 | 27 | 0 | 40 | 100 | −2.22 | 1 | COMPARATIVE EXAMPLE |
| EXAMPLE 314 | 27 | 4 | 40 | 100 | −2.25 | 1 | COMPARATIVE EXAMPLE |
| EXAMPLE 315 | 27 | 8 | 40 | 100 | −2.27 | 1 | COMPARATIVE EXAMPLE |
| EXAMPLE 316 | 27 | 0 | 40 | 150 | −2.46 | 1 | COMPARATIVE EXAMPLE |
| EXAMPLE 317 | 27 | 4 | 40 | 150 | −2.56 | 1 | COMPARATIVE EXAMPLE |
| EXAMPLE 318 | 27 | 8 | 40 | 150 | −2.62 | 2 | COMPARATIVE EXAMPLE |
| EXAMPLE 319 | 27 | 0 | 30 | 100 | −3.30 | 4 | REFERENCE EXAMPLE |

TABLE 2-continued

| | CONDITION | RANDOMICITY [%] | ANGLE (°) | PITCH (μm) | QUANTITATIVE VALUE OF MOIRÉ | EVALUATION RESULT | |
|---|---|---|---|---|---|---|---|
| EXAMPLE 320 | 27 | 4 | 30 | 100 | −3.36 | 4 | INVENTION EXAMPLE |
| EXAMPLE 321 | 27 | 8 | 30 | 100 | −3.42 | 4 | INVENTION EXAMPLE |
| EXAMPLE 322 | 27 | 0 | 30 | 150 | −3.85 | 4 | REFERENCE EXAMPLE |
| EXAMPLE 323 | 27 | 4 | 30 | 150 | −3.99 | 4 | INVENTION EXAMPLE |
| EXAMPLE 324 | 27 | 8 | 30 | 150 | −4.02 | 4 | INVENTION EXAMPLE |
| EXAMPLE 325 | 28 | 4 | 30 | 150 | NaN | 5 | INVENTION EXAMPLE |
| EXAMPLE 326 | 28 | 8 | 30 | 150 | NaN | 5 | INVENTION EXAMPLE |
| EXAMPLE 327 | 28 | 0 | 40 | 100 | −3.03 | 3 | REFERENCE EXAMPLE |
| EXAMPLE 328 | 28 | 4 | 40 | 100 | −3.09 | 3 | INVENTION EXAMPLE |
| EXAMPLE 329 | 28 | 0 | 30 | 100 | −3.14 | 3 | REFERENCE EXAMPLE |
| EXAMPLE 330 | 28 | 8 | 40 | 100 | −3.16 | 3 | INVENTION EXAMPLE |
| EXAMPLE 331 | 28 | 4 | 30 | 100 | −3.25 | 4 | INVENTION EXAMPLE |
| EXAMPLE 332 | 28 | 0 | 40 | 150 | −3.25 | 4 | REFERENCE EXAMPLE |
| EXAMPLE 333 | 28 | 4 | 40 | 150 | −3.28 | 4 | INVENTION EXAMPLE |
| EXAMPLE 334 | 28 | 8 | 30 | 100 | −3.39 | 4 | INVENTION EXAMPLE |
| EXAMPLE 335 | 28 | 8 | 40 | 150 | −3.44 | 4 | INVENTION EXAMPLE |
| EXAMPLE 336 | 28 | 0 | 30 | 150 | −4.06 | 4 | REFERENCE EXAMPLE |
| EXAMPLE 337 | 29 | 0 | 40 | 100 | −1.91 | 1 | COMPARATIVE EXAMPLE |
| EXAMPLE 338 | 29 | 4 | 40 | 100 | −1.93 | 1 | COMPARATIVE EXAMPLE |
| EXAMPLE 339 | 29 | 8 | 40 | 100 | −1.95 | 1 | COMPARATIVE EXAMPLE |
| EXAMPLE 340 | 29 | 0 | 40 | 150 | −2.16 | 1 | COMPARATIVE EXAMPLE |
| EXAMPLE 341 | 29 | 4 | 40 | 150 | −2.25 | 1 | COMPARATIVE EXAMPLE |
| EXAMPLE 342 | 29 | 8 | 40 | 150 | −2.30 | 1 | COMPARATIVE EXAMPLE |
| EXAMPLE 343 | 29 | 0 | 30 | 100 | −3.00 | 3 | REFERENCE EXAMPLE |
| EXAMPLE 344 | 29 | 4 | 30 | 100 | −3.06 | 3 | INVENTION EXAMPLE |
| EXAMPLE 345 | 29 | 8 | 30 | 100 | −3.15 | 3 | INVENTION EXAMPLE |
| EXAMPLE 346 | 29 | 0 | 30 | 150 | −3.43 | 4 | REFERENCE EXAMPLE |
| EXAMPLE 347 | 29 | 4 | 30 | 150 | −3.59 | 4 | INVENTION EXAMPLE |
| EXAMPLE 348 | 29 | 8 | 30 | 150 | −3.62 | 4 | INVENTION EXAMPLE |
| EXAMPLE 349 | 30 | 8 | 30 | 150 | NaN | 5 | INVENTION EXAMPLE |
| EXAMPLE 350 | 30 | 0 | 40 | 100 | −2.58 | 1 | COMPARATIVE EXAMPLE |
| EXAMPLE 351 | 30 | 4 | 40 | 100 | −2.69 | 2 | COMPARATIVE EXAMPLE |
| EXAMPLE 352 | 30 | 8 | 40 | 100 | −2.75 | 2 | COMPARATIVE EXAMPLE |
| EXAMPLE 353 | 30 | 0 | 30 | 100 | −2.76 | 2 | COMPARATIVE EXAMPLE |
| EXAMPLE 354 | 30 | 4 | 30 | 100 | −2.90 | 3 | INVENTION EXAMPLE |
| EXAMPLE 355 | 30 | 0 | 40 | 150 | −2.95 | 3 | REFERENCE EXAMPLE |
| EXAMPLE 356 | 30 | 4 | 40 | 150 | −2.98 | 3 | INVENTION EXAMPLE |
| EXAMPLE 357 | 30 | 8 | 30 | 100 | −3.09 | 3 | INVENTION EXAMPLE |
| EXAMPLE 358 | 30 | 8 | 40 | 150 | −3.14 | 3 | INVENTION EXAMPLE |
| EXAMPLE 359 | 30 | 0 | 30 | 150 | −3.63 | 4 | REFERENCE EXAMPLE |
| EXAMPLE 360 | 30 | 4 | 30 | 150 | −3.77 | 4 | INVENTION EXAMPLE |
| EXAMPLE 361 | 31 | 8 | 30 | 150 | NaN | 5 | INVENTION EXAMPLE |
| EXAMPLE 362 | 31 | 0 | 30 | 100 | −2.85 | 3 | REFERENCE EXAMPLE |
| EXAMPLE 363 | 31 | 0 | 30 | 150 | −3.09 | 3 | REFERENCE EXAMPLE |
| EXAMPLE 364 | 31 | 4 | 30 | 100 | −3.16 | 3 | INVENTION EXAMPLE |
| EXAMPLE 365 | 31 | 8 | 30 | 100 | −3.22 | 4 | INVENTION EXAMPLE |
| EXAMPLE 366 | 31 | 0 | 40 | 150 | −3.33 | 4 | REFERENCE EXAMPLE |
| EXAMPLE 367 | 31 | 4 | 40 | 150 | −3.42 | 4 | INVENTION EXAMPLE |
| EXAMPLE 368 | 31 | 0 | 40 | 100 | −3.51 | 4 | REFERENCE EXAMPLE |
| EXAMPLE 369 | 31 | 4 | 40 | 100 | −3.52 | 4 | INVENTION EXAMPLE |
| EXAMPLE 370 | 31 | 8 | 40 | 150 | −3.60 | 4 | INVENTION EXAMPLE |
| EXAMPLE 371 | 31 | 8 | 40 | 100 | −3.63 | 4 | INVENTION EXAMPLE |
| EXAMPLE 372 | 31 | 4 | 30 | 150 | −3.65 | 4 | INVENTION EXAMPLE |
| EXAMPLE 373 | 32 | 8 | 30 | 150 | NaN | 5 | INVENTION EXAMPLE |
| EXAMPLE 374 | 32 | 0 | 30 | 100 | −2.54 | 1 | COMPARATIVE EXAMPLE |
| EXAMPLE 375 | 32 | 4 | 30 | 100 | −2.72 | 2 | COMPARATIVE EXAMPLE |
| EXAMPLE 376 | 32 | 0 | 30 | 150 | −2.74 | 2 | COMPARATIVE EXAMPLE |
| EXAMPLE 377 | 32 | 8 | 30 | 100 | −2.91 | 3 | INVENTION EXAMPLE |
| EXAMPLE 378 | 32 | 0 | 40 | 150 | −2.98 | 3 | REFERENCE EXAMPLE |
| EXAMPLE 379 | 32 | 4 | 40 | 150 | −3.02 | 3 | INVENTION EXAMPLE |
| EXAMPLE 380 | 32 | 4 | 40 | 100 | −3.03 | 3 | INVENTION EXAMPLE |
| EXAMPLE 381 | 32 | 0 | 40 | 100 | −3.05 | 3 | REFERENCE EXAMPLE |
| EXAMPLE 382 | 32 | 4 | 30 | 150 | −3.08 | 3 | INVENTION EXAMPLE |
| EXAMPLE 383 | 32 | 8 | 40 | 100 | −3.11 | 3 | INVENTION EXAMPLE |
| EXAMPLE 384 | 32 | 8 | 40 | 150 | −3.28 | 4 | INVENTION EXAMPLE |

It should be noted that, in Table 2, "NaN" in items of quantitative values of moiré means that since an intensity is small and elements which do not contribute to occurrence of moiré are removed through threshold processing, a quantitative value of moiré is not obtained, moiré does not occur, and moiré is not visually perceived.

Table 2 shows Examples 1 to 384.

Here, in Examples 2 and 3, 5 and 6, 8 to 10, 12, 15 and 16, 18, 20 and 21, 23 and 24, 29 to 36, 38 to 43, 46 and 47, 50 to 53, 56 to 59, 61, 64 to 67, 69 and 70, 72, 75 to 78, 80 and 81, 83 to 85, 93 and 94, 96 and 97, 100 to 102, 105 to 109, 112 to 114, 117 to 122, 127 and 128, 130 and 131, 134 to 136, 138, 140 and 141, 143 and 144, 152 and 153, 154 to 159, 161, 163 and 164, 166 and 167, 170 to 175, 179 and 180, 182 to 184, 188 to 192, 196, 198, 200 and 201, 203 and 204, 219 to 223, 225 and 226, 228, 230 and 231, 233, 235, 237 to 240, 242, 244 to 246, 248 to 250, 252, 260 to 262, 264, 270, 272 to 274, 276, 288, 290, 292, 294 to 297, 299 and 300, 307 to 309, 311 and 312, 320 and 321, 323 to 326, 328, 330 and 331, 333 to 335, 344 and 345, 347 to 349, 354, 356 to 358, 360 and 361, 364 and 365, 367, 369 to 373, 377, 379 and 380, and 382 to 384, quantitative values of moiré were equal to or less than −2.80, and evaluation results thereof were also equal to or greater than 3. The above-mentioned examples are examples of the present invention which are excellent in terms of visibility of moiré.

In contrast, in Examples 13 and 14, 86 to 91, 123 to 126, 145 to 150, 193 to 195, 205 to 216, 229, 253 to 258, 265 to 269, 277 to 287, 301 to 306, 313 to 318, 337 to 342, 350 to 353, and 374 to 376, quantitative values of moiré were greater than −2.80, and evaluation results thereof were equal to or less than 2. The above-mentioned examples are comparative examples which are disadvantageous in terms of visibility of moiré.

In addition, in Examples 1, 4, 7, 11, 17, 19, 22, 25 to 28, 37, 44 and 45, 48 and 49, 54 and 55, 60, 62 to 63, 68, 71, 73 and 74, 79, 82, 92, 95, 98 and 99, 103 and 104, 110 and 111, 115 and 116, 129, 132 to 133, 137, 139, 142, 151, 154, 160, 162, 165, 168 and 169, 176 to 178, 181, 185 to 187, 197, 199, 202, 217 and 218, 224, 227, 232, 234, 236, 241, 243, 247, 251, 259, 263, 271, 275, 289, 291, 293, 298, 310, 319, 322, 327, 329, 332, 336, 343, 346, 355, 359, 362 and 363, 366, 368, 378, and 381, quantitative values (indicators of evaluation) of moiré were equal to or less than −2.80, and evaluation results thereof were equal to or greater than 3. The above-mentioned examples are reference examples which are favorable in terms of visibility of moiré while the combined mesh pattern is not randomized (randomicity of 0%). As described above, it can be seen from the reference examples and the comparative examples (randomicity of 0%) in which randomization is not performed that the quantitative value of moiré of −2.80 is appropriate.

From the above description, in the conductive film of the present invention having the randomized combined wiring pattern for allowing the quantitative value (the indicator of evaluation) of moiré to satisfy the range, even if the cycles and the intensities of the BM patterns of the display, the emission intensity of the display, and the like are different, even at the time of front observation, and even at the time of oblique observation, it is possible to suppress occurrence of moiré, and it is possible to greatly improve visibility.

From the above description, effects of the present invention are clarified.

In the present invention, in a manner similar to that of the above-mentioned examples, wiring patterns having various pattern shapes are provided in advance, and thus it is possible to determine the conductive film that has the upper and lower wiring patterns including the random wiring pattern as the combined wiring pattern which is optimized in the evaluation method of the present invention. However, in a case where the indicator of evaluation of moiré for the single wiring pattern is less than a predetermined value, it is possible to determine the conductive film which has the optimized wiring pattern by repeating the following process: transmittance image data of the wiring pattern is updated to transmittance image data of a new wiring pattern, image data of a new combined wiring pattern is created, and the quantitative value (the indicator of evaluation) of moiré is obtained by applying the above-mentioned evaluation method of the present invention.

Here, the updated new wiring pattern may be provided in advance, and may be newly created. It should be noted that, in the case where the pattern is newly created, any one or more of the rotation angle, the pitch, and the pattern width of the transmittance image data of the wiring pattern may be changed, and the shape and the size of the opening portion of the wiring pattern may be changed. In the present invention, it is apparent that it is necessary to at least partially randomize at least one of the combined wiring patterns.

Hereinbefore, the conductive film according to the present invention, the display device comprising the conductive film, and the method of evaluating the conductive film have been described with reference to various embodiments and examples. However, it is apparent that the present invention is not limited to the embodiments and the examples and may be improved or modified in various forms without departing from the scope of the present invention.

EXPLANATION OF REFERENCES 10, 11, 11A conductive film
12 transparent substrate
14 thin line made of metal (thin metal line)
16, 16a, 16b wiring portion
18, 18a, 18b adhesive layer
20, 20a, 20b protective layer
21 mesh shape wire
22 opening portion
23a electrode portion
23b dummy electrode portion (non-electrode portion)
24 combined wiring pattern
24a first (upper) wiring pattern
24b second (lower) wiring pattern
25a irregular parallelogram wiring pattern
25b regular rhomboid wiring pattern
25 disconnection portion (cut-off portion)
26 dummy electrode portion
28, 28a, 28b wiring layer
30 display unit
32, 32r, 32g, 32b pixel
34 black matrix (BM)
38 BM pattern
40 display device
44 touch panel

What is claimed is:

1. A conductive film that is provided on a display unit of a display device, the conductive film comprising:
 a transparent substrate; and
 two wiring portions that are respectively provided on both sides of the transparent substrate and that each have a plurality of thin metal lines, or
 a first transparent substrate;
 a first wiring portion that is formed on one side of the first transparent substrate and has a plurality of thin metal lines;

a second transparent substrate that is disposed on the first wiring portion; and a second wiring portion that is formed on one side of the second transparent substrate and has a plurality of thin metal lines, wherein the plurality of thin metal lines has a mesh-shaped wiring pattern, and a plurality of opening portions is arrayed in each wiring portion, wherein the plurality of thin metal lines of at least one wiring portion of the two wiring portions or two wiring portions including the first wiring portion and the second wiring portion is formed in a wiring pattern where the opening portions, of which angles are maintained and pitches are made to be irregular with respect to rhomboid shapes of a regular rhomboid wiring pattern, have parallelogram shapes, wherein in the display unit, pixels, which include a plurality of sub-pixels emitting light with a plurality of colors that are at least three colors different from each other, are arrayed in pixel array patterns, wherein the conductive film is provided on the display unit such that the wiring patterns of the two wiring portions overlap with the pixel array patterns of the display unit, wherein from at least one point of view, the wiring patterns of the two wiring portions are formed such that an indicator of evaluation of moirés is equal to or less than an evaluation threshold value, where in frequencies and intensities of the moirés of respective colors of a plurality of colors calculated from a first peak frequency and a first peak intensity of a plurality of first spectrum peaks of two-dimensional Fourier spectra of image data of the wiring patterns of the two wiring portions overlapping with each other and a second peak frequency and a second peak intensity of a plurality of second spectrum peaks of two-dimensional Fourier spectra of luminance image data of the pixel array patterns of the respective colors when light beams with the plurality of colors are respectively emitted, the indicator of evaluation is calculated from evaluation values of the moirés of the respective colors obtained by applying human visual response characteristics in accordance with an observation distance to intensities of the moirés equal to or greater than a first intensity threshold value among intensities of the moirés at frequencies of the moirés equal to or less than a frequency threshold value defined on the basis of a display resolution of the display unit, wherein the evaluation threshold value is −2.80, and wherein the indicator of evaluation is equal to or less than −2.80 as a common logarithm.

2. The conductive film according to claim 1, wherein a predetermined range of the irregularity is greater than 0% and equal to or less than 10%.

3. The conductive film according to claim 1, wherein the luminance image data of the pixel array patterns of the respective colors is normalized luminance image data that is obtained by normalizing the luminance image data obtained by converting captured image data of the colors, which is obtained by capturing images of the pixel array patterns of the respective colors displayed on a display screen of the display unit, into luminance values, when the light beams with the plurality of colors are separately emitted.

4. The conductive film according to claim 3, wherein images of the pixel array patterns of the respective colors displayed on the display screen of the display unit are displayed on the display unit when the light beams with the plurality of colors are separately emitted at a maximum intensity which can be set for each color.

5. The conductive film according to claim 4, wherein when the plurality of colors is three colors such as red, green, and blue, the captured image data of the images of the pixel array patterns of the respective colors such as red, green, and blue is image data that is obtained by imaging after adjusting white balance to a white color of a Macbeth chart.

6. The conductive film according to claim 1, wherein the luminance image data of the images of the pixel array patterns of the respective colors of the plurality of colors is data that is obtained by giving the luminance image data in which a measured luminance value is normalized through a product between a resolution of the display unit and an area having a value of a mask image, where the mask image is created from the captured image data which is obtained by capturing the image of the pixel array pattern of a current color displayed on the display screen of the display unit through a microscope, when the light beams of the respective colors of the plurality of colors are separately emitted in the display unit, and wherein the luminance image data is obtained by normalizing a luminance of a display unit of a reference display device to 1.0.

7. The conductive film according to claim 6, wherein when the plurality of colors is three colors such as red, green, and blue, the measured luminance value is a luminance value which is obtained from spectrum data of each color of red, green, and blue by separately performing display for each color of red, green, and blue and performing measurement through a spectrometer, and wherein the mask image is an image that is obtained by binarizing the captured image data which is obtained through imaging of the microscope.

8. The conductive film according to claim 1, wherein the plurality of thin metal lines of one wiring portion of the two wiring portions constitutes the irregular parallelogram wiring pattern, and wherein the plurality of thin metal lines of another wiring portion constitutes the regular rhomboid wiring pattern.

9. The conductive film according to claim 1, wherein at least one wiring portion of the two wiring portions includes an electrode portion and a non-electrode portion, wherein the plurality of thin metal lines of one of the electrode portion and the non-electrode portion constitutes the irregular parallelogram wiring pattern, and wherein the plurality of thin metal lines of another of the electrode portion and the non-electrode portion constitutes the regular rhomboid wiring pattern.

10. The conductive film according to claim 1, wherein the plurality of first spectrum peaks has a peak intensity that is equal to or greater than a first threshold value which is selected from a plurality of spectrum peaks obtained by performing two-dimensional Fourier transform on the image data of the wiring pattern, and wherein for each of the plurality of colors, the plurality of second spectrum peaks has a peak intensity that is equal to or greater than a second threshold value which is selected from a plurality of spectrum peaks obtained by performing two-dimensional Fourier transform on the luminance image data of the pixel array pattern.

11. The conductive film according to claim 1,
wherein a frequency of a moiré corresponding to each color is given as a difference between the first peak frequency and the second peak frequency corresponding to each color, and
wherein an intensity of the moiré corresponding to each color is given as a product between the first peak intensity and the second peak intensity corresponding to each color.

12. The conductive film according to claim 1, wherein an evaluation value of the moiré is calculated by weighting a visual transfer function, which corresponds to the observation distance as the visual response characteristics, to the frequency and the intensity of the moiré through convolution integration.

13. The conductive film according to claim 12, wherein the visual transfer function VTF is given by the following Expression (1), $$VTF=5.05e^{-0.138k}(1-e^{0.1k}) \quad (1)$$

$$k=\pi du/180$$

here, k is a spatial frequency (cycle/deg) defined by a solid angle, u shown in the above-mentioned Expression (1) is a spatial frequency (cycle/mm) defined by a length, and d is defined by an observation distance (mm).

14. The conductive film according to claim 1, wherein the indicator of evaluation of the moirés is calculated using a largest evaluation value among the evaluation values of the plurality of the moirés in which a frequency of one of the moirés is weighted in accordance with the observation distance for each color.

15. The conductive film according to claim 14, wherein the indicator of evaluation of the moirés is a largest sum among sums for the plurality of colors, the sums being obtained by adding the largest evaluation values of the frequencies of all the moirés for each color, each of the largest evaluation value being selected with respect to the frequency of one of the moirés for each color.

16. The conductive film according to claim 1,
wherein the first intensity threshold value is −4.5 as a common logarithm, and the frequency threshold value is a spatial frequency which is obtained from the resolution of the display unit, and
wherein a moiré, which is selected in order to apply the visual response characteristics, has an intensity which is equal to or greater than −3.8.

17. The conductive film according to claim 1,
wherein from at least two points of view of front observation and oblique observation, the evaluation value is obtained for each color of the plurality of colors, and
wherein the indicator of evaluation is a largest evaluation value among evaluation values of respective colors obtained in the at least two points of view.

18. A display device comprising:
a display unit in which pixels, which include a plurality of sub-pixels emitting light with a plurality of colors that are different from each other, are arrayed in pixel array patterns which are repeated in a certain direction and a direction perpendicular to the certain direction; and
the conductive film according to claim 1, the conductive film being provided on the display unit.

19. A method of evaluating a conductive film that is provided on a display unit of a display device and has a transparent substrate, and two wiring portions which are respectively formed on both sides of the transparent substrate and each of which has a plurality of thin metal lines, or a first transparent substrate, a first wiring portion that is formed on one side of the first transparent substrate and has a plurality of thin metal lines, a second transparent substrate that is disposed on the first wiring portion, and a second wiring portion that is formed on one side of the second transparent substrate and has a plurality of thin metal lines, where the plurality of thin metal lines has a mesh-shaped wiring pattern and a plurality of opening portions is arrayed in the wiring portions, the method comprising:

forming the plurality of thin metal lines of at least one wiring portion of the two wiring portions or two wiring portions including the first wiring portion and the second wiring portion in a wiring pattern where the opening portions, of which angles are maintained and pitches are made to be irregular with respect to rhomboid shapes of a regular rhomboid wiring pattern, have parallelogram shapes;

arraying pixels, which include a plurality of sub-pixels emitting light with a plurality of colors that are at least three colors different from each other, in pixel array patterns, in the display unit;

providing the conductive film on the display unit such that the wiring patterns of the two wiring portions overlap with the pixel array patterns of the display unit;

acquiring image data of the wiring patterns of the two wiring portions overlapping with each other and luminance image data of the pixel array patterns of respective colors of the plurality of colors of the display unit, from at least one point of view;

calculating a first peak frequency and a first peak intensity of a plurality of first spectrum peaks of two-dimensional Fourier spectra of image data of the regular rhomboid wiring pattern and a second peak frequency and a second peak intensity of a plurality of second spectrum peaks of two-dimensional Fourier spectra of luminance image data of the pixel array patterns of the respective colors of the plurality of colors, for each color, by performing two-dimensional Fourier transform on the image data of the regular rhomboid wiring pattern and the luminance image data of the pixel array pattern;

calculating frequencies and intensities of moirés of the respective colors of the plurality of colors from the first peak frequency and the first peak intensity of the wiring pattern and the second peak frequency and the second peak intensity of the sub-pixel array patterns of the respective plurality of colors calculated in the above-mentioned manner;

selecting moirés having frequencies equal to or less than a frequency threshold value and intensities equal to or greater than a first intensity threshold value defined on the basis of a display resolution of the display unit, among the frequencies and intensities of the moirés of the respective colors calculated in the above-mentioned manner;

acquiring evaluation values of the moirés of the respective colors by applying human visual response characteristics in accordance with an observation distance to the intensities of the moirés at respective frequencies of the moirés of the respective colors selected in the above-mentioned manner;

calculating an indicator of evaluation of the moirés from the evaluation values of the moirés of the respective colors acquired in the above-mentioned manner; and evaluating the conductive film of which the indicator of evaluation of the moirés calculated in the above-mentioned manner is equal to or less than an evaluation threshold value,
wherein the evaluation threshold value is −2.80, and
wherein the indicator of evaluation is equal to or less than −2.80 as a common logarithm.

* * * * *